US011124803B2

(12) United States Patent
Larue et al.

(10) Patent No.: US 11,124,803 B2
(45) Date of Patent: *Sep. 21, 2021

(54) METHODS AND COMPOSITIONS FOR PPO HERBICIDE TOLERANCE

(71) Applicant: Monsanto Technology LLC, St. Louis, MO (US)

(72) Inventors: Clayton T. Larue, Chesterfield, MO (US); Farhad Moshiri, Chesterfield, MO (US); Joel E. Ream, St. Louis, MO (US); Xuefeng Zhou, St. Louis, MO (US)

(73) Assignee: MONSANTO TECHNOLOGY LLC, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 16/218,822

(22) Filed: Dec. 13, 2018

(65) Prior Publication Data

US 2019/0185873 A1 Jun. 20, 2019

Related U.S. Application Data

(60) Provisional application No. 62/599,386, filed on Dec. 15, 2017.

(51) Int. Cl.
*C12N 15/82* (2006.01)
*C12N 9/02* (2006.01)

(52) U.S. Cl.
CPC ......... *C12N 15/8274* (2013.01); *C12N 9/001* (2013.01); *C12Y 103/03004* (2013.01)

(58) Field of Classification Search
CPC ........................ C12N 9/001; C12N 15/8274
See application file for complete search history.

(56) References Cited

U.S. PATENT DOCUMENTS

| | | | |
|---|---|---|---|
| 5,767,373 | A | 6/1998 | Ward et al. |
| 5,939,602 | A | 8/1999 | Volrath et al. |
| 6,084,155 | A | 7/2000 | Volrath et al. |
| 2002/0042932 | A1 | 4/2002 | Back et al. |
| 2016/0374339 | A1 | 12/2016 | Aponte et al. |
| 2017/0037427 | A1 | 2/2017 | Evdokimov et al. |
| 2017/0058290 | A1 | 3/2017 | Evdokimov et al. |
| 2017/0175131 | A1 | 6/2017 | Ellis et al. |
| 2018/0044690 | A1 | 2/2018 | Larue et al. |

FOREIGN PATENT DOCUMENTS

| | | | | |
|---|---|---|---|---|
| WO | WO 98/33927 | * | 8/1998 | ......... C12N 15/8274 |
| WO | WO 2001/026458 A2 | | 4/2001 | |

OTHER PUBLICATIONS

Zwerschke et al Bioscience Reports vol. 34, article e00124 (Year: 2014).*
Taverniers et al Environ. Biosafety Res. vol. 7, pp. 197-218 (Year: 2008).*
Gen Bank Accession No. EHT98690.1 National Center for Biological Information, NIH Bethesda, Maryland Wang et al (Year: 2012).*
USPTO: Notice of Allowance and Fee(s) Due regarding U.S. Appl. No. 15/660,660, dated Apr. 14, 2020.
GenBank Accession No. ORJ22714.1, dated Apr. 14, 2017.
Patzold et al., "A codon deletion confers resistance to herbicides inhibiting protoporphyrinogen oxidase", PNAS, 2006, 103(33):12329-12334.
Boynton, et al., "Identification of *Escherichia coli* HemG as a Novel, Menadione-Dependent Flavodoxin with Protoporphyrinogen Oxidase Activity," Biochemistry 48(29):6705-6711 (2009).
Sasarman, et al., "Mapping of a new hem Gene in *Escherichia coli* K12," J Gen Microbiol 113:297-303 (1979).
Sasarman, et al., "Nucleotide Sequence of the hemG Gene Involved in the Protoporphyrinogen Oxidase Activity of *E. coli* K12," Can J Microbiol 39:1155-1161 (1993).
Zwerschke, et al., "*Leishmania major* Possesses a Unique HemG-type Protoporphyrinogen IX Oxidse," Biosci Rep 34(4): art:300124 (2014).
U.S. Appl. No. 16/452,305, filed Jun. 25, 2019, Evdokimov et al.
U.S. Appl. No. 16/452,327, filed Jun. 25, 2019, Evdokimov et al.
U.S. Appl. No. 16/452,349, filed Jun. 25, 2019, Evdokimov et al.
USPTO: Non-Final Office Action regarding U.S. Appl. No. 15/224,276, dated Feb. 15, 2019.
Response to Non-Final Office Action regarding U.S. Appl. No. 15/224,276, dated Apr. 5, 2019.
International Search Report and Written Opinion regarding PCT Application No. PCT/US2018/065449, dated Jul. 5, 2019, 10 pages.
USPTO: Notice of Allowance regarding U.S. Appl. No. 15/224,276, dated May 1, 2019.
USPTO: Notice of Allowance regarding U.S. Appl. No. 15/228,993, dated May 1, 2019.
U.S. Appl. No. 16/931,427, filed Jul. 16, 2020, Larue et al.

* cited by examiner

*Primary Examiner* — David H Kruse
(74) *Attorney, Agent, or Firm* — Dentons US LLP; Elizabeth Millard

(57) ABSTRACT

The invention relates to biotechnology and provides novel recombinant DNA molecules and engineered proteins for conferring tolerance to protoporphyrinogen oxidase-inhibitor herbicides. The invention also provides herbicide tolerant transgenic plants, seeds, cells, and plant parts containing the recombinant DNA molecules, as well as methods of using the same.

27 Claims, 6 Drawing Sheets
Specification includes a Sequence Listing.

Figure 1A

```
H_N90     -MKALVLYSTRDGQTHAIASYIASCMKEK-AECDVIDL-THGEHVNLTQYDQVLIGASIR
HemG001   -MKALILYSSRDGQTHAIASYIANELKEK-CSCDVVDL-AHAERVDLKSYDQVMIGASIR
HemG003   -MKALILYSSRDGQTHAIASYIANELKEK-CSCDVVDL-AHAERVDLKSYDQVMIGASIR
H_N30     -MKALILFSSREGQTREIASYIANSIKEE-MECDVFNI-LRVEQIDWSQYDRVLIGGSIH
H_N40     -MKALIVFSSRDGQTRAIASYIANTLKGT-LECDVVNV-LNANDIDLSQYDRVAIGASIR
H_N60     -MKALILYSTRDGQTRKIASSIADVIRQQ-QQCDVLNI-KDASLPDWAQYDRVLIGASIR
H_N20     -MKALILFSTRDGQTQKIASAIADEIKGQ-QSCDVINI-QDAKTLDWQQYDRVLIGASIR
H_N70     -MKALILFSSRDGQTQLIASSIAKELEGK-QACDVLNI-LDTTNVEWTQYDRVLIGASIR
HemG005   -MSYLLLYSTQDGQTKKIIMRIAENLRRSGVSCDLRDL-AAVKQVNLASYQKVMVGASIR
H_N100    -MKTLILFSTRDGQTREIAAFLASELKEQGIYADVINL-NRTEEIAWQEYDRVVIGASIR
HemG002   -MKTLILFSTRDGQTREIASYLASELKEMGIWADVVNL-HRAEEPDWDSYDRVVIGASIR
HemG004   MAKALFLYSTREGQTKKIFQHISEQMKE--FDCEMIDL-HSVESVDFSQYQRVLIGASIR
H_N110    -MKILILFSTRDGQTREIAASLASELKEQAFDVDVVNL-HRAENIAWEEYDGVVIGASIR
H_N10     -MKTLILFSTRDGQTREIASYLASELKELGIQADVANV-HRIEEPQWENYDRVVIGASIR
HemG006   -MKALLLYSTREGQTKKIMHHIAQQLQG---YECQFVDL-HECHTMDLTQYDKVLIGASIR
HemG007   MKKALLLHSSREGQTLKILRAIESELSES-YQCELVDL-HEMPEVNWEDYDKVLIGASIR
H_N50     -MKTLILFSTRDGQTHKIARHIAGVLEEQGKACELVDL-LQPGEPDWSTVECVVLGASIR
HemG013   -MKLLVLYSSCEGQTLKIAKHIVSQQAGE-VAADYIQIDSNQQSLDLTAYDKVLIGASIR
HemG008   -MKVLLLYTTHEKQTFKIMQRIENQLAGK-CDCDVIEL-LPSTNIDLTKYQAVLLGCSIR
HemG009   -MQTLIIYSTIDGQTLEICRKIKAFAERAGEKVSLFSL-EQAEAINLADVDKVLIGASIR
HemG011   MSTTLLIYSTTDGHTKKISQKIQEIIEAKGQKVTLLPI-EEITAAALDSHDKIVIGASIR
HemG012   MSNILIIYSSVHGQTRKICAYLEDKFVALGDKVTMSSL---DQVPDLNDFDKVVLGASIR
HemG010   MNKILIIYSSVHGQTRKICEYIASQLRASDYGCEVRLA-SLEEQFDLDSFDKIIIGASIR

H_N90     YGHFNAVLDKFIKRNVDQLNNMPSAFFCVNLTARKPE--KRTPQTNPYVRKFLLATPWQP
HemG001   YGHFNPVLDKFVKKHAGILNHMPSAFFGVNLTARKPE--KRTPQTNAYVRKFLLASPWEP
HemG003   YGHFNPVLDKFVKKHAETLNRMPSAFFGVNLTARKPE---KRTPQTNAYVRKFLLASPWEP
H_N30     YGHFHPAVAKFVKRHLELQQRSSGFFCVNLTARKAD--KRTPQTNAYMRKFLLQSPWQP
H_N40     YGRFHPAVNQFIRKHLTSLQQLPSAFFSVNLTARKPE--KRTIQTNAYTRKFLLNSPWQP
H_N60     YGHFQPVVDKFVKQHLELQQRTSGFFSVNLTARKPE--KRSPETNAYTQKFLAHSPWQP
H_N20     YGHFQPVVNEFVKHNLLALQQRVSGFFSVNLTARKPE---KRSPETNAYTVKFLAQSPWQP
H_N70     YGHFHPAVAEFVKRHQRELQQRSSGFFSVNLTARKPE--KRSPETNAYTAKFLNQSPWQP
HemG005   YGHFNSVLHKFVTHHQKQLNQKPTAFFGVNLTARKPE----KRTPETNAYVRKFLMKSPWQP
H_N100    YGHFHPAVDRFVKKHTETLNSLPGAFFSVNLVARKAE---KRTPQTNSYTRKFLLNSPWKP
HemG002   YGHYHSAFQEFVKKYATRLNGMPSAFYSVNLVARKAE---KRTPQTNSYARKFLMSSPWRP
HemG004   YGHLNKKLYQFIEHNLSQLQTAKSAFFCVNLTARKEDQAKDTPEGSAYIKTFLSKSPWQP
H_N110    YGHFHSTLNSFVKKHQQALKKLPGAFYSVNLVARKPE---KRTPQTNSYTRKFLLDSPWQP
H_N10     YGHYHSAFQEFVKKHATRLNSMPSAFYSVNLVARKPE----KRTPQTNSYARKFLMNSQWRP
HemG006   YGKLNAKLYQFIDAHIKQLEQVKAAFYCVNLTARKVEQGKDTPEGSVYIKTFLKKSPWQP
HemG007   YGHLNKKLYRFIETNLSSLKNKKAAFFCVNLTARKPG--KDTPEGSVYMKKFLKRSPWQP
H_N50     YGHFHKSFIRFVNTHAQRLNNMPGALFTVNLVARKPE----KQSPQTNSYTRKFLAASPWQP
HemG013   YGKFRPQLYSLLAEYQNQLANVPVAFFGVCLTARKPE---KNTPETSVYMKKLNLNAAWMP
HemG008   YGFYSKVMKKFIDNNYQQLNKMRSGFFGVNVVARKPH---KNTPETNSYTRKFLAKIAWQP
HemG009   YGKHRPELYQFVNRNHAVLSAKVNGFFTVNVVARKPL---KNTPETNPYMQKFLKLSLWQP
HemG011   YGKHQKVVADFIEQNKTTLESKPSAFYTVNLVARKPE---KCQPDTNPYIIKFLSQLDWQP
HemG012   HGKHNPNVYDFISQNRGILEKKTSSFFSVNLVARKPA--KNTPQTNPYMLAFIEKSEWKP
HemG010   HGKHNPEVYHFIDTHLVALETKSSSFFSVSLVARKAS--RNTPESNPYMQAFLSKTLWRP
```

Figure 1B

```
H_N90     ALCGVFAGALRYPRYRWIDKVMIQLIMRMTGGETDTSKE-VEYTDWEQVKKFAEDFAKLS
HemG001   AMCGVFAGALRYPRYRWFDKVMIQLIMRMTGGETDTRKE-VEYTDWQQVAKFAEDFGQIS
HemG003   AMCGVFAGALRYPRYRWFDKVMIQLIMRMTGGETDTRKE-VEYTDWQQVAKFAEDFGQIS
H_N30     DCCAVFAGALRYTRYRWFDRVMIQLIMRMTGGETDTSKE-VEYTDWTQVARFAQEFAHLP
H_N40     DLCCVFAGALRYPRYRWFDRVMIQLIMRITGGETDSTKE-IEYTDWQQVARFAQDFAQLA
H_N60     DCCAVFAGALYYPRYRWFDRVMIQLIMRMTGGETDSTKE-VEYTDWQQVSTFANDFAQLP
H_N20     DCCAVFAGALYYPRYRWFDRVMIQFIMRMTGGETDASKE-VEYTDWQQVQRFARDFAQLP
H_N70     DCCAVFAGALRYPRYRWFDRIMIQLIMRMTGGETDSSKE-VEYTDWQQVTRFAQEFARLP
HemG005   DLCEVFAGALLYPRYKWLDRVMIQIIMRMTGGETDTTKE-IEYTDWAQVDRFSEMFLQI-
H_N100    AACAVFAGALRYPRYRWYDRFMIRLIMKMTGGETDTRKE-VVYTDWSQVASFAREIVQLT
HemG002   DYCAVIAGALRYPRYRWYDRLMIKLIMKMSGGETDTSKE-VVYTDWEQVAHFAREIAHLT
HemG004   ELIGVFAGALYYPRYNWFDKTMIKFIMSMTGGETDTSKE-VEYTNWGKVTLFADKFQNL-
H_N110    DLSAVFAGALRYPRYNWYDRIMIRLIMKITGGETDTRKE-VVYTDWQQVTHFAHEIVQLV
H_N10     DRCAVIAGALRYPRYRWYDRFMIKLIMKMSGGETDTRKE-VVYTDWEQVANFAREIAHLT
HemG006   SLIGVFAGALYYPRYRPIDRMMIRFIMKLTGGETDTTKE-VEYTDWEKVSLFAKKFEQL-
HemG007   QLLDVFAGALYYPRYRFFDRVMIQFIMKMTGGETDPTKE-IEYTNWDRVKVFSGQFRSL-
H_N50     QRCQVFAGALRYPRYSWYDRMMIRLIMKMAGGETDTRKE-VEYTDWQSVTRFAREIAQLP
HemG013   KLQAVFAGALLYSKYTWWQALLIQFIMKMTGSTDRSQD-LELTDWAKVDEFATQFAKLD
HemG008   TIKAVFAGALYYPKYNWFDRNMVRFIMWLGKGDTDVTKPIIEYTDWAKVDQFAELFYTQT
HemG009   QHLAVFAGKIDYPKYGLFDRTMICFIMWMTKGPTDLKGT-FEFTDWAKVEAFGTHFSKL-
HemG011   SLQGVFAGKLDYQKYGFIDRNMIRFIMWMTKGPTDPKTN-IEFTNWEAVDQFANGVVELS
HemG012   NLLQVFAGSLNYQGYGIVDRNIIRFIMWMTKGPTDAQTN-IEYTDWAKVDLFSSEFHAL-
HemG010   NLVKVFAGKLDYQGYNWLDRSIIRFIMWITKGPTAVNTK-IEYTDWQLVDVFVKELELL-

H_N90     YKKAL-
HemG001   YKKSH-
HemG003   YKKSH-
H_N30     GKTQ--
H_N40     AKNPA-
H_N60     GKS---
H_N20     GKSY--
H_N70     GKTS--
HemG005   ------
H_N100    RSSRL-
HemG002   NKSSAK
HemG004   ------
H_N110    RK----
H_N10     DKPTLK
HemG006   ------
HemG007   ------
H_N50     GETR--
HemG013   K-----
HemG008   YS----
HemG009   ------
HemG011   ------
HemG012   ------
HemG010   ------
```

Figure 2

Second Base in Codon

| | U | C | A | G | |
|---|---|---|---|---|---|
| U | UUU⎱Phe<br>UUC⎰<br>UUA⎱Leu<br>UUG⎰ | UCU⎱<br>UCC⎱Ser<br>UCA⎰<br>UCG⎰ | UAU⎱Tyr<br>UAC⎰<br>UAA Stop<br>UAG Stop | UGU⎱Cys<br>UGC⎰<br>UGA Stop<br>UGG Trp | U<br>C<br>A<br>G |
| C | CUU⎱<br>CUC⎱Leu<br>CUA⎰<br>CUG⎰ | CCU⎱<br>CCC⎱Pro<br>CCA⎰<br>CCG⎰ | CAU⎱His<br>CAC⎰<br>CAA⎱Gln<br>CAG⎰ | CGU⎱<br>CGC⎱Arg<br>CGA⎰<br>CGG⎰ | U<br>C<br>A<br>G |
| A | AUU⎱<br>AUC⎱Ile<br>AUA⎰<br>AUG Met or Start | ACU⎱<br>ACC⎱Thr<br>ACA⎰<br>ACG⎰ | AAU⎱Asn<br>AAC⎰<br>AAA⎱Lys<br>AAG⎰ | AGU⎱Ser<br>AGC⎰<br>AGA⎱Arg<br>AGG⎰ | U<br>C<br>A<br>G |
| G | GUU⎱<br>GUC⎱Val<br>GUA⎰<br>GUG⎰ | GCU⎱<br>GCC⎱Ala<br>GCA⎰<br>GCG⎰ | GAU⎱Asp<br>GAC⎰<br>GAA⎱Glu<br>GAG⎰ | GGU⎱<br>GGC⎱Gly<br>GGA⎰<br>GGG⎰ | U<br>C<br>A<br>G |

First Base in Codon (rows) / Third Base in Codon (columns)

SEQUENCE LISTING

<160> NUMBER OF SEQ ID NOS: 278

<210> SEQ ID NO 1
<211> LENGTH: 179
<212> TYPE: PRT
<213> ORGANISM: Enterobacter cloacae

<400> SEQUENCE: 1

Met Lys Ala Leu Val Leu Tyr Ser Thr Arg Asp Gly Gln Thr His Ala
1               5                   10                  15

```
Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 2
<211> LENGTH: 181
<212> TYPE: PRT
<213> ORGANISM: Escherichia coli

<400> SEQUENCE: 2

Met Lys Thr Leu Ile Leu Phe Ser Thr Arg Asp Gly Gln Thr Arg Glu
1               5                   10                  15

Ile Ala Ser Tyr Leu Ala Ser Glu Leu Lys Glu Leu Gly Ile Gln Ala
                20                  25                  30

Asp Val Ala Asn Val His Arg Ile Glu Glu Pro Gln Trp Glu Asn Tyr
            35                  40                  45

Asp Arg Val Val Ile Gly Ala Ser Ile Arg Tyr Gly His Tyr His Ser
        50                  55                  60

Ala Phe Gln Glu Phe Val Lys Lys His Ala Thr Arg Leu Asn Ser Met
65                  70                  75                  80

Pro Ser Ala Phe Tyr Ser Val Asn Leu Val Ala Arg Lys Pro Glu Lys
                85                  90                  95

Arg Thr Pro Gln Thr Asn Ser Tyr Ala Arg Lys Phe Leu Met Asn Ser
            100                 105                 110

Gln Trp Arg Pro Asp Arg Cys Ala Val Ile Ala Gly Ala Leu Arg Tyr
        115                 120                 125

Pro Arg Tyr Arg Trp Tyr Asp Arg Phe Met Ile Lys Leu Ile Met Lys
        130                 135                 140

Met Ser Gly Gly Glu Thr Asp Thr Arg Lys Glu Val Val Tyr Thr Asp
145                 150                 155                 160

Trp Glu Gln Val Ala Asn Phe Ala Arg Glu Ile Ala His Leu Thr Asp
                165                 170                 175

Lys Pro Thr Leu Lys
            180

<210> SEQ ID NO 3
<211> LENGTH: 178
```

```
<212> TYPE: PRT
<213> ORGANISM: Pantoea ananatis

<400> SEQUENCE: 3
```

Met Lys Ala Leu Ile Leu Phe Ser Thr Arg Asp Gly Gln Thr Gln Lys
1               5                   10                  15

Ile Ala Ser Ala Ile Ala Asp Glu Ile Lys Gly Gln Gln Ser Cys Asp
                20                  25                  30

Val Ile Asn Ile Gln Asp Ala Lys Thr Leu Asp Trp Gln Gln Tyr Asp
            35                  40                  45

Arg Val Leu Ile Gly Ala Ser Ile Arg Tyr Gly His Phe Gln Pro Val
        50                  55                  60

Val Asn Glu Phe Val Lys His Asn Leu Leu Ala Leu Gln Gln Arg Val
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Val Lys Phe Leu Ala Gln Ser Pro
            100                 105                 110

Trp Gln Pro Asp Cys Cys Ala Val Phe Ala Gly Ala Leu Tyr Tyr Pro
        115                 120                 125

Arg Tyr Arg Trp Phe Asp Arg Val Met Ile Gln Phe Ile Met Arg Met
    130                 135                 140

Thr Gly Gly Glu Thr Asp Ala Ser Lys Glu Val Glu Tyr Thr Asp Trp
145                 150                 155                 160

Gln Gln Val Gln Arg Phe Ala Arg Asp Phe Ala Gln Leu Pro Gly Lys
                165                 170                 175

Ser Tyr

```
<210> SEQ ID NO 4
<211> LENGTH: 178
<212> TYPE: PRT
<213> ORGANISM: Erwinia toletana

<400> SEQUENCE: 4
```

Met Lys Ala Leu Ile Leu Phe Ser Ser Arg Glu Gly Gln Thr Arg Glu
1               5                   10                  15

Ile Ala Ser Tyr Ile Ala Asn Ser Ile Lys Glu Glu Met Glu Cys Asp
                20                  25                  30

Val Phe Asn Ile Leu Arg Val Glu Gln Ile Asp Trp Ser Gln Tyr Asp
            35                  40                  45

Arg Val Leu Ile Gly Gly Ser Ile His Tyr Gly His Phe His Pro Ala
        50                  55                  60

Val Ala Lys Phe Val Lys Arg His Leu His Glu Leu Gln Gln Arg Ser
65                  70                  75                  80

Ser Gly Phe Phe Cys Val Asn Leu Thr Ala Arg Lys Ala Asp Lys Arg
                85                  90                  95

Thr Pro Gln Thr Asn Ala Tyr Met Arg Lys Phe Leu Leu Gln Ser Pro
            100                 105                 110

Trp Gln Pro Asp Cys Cys Ala Val Phe Ala Gly Ala Leu Arg Tyr Thr
        115                 120                 125

Arg Tyr Arg Trp Phe Asp Arg Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Thr Gln Val Ala Arg Phe Ala Gln Glu Phe Ala His Leu Pro Gly Lys

```
                        165                 170                 175

Thr Gln

<210> SEQ ID NO 5
<211> LENGTH: 179
<212> TYPE: PRT
<213> ORGANISM: Pectobacterium carotovorum

<400> SEQUENCE: 5

Met Lys Ala Leu Ile Val Phe Ser Ser Arg Asp Gly Gln Thr Arg Ala
1               5                   10                  15

Ile Ala Ser Tyr Ile Ala Asn Thr Leu Lys Gly Thr Leu Glu Cys Asp
            20                  25                  30

Val Val Asn Val Leu Asn Ala Asn Asp Ile Asp Leu Ser Gln Tyr Asp
        35                  40                  45

Arg Val Ala Ile Gly Ala Ser Ile Arg Tyr Gly Arg Phe His Pro Ala
    50                  55                  60

Val Asn Gln Phe Ile Arg Lys His Leu Thr Ser Leu Gln Gln Leu Pro
65                  70                  75                  80

Ser Ala Phe Phe Ser Val Asn Leu Thr Ala Arg Lys Pro Glu Lys Arg
                85                  90                  95

Thr Ile Gln Thr Asn Ala Tyr Thr Arg Lys Phe Leu Leu Asn Ser Pro
            100                 105                 110

Trp Gln Pro Asp Leu Cys Cys Val Phe Ala Gly Ala Leu Arg Tyr Pro
        115                 120                 125

Arg Tyr Arg Trp Phe Asp Arg Val Met Ile Gln Leu Ile Met Arg Ile
    130                 135                 140

Thr Gly Gly Glu Thr Asp Ser Thr Lys Glu Ile Glu Tyr Thr Asp Trp
145                 150                 155                 160

Gln Gln Val Ala Arg Phe Ala Gln Asp Phe Ala Gln Leu Ala Ala Lys
                165                 170                 175

Asn Pro Ala

<210> SEQ ID NO 6
<211> LENGTH: 179
<212> TYPE: PRT
<213> ORGANISM: Shimwellia blattae

<400> SEQUENCE: 6

Met Lys Thr Leu Ile Leu Phe Ser Thr Arg Asp Gly Gln Thr His Lys
1               5                   10                  15

Ile Ala Arg His Ile Ala Gly Val Leu Glu Glu Gln Gly Lys Ala Cys
            20                  25                  30

Glu Leu Val Asp Leu Leu Gln Pro Gly Glu Pro Asp Trp Ser Thr Val
        35                  40                  45

Glu Cys Val Val Leu Gly Ala Ser Ile Arg Tyr Gly His Phe His Lys
    50                  55                  60

Ser Phe Ile Arg Phe Val Asn Thr His Ala Gln Arg Leu Asn Asn Met
65                  70                  75                  80

Pro Gly Ala Leu Phe Thr Val Asn Leu Val Ala Arg Lys Pro Glu Lys
                85                  90                  95

Gln Ser Pro Gln Thr Asn Ser Tyr Thr Arg Lys Phe Leu Ala Ala Ser
            100                 105                 110

Pro Trp Gln Pro Gln Arg Cys Gln Val Phe Ala Gly Ala Leu Arg Tyr
        115                 120                 125
```

Pro Arg Tyr Ser Trp Tyr Asp Arg Met Met Ile Arg Leu Ile Met Lys
            130                 135                 140

Met Ala Gly Gly Glu Thr Asp Thr Arg Lys Glu Val Glu Tyr Thr Asp
145                 150                 155                 160

Trp Gln Ser Val Thr Arg Phe Ala Arg Glu Ile Ala Gln Leu Pro Gly
                165                 170                 175

Glu Thr Arg

<210> SEQ ID NO 7
<211> LENGTH: 177
<212> TYPE: PRT
<213> ORGANISM: Pantoea stewardii

<400> SEQUENCE: 7

Met Lys Ala Leu Ile Leu Tyr Ser Thr Arg Asp Gly Gln Thr Arg Lys
1               5                   10                  15

Ile Ala Ser Ser Ile Ala Asp Val Ile Arg Gln Gln Gln Gln Cys Asp
                20                  25                  30

Val Leu Asn Ile Lys Asp Ala Ser Leu Pro Asp Trp Ala Gln Tyr Asp
            35                  40                  45

Arg Val Leu Ile Gly Ala Ser Ile Arg Tyr Gly His Phe Gln Pro Val
    50                  55                  60

Val Asp Lys Phe Val Lys Gln His Leu His Glu Leu Gln Gln Arg Thr
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Gln Lys Phe Leu Ala His Ser Pro
            100                 105                 110

Trp Gln Pro Asp Cys Cys Ala Val Phe Ala Gly Ala Leu Tyr Tyr Pro
        115                 120                 125

Arg Tyr Arg Trp Phe Asp Arg Val Met Ile Gln Leu Ile Met Arg Met
    130                 135                 140

Thr Gly Gly Glu Thr Asp Ser Thr Lys Glu Val Glu Tyr Thr Asp Trp
145                 150                 155                 160

Gln Gln Val Ser Thr Phe Ala Asn Asp Phe Ala Gln Leu Pro Gly Lys
                165                 170                 175

Ser

<210> SEQ ID NO 8
<211> LENGTH: 178
<212> TYPE: PRT
<213> ORGANISM: Pantoea stewardii

<400> SEQUENCE: 8

Met Lys Ala Leu Ile Leu Phe Ser Ser Arg Asp Gly Gln Thr Gln Leu
1               5                   10                  15

Ile Ala Ser Ser Ile Ala Lys Glu Leu Glu Gly Lys Gln Ala Cys Asp
                20                  25                  30

Val Leu Asn Ile Leu Asp Thr Thr Asn Val Glu Trp Thr Gln Tyr Asp
            35                  40                  45

Arg Val Leu Ile Gly Ala Ser Ile Arg Tyr Gly His Phe His Pro Ala
    50                  55                  60

Val Ala Glu Phe Val Lys Arg His Gln Arg Glu Leu Gln Gln Arg Ser
65                  70                  75                  80

Ser Gly Phe Phe Ser Val Asn Leu Thr Ala Arg Lys Pro Glu Lys Arg
                85                  90                  95

```
Ser Pro Glu Thr Asn Ala Tyr Thr Ala Lys Phe Leu Asn Gln Ser Pro
            100                 105                 110

Trp Gln Pro Asp Cys Cys Ala Val Phe Ala Gly Ala Leu Arg Tyr Pro
        115                 120                 125

Arg Tyr Arg Trp Phe Asp Arg Ile Met Ile Gln Leu Ile Met Arg Met
    130                 135                 140

Thr Gly Gly Glu Thr Asp Ser Ser Lys Glu Val Glu Tyr Thr Asp Trp
145                 150                 155                 160

Gln Gln Val Thr Arg Phe Ala Gln Glu Phe Ala Arg Leu Pro Gly Lys
                165                 170                 175

Thr Ser

<210> SEQ ID NO 9
<211> LENGTH: 180
<212> TYPE: PRT
<213> ORGANISM: Enterobacter cloacae

<400> SEQUENCE: 9

Met Lys Thr Leu Ile Leu Phe Ser Thr Arg Asp Gly Gln Thr Arg Glu
1               5                   10                  15

Ile Ala Ala Phe Leu Ala Ser Glu Leu Lys Glu Gln Gly Ile Tyr Ala
            20                  25                  30

Asp Val Ile Asn Leu Asn Arg Thr Glu Glu Ile Ala Trp Gln Glu Tyr
        35                  40                  45

Asp Arg Val Val Ile Gly Ala Ser Ile Arg Tyr Gly His Phe His Pro
    50                  55                  60

Ala Val Asp Arg Phe Val Lys Lys His Thr Glu Thr Leu Asn Ser Leu
65                  70                  75                  80

Pro Gly Ala Phe Phe Ser Val Asn Leu Val Ala Arg Lys Ala Glu Lys
                85                  90                  95

Arg Thr Pro Gln Thr Asn Ser Tyr Thr Arg Lys Phe Leu Leu Asn Ser
            100                 105                 110

Pro Trp Lys Pro Ala Ala Cys Ala Val Phe Ala Gly Ala Leu Arg Tyr
        115                 120                 125

Pro Arg Tyr Arg Trp Tyr Asp Arg Phe Met Ile Arg Leu Ile Met Lys
    130                 135                 140

Met Thr Gly Gly Glu Thr Asp Thr Arg Lys Glu Val Val Tyr Thr Asp
145                 150                 155                 160

Trp Ser Gln Val Ala Ser Phe Ala Arg Glu Ile Val Gln Leu Thr Arg
                165                 170                 175

Ser Ser Arg Leu
            180

<210> SEQ ID NO 10
<211> LENGTH: 177
<212> TYPE: PRT
<213> ORGANISM: Enterobacter mori

<400> SEQUENCE: 10

Met Lys Ile Leu Ile Leu Phe Ser Thr Arg Asp Gly Gln Thr Arg Glu
1               5                   10                  15

Ile Ala Ala Ser Leu Ala Ser Glu Leu Lys Glu Gln Ala Phe Asp Val
            20                  25                  30

Asp Val Val Asn Leu His Arg Ala Glu Asn Ile Ala Trp Glu Glu Tyr
        35                  40                  45
```

```
Asp Gly Val Val Ile Gly Ala Ser Ile Arg Tyr Gly His Phe His Ser
        50                  55                  60

Thr Leu Asn Ser Phe Val Lys Lys His Gln Gln Ala Leu Lys Lys Leu
 65                  70                  75                  80

Pro Gly Ala Phe Tyr Ser Val Asn Leu Val Ala Arg Lys Pro Glu Lys
                 85                  90                  95

Arg Thr Pro Gln Thr Asn Ser Tyr Thr Arg Lys Phe Leu Leu Asp Ser
            100                 105                 110

Pro Trp Gln Pro Asp Leu Ser Ala Val Phe Ala Gly Ala Leu Arg Tyr
        115                 120                 125

Pro Arg Tyr Asn Trp Tyr Asp Arg Ile Met Ile Arg Leu Ile Met Lys
    130                 135                 140

Ile Thr Gly Gly Glu Thr Asp Thr Arg Lys Glu Val Val Tyr Thr Asp
145                 150                 155                 160

Trp Gln Gln Val Thr His Phe Ala His Glu Ile Val Gln Leu Val Arg
                165                 170                 175

Lys
```

<210> SEQ ID NO 11
<211> LENGTH: 179
<212> TYPE: PRT
<213> ORGANISM: Rahnella aquatilis

<400> SEQUENCE: 11

```
Met Lys Ala Leu Ile Leu Tyr Ser Ser Arg Asp Gly Gln Thr His Ala
 1               5                  10                  15

Ile Ala Ser Tyr Ile Ala Asn Glu Leu Lys Glu Lys Cys Ser Cys Asp
                 20                  25                  30

Val Val Asp Leu Ala His Ala Glu Arg Val Asp Leu Lys Ser Tyr Asp
            35                  40                  45

Gln Val Met Ile Gly Ala Ser Ile Arg Tyr Gly His Phe Asn Pro Val
        50                  55                  60

Leu Asp Lys Phe Val Lys Lys His Ala Gly Ile Leu Asn His Met Pro
 65                  70                  75                  80

Ser Ala Phe Phe Gly Val Asn Leu Thr Ala Arg Lys Pro Glu Lys Arg
                 85                  90                  95

Thr Pro Gln Thr Asn Ala Tyr Val Arg Lys Phe Leu Leu Ala Ser Pro
            100                 105                 110

Trp Glu Pro Ala Met Cys Gly Val Phe Ala Gly Ala Leu Arg Tyr Pro
        115                 120                 125

Arg Tyr Arg Trp Phe Asp Lys Val Met Ile Gln Leu Ile Met Arg Met
    130                 135                 140

Thr Gly Gly Glu Thr Asp Thr Arg Lys Glu Val Glu Tyr Thr Asp Trp
145                 150                 155                 160

Gln Gln Val Ala Lys Phe Ala Glu Asp Phe Gly Gln Ile Ser Tyr Lys
                165                 170                 175

Lys Ser His
```

<210> SEQ ID NO 12
<211> LENGTH: 181
<212> TYPE: PRT
<213> ORGANISM: Salmonella enterica subsp enterica serovar

<400> SEQUENCE: 12

```
Met Lys Thr Leu Ile Leu Phe Ser Thr Arg Asp Gly Gln Thr Arg Glu
 1               5                  10                  15
```

Ile Ala Ser Tyr Leu Ala Ser Glu Leu Lys Glu Met Gly Ile Trp Ala
            20                  25                  30

Asp Val Val Asn Leu His Arg Ala Glu Glu Pro Asp Trp Asp Ser Tyr
        35                  40                  45

Asp Arg Val Val Ile Gly Ala Ser Ile Arg Tyr Gly His Tyr His Ser
    50                  55                  60

Ala Phe Gln Glu Phe Val Lys Lys Tyr Ala Thr Arg Leu Asn Gly Met
65                  70                  75                  80

Pro Ser Ala Phe Tyr Ser Val Asn Leu Val Ala Arg Lys Ala Glu Lys
                85                  90                  95

Arg Thr Pro Gln Thr Asn Ser Tyr Ala Arg Lys Phe Leu Met Ser Ser
            100                 105                 110

Pro Trp Arg Pro Asp Tyr Cys Ala Val Ile Ala Gly Ala Leu Arg Tyr
        115                 120                 125

Pro Arg Tyr Arg Trp Tyr Asp Arg Leu Met Ile Lys Leu Ile Met Lys
    130                 135                 140

Met Ser Gly Gly Glu Thr Asp Thr Ser Lys Glu Val Val Tyr Thr Asp
145                 150                 155                 160

Trp Glu Gln Val Ala His Phe Ala Arg Glu Ile Ala His Leu Thr Asn
                165                 170                 175

Lys Ser Ser Ala Lys
            180

<210> SEQ ID NO 13
<211> LENGTH: 179
<212> TYPE: PRT
<213> ORGANISM: Rahnella aquatilis

<400> SEQUENCE: 13

Met Lys Ala Leu Ile Leu Tyr Ser Ser Arg Asp Gly Gln Thr His Ala
1               5                   10                  15

Ile Ala Ser Tyr Ile Ala Asn Glu Leu Lys Glu Lys Cys Ser Cys Asp
            20                  25                  30

Val Val Asp Leu Ala His Ala Glu Arg Val Asp Leu Lys Ser Tyr Asp
        35                  40                  45

Gln Val Met Ile Gly Ala Ser Ile Arg Tyr Gly His Phe Asn Pro Val
    50                  55                  60

Leu Asp Lys Phe Val Lys Lys His Ala Glu Thr Leu Asn Arg Met Pro
65                  70                  75                  80

Ser Ala Phe Phe Gly Val Asn Leu Thr Ala Arg Lys Pro Glu Lys Arg
                85                  90                  95

Thr Pro Gln Thr Asn Ala Tyr Val Arg Lys Phe Leu Leu Ala Ser Pro
            100                 105                 110

Trp Glu Pro Ala Met Cys Gly Val Phe Ala Gly Ala Leu Arg Tyr Pro
        115                 120                 125

Arg Tyr Arg Trp Phe Asp Lys Val Met Ile Gln Leu Ile Met Arg Met
    130                 135                 140

Thr Gly Gly Glu Thr Asp Thr Arg Lys Glu Val Glu Tyr Thr Asp Trp
145                 150                 155                 160

Gln Gln Val Ala Lys Phe Ala Glu Asp Phe Gly Gln Ile Ser Tyr Lys
                165                 170                 175

Lys Ser His

<210> SEQ ID NO 14

```
<211> LENGTH: 175
<212> TYPE: PRT
<213> ORGANISM: Vibrio pacinii

<400> SEQUENCE: 14

Met Ala Lys Ala Leu Phe Leu Tyr Ser Thr Arg Glu Gly Gln Thr Lys
1               5                   10                  15

Lys Ile Phe Gln His Ile Ser Glu Gln Met Lys Glu Phe Asp Cys Glu
            20                  25                  30

Met Ile Asp Leu His Ser Val Glu Ser Val Asp Phe Ser Gln Tyr Gln
        35                  40                  45

Arg Val Leu Ile Gly Ala Ser Ile Arg Tyr Gly His Leu Asn Lys Lys
    50                  55                  60

Leu Tyr Gln Phe Ile Glu His Asn Leu Ser Gln Leu Gln Thr Ala Lys
65                  70                  75                  80

Ser Ala Phe Phe Cys Val Asn Leu Thr Ala Arg Lys Glu Asp Gln Ala
                85                  90                  95

Lys Asp Thr Pro Glu Gly Ser Ala Tyr Ile Lys Thr Phe Leu Ser Lys
            100                 105                 110

Ser Pro Trp Gln Pro Glu Leu Ile Gly Val Phe Ala Gly Ala Leu Tyr
        115                 120                 125

Tyr Pro Arg Tyr Asn Trp Phe Asp Lys Thr Met Ile Lys Phe Ile Met
    130                 135                 140

Ser Met Thr Gly Gly Glu Thr Asp Thr Ser Lys Glu Val Glu Tyr Thr
145                 150                 155                 160

Asn Trp Gly Lys Val Thr Leu Phe Ala Asp Lys Phe Gln Asn Leu
                165                 170                 175

<210> SEQ ID NO 15
<211> LENGTH: 174
<212> TYPE: PRT
<213> ORGANISM: Xenorhabdus nematophila

<400> SEQUENCE: 15

Met Ser Tyr Leu Leu Leu Tyr Ser Thr Gln Asp Gly Gln Thr Lys Lys
1               5                   10                  15

Ile Ile Met Arg Ile Ala Glu Asn Leu Arg Arg Ser Gly Val Ser Cys
            20                  25                  30

Asp Leu Arg Asp Leu Ala Ala Val Lys Gln Val Asn Leu Ala Ser Tyr
        35                  40                  45

Gln Lys Val Met Val Gly Ala Ser Ile Arg Tyr Gly His Phe Asn Ser
    50                  55                  60

Val Leu His Lys Phe Val Thr His His Gln Lys Gln Leu Asn Gln Lys
65                  70                  75                  80

Pro Thr Ala Phe Phe Gly Val Asn Leu Thr Ala Arg Lys Pro Glu Lys
                85                  90                  95

Arg Thr Pro Glu Thr Asn Ala Tyr Val Arg Lys Phe Leu Met Lys Ser
            100                 105                 110

Pro Trp Gln Pro Asp Leu Cys Glu Val Phe Ala Gly Ala Leu Leu Tyr
        115                 120                 125

Pro Arg Tyr Lys Trp Leu Asp Arg Val Met Ile Gln Ile Met Arg
    130                 135                 140

Met Thr Gly Gly Glu Thr Asp Thr Thr Lys Glu Ile Glu Tyr Thr Asp
145                 150                 155                 160

Trp Ala Gln Val Asp Arg Phe Ser Glu Met Phe Leu Gln Ile
                165                 170
```

<210> SEQ ID NO 16
<211> LENGTH: 174
<212> TYPE: PRT
<213> ORGANISM: Vibrio diazotrophicus

<400> SEQUENCE: 16

```
Met Lys Ala Leu Leu Tyr Ser Thr Arg Glu Gly Gln Thr Lys Lys
1               5                   10                  15
Ile Met His His Ile Ala Gln Gln Leu Gln Gly Tyr Glu Cys Gln Phe
            20                  25                  30
Val Asp Leu His Glu Cys His Thr Met Asp Leu Thr Gln Tyr Asp Lys
        35                  40                  45
Val Leu Ile Gly Ala Ser Ile Arg Tyr Gly Lys Leu Asn Ala Lys Leu
    50                  55                  60
Tyr Gln Phe Ile Asp Ala His Ile Lys Gln Leu Glu Gln Val Lys Ala
65                  70                  75                  80
Ala Phe Tyr Cys Val Asn Leu Thr Ala Arg Lys Val Glu Gln Gly Lys
                85                  90                  95
Asp Thr Pro Glu Gly Ser Val Tyr Ile Lys Thr Phe Leu Lys Lys Ser
            100                 105                 110
Pro Trp Gln Pro Ser Leu Ile Gly Val Phe Ala Gly Ala Leu Tyr Tyr
        115                 120                 125
Pro Arg Tyr Arg Pro Ile Asp Arg Met Met Ile Arg Phe Ile Met Lys
    130                 135                 140
Leu Thr Gly Gly Glu Thr Asp Thr Thr Lys Glu Val Glu Tyr Thr Asp
145                 150                 155                 160
Trp Glu Lys Val Ser Leu Phe Ala Lys Lys Phe Glu Gln Leu
                165                 170
```

<210> SEQ ID NO 17
<211> LENGTH: 174
<212> TYPE: PRT
<213> ORGANISM: Grimontia hollisae

<400> SEQUENCE: 17

```
Met Lys Lys Ala Leu Leu His Ser Ser Arg Glu Gly Gln Thr Leu
1               5                   10                  15
Lys Ile Leu Arg Ala Ile Glu Ser Glu Leu Ser Glu Ser Tyr Gln Cys
            20                  25                  30
Glu Leu Val Asp Leu His Glu Met Pro Glu Val Asn Trp Glu Asp Tyr
        35                  40                  45
Asp Lys Val Leu Ile Gly Ala Ser Ile Arg Tyr Gly His Leu Asn Lys
    50                  55                  60
Lys Leu Tyr Arg Phe Ile Glu Thr Asn Leu Ser Leu Lys Asn Lys
65                  70                  75                  80
Lys Ala Ala Phe Phe Cys Val Asn Leu Thr Ala Arg Lys Pro Gly Lys
                85                  90                  95
Asp Thr Pro Glu Gly Ser Val Tyr Met Lys Lys Phe Leu Lys Arg Ser
            100                 105                 110
Pro Trp Gln Pro Gln Leu Leu Asp Val Phe Ala Gly Ala Leu Tyr Tyr
        115                 120                 125
Pro Arg Tyr Arg Phe Phe Asp Arg Val Met Ile Gln Phe Ile Met Lys
    130                 135                 140
Met Thr Gly Gly Glu Thr Asp Pro Thr Lys Glu Ile Glu Tyr Thr Asn
145                 150                 155                 160
```

-continued

Trp Asp Arg Val Lys Val Phe Ser Gly Gln Phe Arg Ser Leu
              165                 170

<210> SEQ ID NO 18
<211> LENGTH: 177
<212> TYPE: PRT
<213> ORGANISM: Gilliamella apicola

<400> SEQUENCE: 18

Met Lys Val Leu Leu Leu Tyr Thr Thr His Glu Lys Gln Thr Phe Lys
1               5                   10                  15

Ile Met Gln Arg Ile Glu Asn Gln Leu Ala Gly Lys Cys Asp Cys Asp
            20                  25                  30

Val Ile Glu Leu Leu Pro Ser Thr Asn Ile Asp Leu Thr Lys Tyr Gln
        35                  40                  45

Ala Val Leu Leu Gly Cys Ser Ile Arg Tyr Gly Phe Tyr Ser Lys Val
    50                  55                  60

Met Lys Lys Phe Ile Asp Asn Asn Tyr Gln Gln Leu Asn Lys Met Arg
65                  70                  75                  80

Ser Gly Phe Phe Gly Val Asn Val Val Ala Arg Lys Pro His Lys Asn
                85                  90                  95

Thr Pro Glu Thr Asn Ser Tyr Thr Arg Lys Phe Leu Ala Lys Ile Ala
            100                 105                 110

Trp Gln Pro Thr Ile Lys Ala Val Phe Ala Gly Ala Leu Tyr Tyr Pro
        115                 120                 125

Lys Tyr Asn Trp Phe Asp Arg Asn Met Val Arg Phe Ile Met Trp Leu
    130                 135                 140

Gly Lys Gly Asp Thr Asp Val Thr Lys Pro Ile Ile Glu Tyr Thr Asp
145                 150                 155                 160

Trp Ala Lys Val Asp Gln Phe Ala Glu Leu Phe Tyr Thr Gln Thr Tyr
                165                 170                 175

Ser

<210> SEQ ID NO 19
<211> LENGTH: 174
<212> TYPE: PRT
<213> ORGANISM: Shewanella oneidensis

<400> SEQUENCE: 19

Met Gln Thr Leu Ile Ile Tyr Ser Thr Ile Asp Gly Gln Thr Leu Glu
1               5                   10                  15

Ile Cys Arg Lys Ile Lys Ala Phe Ala Glu Arg Ala Gly Glu Lys Val
            20                  25                  30

Ser Leu Phe Ser Leu Glu Gln Ala Glu Ala Ile Asn Leu Ala Asp Val
        35                  40                  45

Asp Lys Val Leu Ile Gly Ala Ser Ile Arg Tyr Gly Lys His Arg Pro
    50                  55                  60

Glu Leu Tyr Gln Phe Val Asn Arg Asn His Ala Val Leu Ser Ala Lys
65                  70                  75                  80

Val Asn Gly Phe Phe Thr Val Asn Val Val Ala Arg Lys Pro Leu Lys
                85                  90                  95

Asn Thr Pro Glu Thr Asn Pro Tyr Met Gln Lys Phe Leu Lys Leu Ser
            100                 105                 110

Leu Trp Gln Pro Gln His Leu Ala Val Phe Ala Gly Lys Ile Asp Tyr
        115                 120                 125

```
Pro Lys Tyr Gly Leu Phe Asp Arg Thr Met Ile Cys Phe Ile Met Trp
        130                 135                 140

Met Thr Lys Gly Pro Thr Asp Leu Lys Gly Thr Phe Glu Phe Thr Asp
145                 150                 155                 160

Trp Ala Lys Val Glu Ala Phe Gly Thr His Phe Ser Lys Leu
                165                 170

<210> SEQ ID NO 20
<211> LENGTH: 175
<212> TYPE: PRT
<213> ORGANISM: Shewanella benthica

<400> SEQUENCE: 20

Met Asn Lys Ile Leu Ile Ile Tyr Ser Ser Val His Gly Gln Thr Arg
1               5                   10                  15

Lys Ile Cys Glu Tyr Ile Ala Ser Gln Leu Arg Ala Ser Asp Tyr Gly
                20                  25                  30

Cys Glu Val Arg Leu Ala Ser Leu Glu Glu Gln Phe Asp Leu Asp Ser
            35                  40                  45

Phe Asp Lys Ile Ile Ile Gly Ala Ser Ile Arg His Gly Lys His Asn
50                  55                  60

Pro Glu Val Tyr His Phe Ile Asp Thr His Leu Val Ala Leu Glu Thr
65                  70                  75                  80

Lys Ser Ser Ser Phe Phe Ser Val Ser Leu Val Ala Arg Lys Ala Ser
                85                  90                  95

Arg Asn Thr Pro Glu Ser Asn Pro Tyr Met Gln Ala Phe Leu Ser Lys
                100                 105                 110

Thr Leu Trp Arg Pro Asn Leu Val Lys Val Phe Ala Gly Lys Leu Asp
            115                 120                 125

Tyr Gln Gly Tyr Asn Trp Leu Asp Arg Ser Ile Ile Arg Phe Ile Met
        130                 135                 140

Trp Ile Thr Lys Gly Pro Thr Ala Val Asn Thr Lys Ile Glu Tyr Thr
145                 150                 155                 160

Asp Trp Gln Leu Val Asp Val Phe Val Lys Glu Leu Glu Leu Leu
                165                 170                 175

<210> SEQ ID NO 21
<211> LENGTH: 176
<212> TYPE: PRT
<213> ORGANISM: Marinomonas ushuaiensis

<400> SEQUENCE: 21

Met Ser Thr Thr Leu Leu Ile Tyr Ser Thr Thr Asp Gly His Thr Lys
1               5                   10                  15

Lys Ile Ser Gln Lys Ile Gln Glu Ile Ile Glu Ala Lys Gly Gln Lys
                20                  25                  30

Val Thr Leu Leu Pro Ile Glu Glu Ile Thr Ala Ala Ala Leu Asp Ser
            35                  40                  45

His Asp Lys Ile Val Ile Gly Ala Ser Ile Arg Tyr Gly Lys His Gln
50                  55                  60

Lys Val Val Ala Asp Phe Ile Glu Gln Asn Lys Thr Thr Leu Glu Ser
65                  70                  75                  80

Lys Pro Ser Ala Phe Tyr Thr Val Asn Leu Val Ala Arg Lys Pro Glu
                85                  90                  95

Lys Cys Gln Pro Asp Thr Asn Pro Tyr Ile Ile Lys Phe Leu Ser Gln
                100                 105                 110
```

Leu Asp Trp Gln Pro Ser Leu Gln Gly Val Phe Ala Gly Lys Leu Asp
        115                 120                 125

Tyr Gln Lys Tyr Gly Phe Ile Asp Arg Asn Met Ile Arg Phe Ile Met
130                 135                 140

Trp Met Thr Lys Gly Pro Thr Asp Pro Lys Thr Asn Ile Glu Phe Thr
145                 150                 155                 160

Asn Trp Glu Ala Val Asp Gln Phe Ala Asn Gly Val Val Glu Leu Ser
                165                 170                 175

<210> SEQ ID NO 22
<211> LENGTH: 173
<212> TYPE: PRT
<213> ORGANISM: Shewanella woodyi

<400> SEQUENCE: 22

Met Ser Asn Ile Leu Ile Ile Tyr Ser Ser Val His Gly Gln Thr Arg
1               5                   10                  15

Lys Ile Cys Ala Tyr Leu Glu Asp Lys Phe Val Ala Leu Gly Asp Lys
                20                  25                  30

Val Thr Met Ser Ser Leu Asp Gln Val Pro Asp Leu Asn Asp Phe Asp
            35                  40                  45

Lys Val Val Leu Gly Ala Ser Ile Arg His Gly Lys His Asn Pro Asn
50                  55                  60

Val Tyr Asp Phe Ile Ser Gln Asn Arg Gly Ile Leu Glu Lys Lys Thr
65                  70                  75                  80

Ser Ser Phe Phe Ser Val Asn Leu Val Ala Arg Lys Pro Ala Lys Asn
                85                  90                  95

Thr Pro Gln Thr Asn Pro Tyr Met Leu Ala Phe Ile Glu Lys Ser Glu
            100                 105                 110

Trp Lys Pro Asn Leu Leu Gln Val Phe Ala Gly Ser Leu Asn Tyr Gln
        115                 120                 125

Gly Tyr Gly Ile Val Asp Arg Asn Ile Ile Arg Phe Ile Met Trp Met
130                 135                 140

Thr Lys Gly Pro Thr Asp Ala Gln Thr Asn Ile Glu Tyr Thr Asp Trp
145                 150                 155                 160

Ala Lys Val Asp Leu Phe Ser Ser Glu Phe His Ala Leu
                165                 170

<210> SEQ ID NO 23
<211> LENGTH: 176
<212> TYPE: PRT
<213> ORGANISM: Agarivorans albus

<400> SEQUENCE: 23

Met Lys Leu Leu Val Leu Tyr Ser Ser Cys Glu Gly Gln Thr Leu Lys
1               5                   10                  15

Ile Ala Lys His Ile Val Ser Gln Gln Ala Gly Glu Val Ala Ala Asp
                20                  25                  30

Tyr Ile Gln Ile Asp Ser Asn Gln Ser Leu Asp Leu Thr Ala Tyr
            35                  40                  45

Asp Lys Val Leu Ile Gly Ala Ser Ile Arg Tyr Gly Lys Phe Arg Pro
50                  55                  60

Gln Leu Tyr Ser Leu Leu Ala Glu Tyr Gln Asn Gln Leu Ala Asn Val
65                  70                  75                  80

Pro Val Ala Phe Phe Gly Val Cys Leu Thr Ala Arg Lys Pro Glu Lys
                85                  90                  95

```
Asn Thr Pro Glu Thr Ser Val Tyr Met Lys Lys Leu Asn Leu Asn Ala
                100                 105                 110

Ala Trp Met Pro Lys Leu Gln Ala Val Phe Ala Gly Ala Leu Leu Tyr
            115                 120                 125

Ser Lys Tyr Thr Trp Trp Gln Ala Leu Leu Ile Gln Phe Ile Met Lys
        130                 135                 140

Met Thr Gly Gly Ser Thr Asp Arg Ser Gln Asp Leu Glu Leu Thr Asp
145                 150                 155                 160

Trp Ala Lys Val Asp Glu Phe Ala Thr Gln Phe Ala Lys Leu Asp Lys
                165                 170                 175

<210> SEQ ID NO 24
<211> LENGTH: 179
<212> TYPE: PRT
<213> ORGANISM: Artificial Sequence
<220> FEATURE:
<223> OTHER INFORMATION: Recombinant

<400> SEQUENCE: 24

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Ala Ala Leu Arg Tyr Pro
            115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 25
<211> LENGTH: 179
<212> TYPE: PRT
<213> ORGANISM: Artificial Sequence
<220> FEATURE:
<223> OTHER INFORMATION: Recombinant

<400> SEQUENCE: 25

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45
```

```
Gln Val Leu Ile Gly Ala Ser Ile Arg Tyr Gly His Phe Asn Ala Val
     50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Arg Tyr Pro
                115                 120                 125

Arg Tyr Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 26
<211> LENGTH: 179
<212> TYPE: PRT
<213> ORGANISM: Artificial Sequence
<220> FEATURE:
<223> OTHER INFORMATION: Recombinant

<400> SEQUENCE: 26

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
                35                  40                  45

Gln Val Leu Ile Gly Ala Ser Ile Arg Tyr Gly His Phe Asn Ala Val
     50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Phe Arg Tyr Pro
                115                 120                 125

Arg Tyr Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 27
<211> LENGTH: 179
<212> TYPE: PRT
<213> ORGANISM: Artificial Sequence
<220> FEATURE:
<223> OTHER INFORMATION: Recombinant
```

<400> SEQUENCE: 27

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Ile Arg Tyr Pro
        115                 120                 125

Arg Tyr Arg Trp Ile Asp Lys Val Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 28
<211> LENGTH: 179
<212> TYPE: PRT
<213> ORGANISM: Artificial Sequence
<220> FEATURE:
<223> OTHER INFORMATION: Recombinant

<400> SEQUENCE: 28

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Val Arg Tyr Pro
        115                 120                 125

Arg Tyr Arg Trp Ile Asp Lys Val Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

```
<210> SEQ ID NO 29
<211> LENGTH: 179
<212> TYPE: PRT
<213> ORGANISM: Artificial Sequence
<220> FEATURE:
<223> OTHER INFORMATION: Recombinant

<400> SEQUENCE: 29
```

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Ala Tyr Pro
        115                 120                 125

Arg Tyr Arg Trp Ile Asp Lys Val Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

```
<210> SEQ ID NO 30
<211> LENGTH: 179
<212> TYPE: PRT
<213> ORGANISM: Artificial Sequence
<220> FEATURE:
<223> OTHER INFORMATION: Recombinant

<400> SEQUENCE: 30
```

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

```
Trp Gln Pro Ala Leu Cys Gly Val Phe Ala Gly Ala Leu Arg Ala Pro
            115                 120                 125

Arg Tyr Arg Trp Ile Asp Lys Val Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 31
<211> LENGTH: 179
<212> TYPE: PRT
<213> ORGANISM: Artificial Sequence
<220> FEATURE:
<223> OTHER INFORMATION: Recombinant

<400> SEQUENCE: 31

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg His Pro
            115                 120                 125

Arg Tyr Arg Trp Ile Asp Lys Val Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 32
<211> LENGTH: 179
<212> TYPE: PRT
<213> ORGANISM: Artificial Sequence
<220> FEATURE:
<223> OTHER INFORMATION: Recombinant

<400> SEQUENCE: 32

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
```

```
Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Met Pro
            115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 33
<211> LENGTH: 179
<212> TYPE: PRT
<213> ORGANISM: Artificial Sequence
<220> FEATURE:
<223> OTHER INFORMATION: Recombinant

<400> SEQUENCE: 33

Met Lys Ala Leu Val Leu Tyr Ser Thr Arg Asp Gly Gln Thr His Ala
 1               5                  10                  15

Ile Ala Ser Tyr Ile Ala Ser Cys Met Lys Glu Lys Ala Glu Cys Asp
                 20                  25                  30

Val Ile Asp Leu Thr His Gly His Val Asn Leu Thr Gln Tyr Asp
             35                  40                  45

Gln Val Leu Ile Gly Ala Ser Ile Arg Tyr Gly His Phe Asn Ala Val
         50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Trp Pro
            115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 34
<211> LENGTH: 179
<212> TYPE: PRT
<213> ORGANISM: Artificial Sequence
<220> FEATURE:
<223> OTHER INFORMATION: Recombinant

<400> SEQUENCE: 34
```

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Ala
            115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 35
<211> LENGTH: 179
<212> TYPE: PRT
<213> ORGANISM: Artificial Sequence
<220> FEATURE:
<223> OTHER INFORMATION: Recombinant

<400> SEQUENCE: 35

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Asp
            115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175
```

Lys Ala Leu

<210> SEQ ID NO 36
<211> LENGTH: 179
<212> TYPE: PRT
<213> ORGANISM: Artificial Sequence
<220> FEATURE:
<223> OTHER INFORMATION: Recombinant

<400> SEQUENCE: 36

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Glu
        115                 120                 125

Arg Tyr Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 37
<211> LENGTH: 179
<212> TYPE: PRT
<213> ORGANISM: Artificial Sequence
<220> FEATURE:
<223> OTHER INFORMATION: Recombinant

<400> SEQUENCE: 37

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Lys
```

```
            115                 120                 125
Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 38
<211> LENGTH: 179
<212> TYPE: PRT
<213> ORGANISM: Artificial Sequence
<220> FEATURE:
<223> OTHER INFORMATION: Recombinant

<400> SEQUENCE: 38

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Leu
        115                 120                 125

Arg Tyr Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 39
<211> LENGTH: 179
<212> TYPE: PRT
<213> ORGANISM: Artificial Sequence
<220> FEATURE:
<223> OTHER INFORMATION: Recombinant

<400> SEQUENCE: 39

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60
```

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Gln
            115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 40
<211> LENGTH: 179
<212> TYPE: PRT
<213> ORGANISM: Artificial Sequence
<220> FEATURE:
<223> OTHER INFORMATION: Recombinant

<400> SEQUENCE: 40

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Arg
            115                 120                 125

Arg Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 41
<211> LENGTH: 179
<212> TYPE: PRT
<213> ORGANISM: Artificial Sequence
<220> FEATURE:
<223> OTHER INFORMATION: Recombinant

<400> SEQUENCE: 41

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Ser
                115                 120                 125

Arg Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                    165                 170                 175

Lys Ala Leu
```

<210> SEQ ID NO 42
<211> LENGTH: 179
<212> TYPE: PRT
<213> ORGANISM: Artificial Sequence
<220> FEATURE:
<223> OTHER INFORMATION: Recombinant

<400> SEQUENCE: 42

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Thr
                115                 120                 125

Arg Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                    165                 170                 175

Lys Ala Leu
```

```
<210> SEQ ID NO 43
<211> LENGTH: 179
<212> TYPE: PRT
<213> ORGANISM: Artificial Sequence
<220> FEATURE:
<223> OTHER INFORMATION: Recombinant

<400> SEQUENCE: 43

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Ala Tyr Arg Trp Ile Asp Lys Val Met Ile Gln Leu Ile Met Arg Met
    130                 135                 140

Thr Gly Gly Glu Thr Asp Thr Ser Lys Glu Val Gly Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 44
<211> LENGTH: 179
<212> TYPE: PRT
<213> ORGANISM: Artificial Sequence
<220> FEATURE:
<223> OTHER INFORMATION: Recombinant

<400> SEQUENCE: 44

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125
```

```
Glu Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 45
<211> LENGTH: 179
<212> TYPE: PRT
<213> ORGANISM: Artificial Sequence
<220> FEATURE:
<223> OTHER INFORMATION: Recombinant

<400> SEQUENCE: 45

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Gly Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 46
<211> LENGTH: 179
<212> TYPE: PRT
<213> ORGANISM: Artificial Sequence
<220> FEATURE:
<223> OTHER INFORMATION: Recombinant

<400> SEQUENCE: 46

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60
```

```
Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

His Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 47
<211> LENGTH: 179
<212> TYPE: PRT
<213> ORGANISM: Artificial Sequence
<220> FEATURE:
<223> OTHER INFORMATION: Recombinant

<400> SEQUENCE: 47

Met Lys Ala Leu Val Leu Tyr Ser Thr Arg Asp Gly Gln Thr His Ala
  1               5                  10                  15

Ile Ala Ser Tyr Ile Ala Ser Cys Met Lys Glu Lys Ala Glu Cys Asp
             20                  25                  30

Val Ile Asp Leu Thr His Gly Glu His Val Asn Leu Thr Gln Tyr Asp
         35                  40                  45

Gln Val Leu Ile Gly Ala Ser Ile Arg Tyr Gly His Phe Asn Ala Val
     50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Ile Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 48
<211> LENGTH: 179
<212> TYPE: PRT
<213> ORGANISM: Artificial Sequence
<220> FEATURE:
<223> OTHER INFORMATION: Recombinant

<400> SEQUENCE: 48

Met Lys Ala Leu Val Leu Tyr Ser Thr Arg Asp Gly Gln Thr His Ala
```

```
             1               5                  10                 15
        Ile Ala Ser Tyr Ile Ala Ser Cys Met Lys Glu Lys Ala Glu Cys Asp
                         20                 25                 30

Val Ile Asp Leu Thr His Gly Glu His Val Asn Leu Thr Gln Tyr Asp
                         35                 40                 45

Gln Val Leu Ile Gly Ala Ser Ile Arg Tyr Gly His Phe Asn Ala Val
                     50                 55                 60

Leu Asp Lys Phe Ile Lys Arg Asn Val Asp Gln Leu Asn Asn Met Pro
         65                 70                 75                 80

Ser Ala Phe Phe Cys Val Asn Leu Thr Ala Arg Lys Pro Glu Lys Arg
                         85                 90                 95

Thr Pro Gln Thr Asn Pro Tyr Val Arg Lys Phe Leu Leu Ala Thr Pro
                        100                105                110

Trp Gln Pro Ala Leu Cys Gly Val Phe Ala Gly Ala Leu Arg Tyr Pro
                        115                120                125

Lys Tyr Arg Trp Ile Asp Lys Val Met Ile Gln Leu Ile Met Arg Met
                    130                135                140

Thr Gly Gly Glu Thr Asp Thr Ser Lys Glu Val Glu Tyr Thr Asp Trp
        145                150                155                160

Glu Gln Val Lys Lys Phe Ala Glu Asp Phe Ala Lys Leu Ser Tyr Lys
                        165                170                175

Lys Ala Leu

<210> SEQ ID NO 49
<211> LENGTH: 179
<212> TYPE: PRT
<213> ORGANISM: Artificial Sequence
<220> FEATURE:
<223> OTHER INFORMATION: Recombinant

<400> SEQUENCE: 49

Met Lys Ala Leu Val Leu Tyr Ser Thr Arg Asp Gly Gln Thr His Ala
         1               5                  10                 15

Ile Ala Ser Tyr Ile Ala Ser Cys Met Lys Glu Lys Ala Glu Cys Asp
                         20                 25                 30

Val Ile Asp Leu Thr His Gly Glu His Val Asn Leu Thr Gln Tyr Asp
                         35                 40                 45

Gln Val Leu Ile Gly Ala Ser Ile Arg Tyr Gly His Phe Asn Ala Val
                     50                 55                 60

Leu Asp Lys Phe Ile Lys Arg Asn Val Asp Gln Leu Asn Asn Met Pro
         65                 70                 75                 80

Ser Ala Phe Phe Cys Val Asn Leu Thr Ala Arg Lys Pro Glu Lys Arg
                         85                 90                 95

Thr Pro Gln Thr Asn Pro Tyr Val Arg Lys Phe Leu Leu Ala Thr Pro
                        100                105                110

Trp Gln Pro Ala Leu Cys Gly Val Phe Ala Gly Ala Leu Arg Tyr Pro
                        115                120                125

Leu Tyr Arg Trp Ile Asp Lys Val Met Ile Gln Leu Ile Met Arg Met
                    130                135                140

Thr Gly Gly Glu Thr Asp Thr Ser Lys Glu Val Glu Tyr Thr Asp Trp
        145                150                155                160

Glu Gln Val Lys Lys Phe Ala Glu Asp Phe Ala Lys Leu Ser Tyr Lys
                        165                170                175

Lys Ala Leu
```

```
<210> SEQ ID NO 50
<211> LENGTH: 179
<212> TYPE: PRT
<213> ORGANISM: Artificial Sequence
<220> FEATURE:
<223> OTHER INFORMATION: Recombinant

<400> SEQUENCE: 50

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Asn Tyr Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 51
<211> LENGTH: 179
<212> TYPE: PRT
<213> ORGANISM: Artificial Sequence
<220> FEATURE:
<223> OTHER INFORMATION: Recombinant

<400> SEQUENCE: 51

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125
```

```
Gln Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 52
<211> LENGTH: 179
<212> TYPE: PRT
<213> ORGANISM: Artificial Sequence
<220> FEATURE:
<223> OTHER INFORMATION: Recombinant

<400> SEQUENCE: 52

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Ser Tyr Arg Trp Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 53
<211> LENGTH: 179
<212> TYPE: PRT
<213> ORGANISM: Artificial Sequence
<220> FEATURE:
<223> OTHER INFORMATION: Recombinant

<400> SEQUENCE: 53

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
```

```
            65                  70                  75                  80
Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Ala Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 54
<211> LENGTH: 179
<212> TYPE: PRT
<213> ORGANISM: Artificial Sequence
<220> FEATURE:
<223> OTHER INFORMATION: Recombinant

<400> SEQUENCE: 54

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
                35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Cys Arg Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 55
<211> LENGTH: 179
<212> TYPE: PRT
<213> ORGANISM: Artificial Sequence
<220> FEATURE:
<223> OTHER INFORMATION: Recombinant

<400> SEQUENCE: 55

```
Met Lys Ala Leu Val Leu Tyr Ser Thr Arg Asp Gly Gln Thr His Ala
1               5                   10                  15
```

```
Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
         35                  40                  45

Gln Val Leu Ile Gly Ala Ser Ile Arg Tyr Gly His Phe Asn Ala Val
 50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Leu Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 56
<211> LENGTH: 179
<212> TYPE: PRT
<213> ORGANISM: Artificial Sequence
<220> FEATURE:
<223> OTHER INFORMATION: Recombinant

<400> SEQUENCE: 56

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
         35                  40                  45

Gln Val Leu Ile Gly Ala Ser Ile Arg Tyr Gly His Phe Asn Ala Val
 50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Trp Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

```
<210> SEQ ID NO 57
<211> LENGTH: 179
<212> TYPE: PRT
<213> ORGANISM: Artificial Sequence
<220> FEATURE:
<223> OTHER INFORMATION: Recombinant

<400> SEQUENCE: 57

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Ala Trp Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 58
<211> LENGTH: 179
<212> TYPE: PRT
<213> ORGANISM: Artificial Sequence
<220> FEATURE:
<223> OTHER INFORMATION: Recombinant

<400> SEQUENCE: 58

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Ala Ile Asp Lys Val Met Ile Gln Leu Ile Met Arg Met
```

```
                    130                 135                 140
Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 59
<211> LENGTH: 179
<212> TYPE: PRT
<213> ORGANISM: Artificial Sequence
<220> FEATURE:
<223> OTHER INFORMATION: Recombinant

<400> SEQUENCE: 59

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
                35                  40                  45

Gln Val Leu Ile Gly Ala Ser Ile Arg Tyr Gly His Phe Asn Ala Val
            50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Phe Ile Asp Lys Val Met Ile Gln Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 60
<211> LENGTH: 179
<212> TYPE: PRT
<213> ORGANISM: Artificial Sequence
<220> FEATURE:
<223> OTHER INFORMATION: Recombinant

<400> SEQUENCE: 60

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
                35                  40                  45

Gln Val Leu Ile Gly Ala Ser Ile Arg Tyr Gly His Phe Asn Ala Val
            50                  55                  60

Leu Asp Lys Phe Ile Lys Arg Asn Val Asp Gln Leu Asn Asn Met Pro
65                  70                  75                  80
```

```
Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Ile Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 61
<211> LENGTH: 179
<212> TYPE: PRT
<213> ORGANISM: Artificial Sequence
<220> FEATURE:
<223> OTHER INFORMATION: Recombinant

<400> SEQUENCE: 61

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Lys Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 62
<211> LENGTH: 179
<212> TYPE: PRT
<213> ORGANISM: Artificial Sequence
<220> FEATURE:
<223> OTHER INFORMATION: Recombinant

<400> SEQUENCE: 62

Met Lys Ala Leu Val Leu Tyr Ser Thr Arg Asp Gly Gln Thr His Ala
1               5                   10                  15
```

```
Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Leu Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 63
<211> LENGTH: 179
<212> TYPE: PRT
<213> ORGANISM: Artificial Sequence
<220> FEATURE:
<223> OTHER INFORMATION: Recombinant

<400> SEQUENCE: 63

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Pro Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 64
```

```
<211> LENGTH: 179
<212> TYPE: PRT
<213> ORGANISM: Artificial Sequence
<220> FEATURE:
<223> OTHER INFORMATION: Recombinant

<400> SEQUENCE: 64

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Arg Ile Asp Lys Val Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 65
<211> LENGTH: 179
<212> TYPE: PRT
<213> ORGANISM: Artificial Sequence
<220> FEATURE:
<223> OTHER INFORMATION: Recombinant

<400> SEQUENCE: 65

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Ser Ile Asp Lys Val Met Ile Gln Leu Ile Met Arg Met
130                 135                 140
```

-continued

Thr Gly Gly Glu Thr Asp Thr Ser Lys Glu Val Gly Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 66
<211> LENGTH: 179
<212> TYPE: PRT
<213> ORGANISM: Artificial Sequence
<220> FEATURE:
<223> OTHER INFORMATION: Recombinant

<400> SEQUENCE: 66

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Thr Ile Asp Lys Val Met Ile Gln Leu Ile Met Arg Met
        130                 135                 140

Thr Gly Gly Glu Thr Asp Thr Ser Lys Glu Val Gly Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 67
<211> LENGTH: 179
<212> TYPE: PRT
<213> ORGANISM: Artificial Sequence
<220> FEATURE:
<223> OTHER INFORMATION: Recombinant

<400> SEQUENCE: 67

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

```
Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Val Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 68
<211> LENGTH: 179
<212> TYPE: PRT
<213> ORGANISM: Artificial Sequence
<220> FEATURE:
<223> OTHER INFORMATION: Recombinant

<400> SEQUENCE: 68

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Tyr Ile Asp Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 69
<211> LENGTH: 179
<212> TYPE: PRT
<213> ORGANISM: Artificial Sequence
<220> FEATURE:
<223> OTHER INFORMATION: Recombinant

<400> SEQUENCE: 69

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
```

```
                20                  25                  30
Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ala Asp Lys Val Met Ile Gln Leu Ile Met Arg Met
                130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 70
<211> LENGTH: 179
<212> TYPE: PRT
<213> ORGANISM: Artificial Sequence
<220> FEATURE:
<223> OTHER INFORMATION: Recombinant

<400> SEQUENCE: 70

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Ala Lys Val Met Ile Gln Leu Ile Met Arg Met
                130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 71
<211> LENGTH: 179
```

<212> TYPE: PRT
<213> ORGANISM: Artificial Sequence
<220> FEATURE:
<223> OTHER INFORMATION: Recombinant

<400> SEQUENCE: 71

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Lys Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 72
<211> LENGTH: 179
<212> TYPE: PRT
<213> ORGANISM: Artificial Sequence
<220> FEATURE:
<223> OTHER INFORMATION: Recombinant

<400> SEQUENCE: 72

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asn Lys Val Met Ile Gln Leu Ile Met Arg Met
    130                 135                 140

```
Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 73
<211> LENGTH: 179
<212> TYPE: PRT
<213> ORGANISM: Artificial Sequence
<220> FEATURE:
<223> OTHER INFORMATION: Recombinant

<400> SEQUENCE: 73

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Gln Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 74
<211> LENGTH: 179
<212> TYPE: PRT
<213> ORGANISM: Artificial Sequence
<220> FEATURE:
<223> OTHER INFORMATION: Recombinant

<400> SEQUENCE: 74

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
```

85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Thr Lys Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 75
<211> LENGTH: 179
<212> TYPE: PRT
<213> ORGANISM: Artificial Sequence
<220> FEATURE:
<223> OTHER INFORMATION: Recombinant

<400> SEQUENCE: 75

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Asp Ala Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 76
<211> LENGTH: 179
<212> TYPE: PRT
<213> ORGANISM: Artificial Sequence
<220> FEATURE:
<223> OTHER INFORMATION: Recombinant

<400> SEQUENCE: 76

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

```
Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Gln Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 77
<211> LENGTH: 179
<212> TYPE: PRT
<213> ORGANISM: Artificial Sequence
<220> FEATURE:
<223> OTHER INFORMATION: Recombinant

<400> SEQUENCE: 77

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Arg Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 78
<211> LENGTH: 179
<212> TYPE: PRT
```

<213> ORGANISM: Artificial Sequence
<220> FEATURE:
<223> OTHER INFORMATION: Recombinant

<400> SEQUENCE: 78

| Met | Lys | Ala | Leu | Val | Leu | Tyr | Ser | Thr | Arg | Asp | Gly | Gln | Thr | His | Ala |
|---|---|---|---|---|---|---|---|---|---|---|---|---|---|---|---|
| 1 | | | | 5 | | | | | 10 | | | | | 15 | |

| Ile | Ala | Ser | Tyr | Ile | Ala | Ser | Cys | Met | Lys | Glu | Lys | Ala | Glu | Cys | Asp |
| | | | 20 | | | | | 25 | | | | | 30 | | |

| Val | Ile | Asp | Leu | Thr | His | Gly | Glu | His | Val | Asn | Leu | Thr | Gln | Tyr | Asp |
| | | 35 | | | | | 40 | | | | | 45 | | | |

| Gln | Val | Leu | Ile | Gly | Ala | Ser | Ile | Arg | Tyr | Gly | His | Phe | Asn | Ala | Val |
| | 50 | | | | | 55 | | | | | 60 | | | | |

| Leu | Asp | Lys | Phe | Ile | Lys | Arg | Asn | Val | Asp | Gln | Leu | Asn | Asn | Met | Pro |
| 65 | | | | | 70 | | | | | 75 | | | | | 80 |

| Ser | Ala | Phe | Phe | Cys | Val | Asn | Leu | Thr | Ala | Arg | Lys | Pro | Glu | Lys | Arg |
| | | | | 85 | | | | | 90 | | | | | 95 | |

| Thr | Pro | Gln | Thr | Asn | Pro | Tyr | Val | Arg | Lys | Phe | Leu | Leu | Ala | Thr | Pro |
| | | | | 100 | | | | | 105 | | | | | 110 | |

| Trp | Gln | Pro | Ala | Leu | Cys | Gly | Val | Phe | Ala | Gly | Ala | Leu | Arg | Tyr | Pro |
| | | | | 115 | | | | | 120 | | | | | 125 | |

| Arg | Tyr | Arg | Trp | Ile | Asp | Ser | Val | Met | Ile | Gln | Leu | Ile | Met | Arg | Met |
| | | 130 | | | | | 135 | | | | | 140 | | | |

| Thr | Gly | Gly | Glu | Thr | Asp | Thr | Ser | Lys | Glu | Val | Glu | Tyr | Thr | Asp | Trp |
| 145 | | | | | 150 | | | | | 155 | | | | | 160 |

| Glu | Gln | Val | Lys | Lys | Phe | Ala | Glu | Asp | Phe | Ala | Lys | Leu | Ser | Tyr | Lys |
| | | | | 165 | | | | | 170 | | | | | 175 | |

Lys Ala Leu

<210> SEQ ID NO 79
<211> LENGTH: 179
<212> TYPE: PRT
<213> ORGANISM: Artificial Sequence
<220> FEATURE:
<223> OTHER INFORMATION: Recombinant

<400> SEQUENCE: 79

| Met | Lys | Ala | Leu | Val | Leu | Tyr | Ser | Thr | Arg | Asp | Gly | Gln | Thr | His | Ala |
|---|---|---|---|---|---|---|---|---|---|---|---|---|---|---|---|
| 1 | | | | 5 | | | | | 10 | | | | | 15 | |

| Ile | Ala | Ser | Tyr | Ile | Ala | Ser | Cys | Met | Lys | Glu | Lys | Ala | Glu | Cys | Asp |
| | | | 20 | | | | | 25 | | | | | 30 | | |

| Val | Ile | Asp | Leu | Thr | His | Gly | Glu | His | Val | Asn | Leu | Thr | Gln | Tyr | Asp |
| | | 35 | | | | | 40 | | | | | 45 | | | |

| Gln | Val | Leu | Ile | Gly | Ala | Ser | Ile | Arg | Tyr | Gly | His | Phe | Asn | Ala | Val |
| | 50 | | | | | 55 | | | | | 60 | | | | |

| Leu | Asp | Lys | Phe | Ile | Lys | Arg | Asn | Val | Asp | Gln | Leu | Asn | Asn | Met | Pro |
| 65 | | | | | 70 | | | | | 75 | | | | | 80 |

| Ser | Ala | Phe | Phe | Cys | Val | Asn | Leu | Thr | Ala | Arg | Lys | Pro | Glu | Lys | Arg |
| | | | | 85 | | | | | 90 | | | | | 95 | |

| Thr | Pro | Gln | Thr | Asn | Pro | Tyr | Val | Arg | Lys | Phe | Leu | Leu | Ala | Thr | Pro |
| | | | | 100 | | | | | 105 | | | | | 110 | |

| Trp | Gln | Pro | Ala | Leu | Cys | Gly | Val | Phe | Ala | Gly | Ala | Leu | Arg | Tyr | Pro |
| | | | | 115 | | | | | 120 | | | | | 125 | |

| Arg | Tyr | Arg | Trp | Ile | Asp | Thr | Val | Met | Ile | Gln | Leu | Ile | Met | Arg | Met |
| | | 130 | | | | | 135 | | | | | 140 | | | |

| Thr | Gly | Gly | Glu | Thr | Asp | Thr | Ser | Lys | Glu | Val | Glu | Tyr | Thr | Asp | Trp |

```
                145                 150                 155                 160
Glu Gln Val Lys Lys Phe Ala Glu Asp Phe Ala Lys Leu Ser Tyr Lys
                    165                 170                 175

Lys Ala Leu

<210> SEQ ID NO 80
<211> LENGTH: 179
<212> TYPE: PRT
<213> ORGANISM: Artificial Sequence
<220> FEATURE:
<223> OTHER INFORMATION: Recombinant

<400> SEQUENCE: 80

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Asp Val Val Met Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                    165                 170                 175

Lys Ala Leu

<210> SEQ ID NO 81
<211> LENGTH: 179
<212> TYPE: PRT
<213> ORGANISM: Artificial Sequence
<220> FEATURE:
<223> OTHER INFORMATION: Recombinant

<400> SEQUENCE: 81

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95
```

```
Thr Pro Gln Thr Asn Pro Tyr Val Arg Lys Phe Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Ala Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 82
<211> LENGTH: 179
<212> TYPE: PRT
<213> ORGANISM: Artificial Sequence
<220> FEATURE:
<223> OTHER INFORMATION: Recombinant

<400> SEQUENCE: 82

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Ala Ile Gln Leu Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 83
<211> LENGTH: 179
<212> TYPE: PRT
<213> ORGANISM: Artificial Sequence
<220> FEATURE:
<223> OTHER INFORMATION: Recombinant

<400> SEQUENCE: 83

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30
```

```
Val Ile Asp Leu Thr His Gly Glu His Val Asn Leu Thr Gln Tyr Asp
         35                  40                  45

Gln Val Leu Ile Gly Ala Ser Ile Arg Tyr Gly His Phe Asn Ala Val
 50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Cys Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 84
<211> LENGTH: 179
<212> TYPE: PRT
<213> ORGANISM: Artificial Sequence
<220> FEATURE:
<223> OTHER INFORMATION: Recombinant

<400> SEQUENCE: 84

```
Met Lys Ala Leu Val Leu Tyr Ser Thr Arg Asp Gly Gln Thr His Ala
 1               5                  10                  15

Ile Ala Ser Tyr Ile Ala Ser Cys Met Lys Glu Lys Ala Glu Cys Asp
                 20                  25                  30

Val Ile Asp Leu Thr His Gly Glu His Val Asn Leu Thr Gln Tyr Asp
         35                  40                  45

Gln Val Leu Ile Gly Ala Ser Ile Arg Tyr Gly His Phe Asn Ala Val
 50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Ile Ile Gln Leu Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 85
<211> LENGTH: 179
<212> TYPE: PRT
<213> ORGANISM: Artificial Sequence

```
<220> FEATURE:
<223> OTHER INFORMATION: Recombinant

<400> SEQUENCE: 85

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Leu Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 86
<211> LENGTH: 179
<212> TYPE: PRT
<213> ORGANISM: Artificial Sequence
<220> FEATURE:
<223> OTHER INFORMATION: Recombinant

<400> SEQUENCE: 86

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Ser Ile Gln Leu Ile Met Arg Met
    130                 135                 140

Thr Gly Gly Glu Thr Asp Thr Ser Lys Glu Val Glu Tyr Thr Asp Trp
145                 150                 155                 160
```

Glu Gln Val Lys Lys Phe Ala Glu Asp Phe Ala Lys Leu Ser Tyr Lys
        165                 170                 175

Lys Ala Leu

<210> SEQ ID NO 87
<211> LENGTH: 179
<212> TYPE: PRT
<213> ORGANISM: Artificial Sequence
<220> FEATURE:
<223> OTHER INFORMATION: Recombinant

<400> SEQUENCE: 87

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Val Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 88
<211> LENGTH: 179
<212> TYPE: PRT
<213> ORGANISM: Artificial Sequence
<220> FEATURE:
<223> OTHER INFORMATION: Recombinant

<400> SEQUENCE: 88

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ala Gln Leu Ile Met Arg Met
130                 135                 140

Thr Gly Gly Glu Thr Asp Thr Ser Lys Glu Val Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 89
<211> LENGTH: 179
<212> TYPE: PRT
<213> ORGANISM: Artificial Sequence
<220> FEATURE:
<223> OTHER INFORMATION: Recombinant

<400> SEQUENCE: 89

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Leu Gln Leu Ile Met Arg Met
130                 135                 140

Thr Gly Gly Glu Thr Asp Thr Ser Lys Glu Val Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 90
<211> LENGTH: 179
<212> TYPE: PRT
<213> ORGANISM: Artificial Sequence
<220> FEATURE:
<223> OTHER INFORMATION: Recombinant

<400> SEQUENCE: 90

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp

```
            35                  40                  45
Gln Val Leu Ile Gly Ala Ser Ile Arg Tyr Gly His Phe Asn Ala Val
         50                  55                  60
Leu Asp Lys Phe Ile Lys Arg Asn Val Asp Gln Leu Asn Asn Met Pro
 65                  70                  75                  80
Ser Ala Phe Phe Cys Val Asn Leu Thr Ala Arg Lys Pro Glu Lys Arg
                 85                  90                  95
Thr Pro Gln Thr Asn Pro Tyr Val Arg Lys Phe Leu Leu Ala Thr Pro
            100                 105                 110
Trp Gln Pro Ala Leu Cys Gly Val Phe Ala Gly Ala Leu Arg Tyr Pro
            115                 120                 125
Arg Tyr Arg Trp Ile Asp Lys Val Met Met Gln Leu Ile Met Arg Met
            130                 135                 140
Thr Gly Gly Glu Thr Asp Thr Ser Lys Glu Val Glu Tyr Thr Asp Trp
145                 150                 155                 160
Glu Gln Val Lys Lys Phe Ala Glu Asp Phe Ala Lys Leu Ser Tyr Lys
                165                 170                 175
Lys Ala Leu

<210> SEQ ID NO 91
<211> LENGTH: 179
<212> TYPE: PRT
<213> ORGANISM: Artificial Sequence
<220> FEATURE:
<223> OTHER INFORMATION: Recombinant

<400> SEQUENCE: 91

Met Lys Ala Leu Val Leu Tyr Ser Thr Arg Asp Gly Gln Thr His Ala
 1               5                  10                  15
Ile Ala Ser Tyr Ile Ala Ser Cys Met Lys Glu Lys Ala Glu Cys Asp
                 20                  25                  30
Val Ile Asp Leu Thr His Gly Glu His Val Asn Leu Thr Gln Tyr Asp
            35                  40                  45
Gln Val Leu Ile Gly Ala Ser Ile Arg Tyr Gly His Phe Asn Ala Val
         50                  55                  60
Leu Asp Lys Phe Ile Lys Arg Asn Val Asp Gln Leu Asn Asn Met Pro
 65                  70                  75                  80
Ser Ala Phe Phe Cys Val Asn Leu Thr Ala Arg Lys Pro Glu Lys Arg
                 85                  90                  95
Thr Pro Gln Thr Asn Pro Tyr Val Arg Lys Phe Leu Leu Ala Thr Pro
            100                 105                 110
Trp Gln Pro Ala Leu Cys Gly Val Phe Ala Gly Ala Leu Arg Tyr Pro
            115                 120                 125
Arg Tyr Arg Trp Ile Asp Lys Val Met Val Gln Leu Ile Met Arg Met
            130                 135                 140
Thr Gly Gly Glu Thr Asp Thr Ser Lys Glu Val Glu Tyr Thr Asp Trp
145                 150                 155                 160
Glu Gln Val Lys Lys Phe Ala Glu Asp Phe Ala Lys Leu Ser Tyr Lys
                165                 170                 175
Lys Ala Leu

<210> SEQ ID NO 92
<211> LENGTH: 179
<212> TYPE: PRT
<213> ORGANISM: Artificial Sequence
<220> FEATURE:
```

<223> OTHER INFORMATION: Recombinant

<400> SEQUENCE: 92

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Ala Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 93
<211> LENGTH: 179
<212> TYPE: PRT
<213> ORGANISM: Artificial Sequence
<220> FEATURE:
<223> OTHER INFORMATION: Recombinant

<400> SEQUENCE: 93

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Cys Ile Met Arg Met
    130                 135                 140

Thr Gly Gly Glu Thr Asp Thr Ser Lys Glu Val Glu Tyr Thr Asp Trp
145                 150                 155                 160
```

```
        Glu Gln Val Lys Lys Phe Ala Glu Asp Phe Ala Lys Leu Ser Tyr Lys
                        165                 170                 175

Lys Ala Leu

<210> SEQ ID NO 94
<211> LENGTH: 179
<212> TYPE: PRT
<213> ORGANISM: Artificial Sequence
<220> FEATURE:
<223> OTHER INFORMATION: Recombinant

<400> SEQUENCE: 94

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Phe Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 95
<211> LENGTH: 179
<212> TYPE: PRT
<213> ORGANISM: Artificial Sequence
<220> FEATURE:
<223> OTHER INFORMATION: Recombinant

<400> SEQUENCE: 95

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
```

```
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Gly Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 96
<211> LENGTH: 179
<212> TYPE: PRT
<213> ORGANISM: Artificial Sequence
<220> FEATURE:
<223> OTHER INFORMATION: Recombinant

<400> SEQUENCE: 96

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln His Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 97
<211> LENGTH: 179
<212> TYPE: PRT
<213> ORGANISM: Artificial Sequence
<220> FEATURE:
<223> OTHER INFORMATION: Recombinant

<400> SEQUENCE: 97

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45
```

```
Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Ile Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 98
<211> LENGTH: 179
<212> TYPE: PRT
<213> ORGANISM: Artificial Sequence
<220> FEATURE:
<223> OTHER INFORMATION: Recombinant

<400> SEQUENCE: 98

Met Lys Ala Leu Val Leu Tyr Ser Thr Arg Asp Gly Gln Thr His Ala
 1               5                  10                  15

Ile Ala Ser Tyr Ile Ala Ser Cys Met Lys Glu Lys Ala Glu Cys Asp
                 20                  25                  30

Val Ile Asp Leu Thr His Gly Glu His Val Asn Leu Thr Gln Tyr Asp
             35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Lys Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 99
<211> LENGTH: 179
<212> TYPE: PRT
<213> ORGANISM: Artificial Sequence
<220> FEATURE:
<223> OTHER INFORMATION: Recombinant
```

<400> SEQUENCE: 99

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Met Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 100
<211> LENGTH: 179
<212> TYPE: PRT
<213> ORGANISM: Artificial Sequence
<220> FEATURE:
<223> OTHER INFORMATION: Recombinant

<400> SEQUENCE: 100

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Arg Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys

```
                165                 170                 175

Lys Ala Leu

<210> SEQ ID NO 101
<211> LENGTH: 179
<212> TYPE: PRT
<213> ORGANISM: Artificial Sequence
<220> FEATURE:
<223> OTHER INFORMATION: Recombinant

<400> SEQUENCE: 101

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Thr Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 102
<211> LENGTH: 179
<212> TYPE: PRT
<213> ORGANISM: Artificial Sequence
<220> FEATURE:
<223> OTHER INFORMATION: Recombinant

<400> SEQUENCE: 102

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110
```

```
Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Ala Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
            165                 170                 175

Lys Ala Leu

<210> SEQ ID NO 103
<211> LENGTH: 179
<212> TYPE: PRT
<213> ORGANISM: Artificial Sequence
<220> FEATURE:
<223> OTHER INFORMATION: Recombinant

<400> SEQUENCE: 103

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Leu Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
            165                 170                 175

Lys Ala Leu

<210> SEQ ID NO 104
<211> LENGTH: 179
<212> TYPE: PRT
<213> ORGANISM: Artificial Sequence
<220> FEATURE:
<223> OTHER INFORMATION: Recombinant

<400> SEQUENCE: 104

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45
```

```
Gln Val Leu Ile Gly Ala Ser Ile Arg Tyr Gly His Phe Asn Ala Val
     50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Leu Met Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 105
<211> LENGTH: 179
<212> TYPE: PRT
<213> ORGANISM: Artificial Sequence
<220> FEATURE:
<223> OTHER INFORMATION: Recombinant

<400> SEQUENCE: 105

Met Lys Ala Leu Val Leu Tyr Ser Thr Arg Asp Gly Gln Thr His Ala
 1               5                  10                  15

Ile Ala Ser Tyr Ile Ala Ser Cys Met Lys Glu Lys Ala Glu Cys Asp
                 20                  25                  30

Val Ile Asp Leu Thr His Gly Glu His Val Asn Leu Thr Gln Tyr Asp
                 35                  40                  45

Gln Val Leu Ile Gly Ala Ser Ile Arg Tyr Gly His Phe Asn Ala Val
     50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Leu Val Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 106
<211> LENGTH: 179
<212> TYPE: PRT
<213> ORGANISM: Artificial Sequence
<220> FEATURE:
<223> OTHER INFORMATION: Recombinant
```

<400> SEQUENCE: 106

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Ala Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 107
<211> LENGTH: 179
<212> TYPE: PRT
<213> ORGANISM: Artificial Sequence
<220> FEATURE:
<223> OTHER INFORMATION: Recombinant

<400> SEQUENCE: 107

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Asp Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 108
<211> LENGTH: 179
<212> TYPE: PRT
<213> ORGANISM: Artificial Sequence
<220> FEATURE:
<223> OTHER INFORMATION: Recombinant

<400> SEQUENCE: 108

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Leu Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175
```

Lys Ala Leu

<210> SEQ ID NO 109
<211> LENGTH: 179
<212> TYPE: PRT
<213> ORGANISM: Artificial Sequence
<220> FEATURE:
<223> OTHER INFORMATION: Recombinant

<400> SEQUENCE: 109

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110
```

```
Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Ile Ser Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 110
<211> LENGTH: 179
<212> TYPE: PRT
<213> ORGANISM: Artificial Sequence
<220> FEATURE:
<223> OTHER INFORMATION: Recombinant

<400> SEQUENCE: 110

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Ile Val Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 111
<211> LENGTH: 179
<212> TYPE: PRT
<213> ORGANISM: Artificial Sequence
<220> FEATURE:
<223> OTHER INFORMATION: Recombinant

<400> SEQUENCE: 111

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
```

```
                    50                  55                  60
Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                     85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Leu Ile Met Ala Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                    165                 170                 175

Lys Ala Leu

<210> SEQ ID NO 112
<211> LENGTH: 179
<212> TYPE: PRT
<213> ORGANISM: Artificial Sequence
<220> FEATURE:
<223> OTHER INFORMATION: Recombinant

<400> SEQUENCE: 112

Met Lys Ala Leu Val Leu Tyr Ser Thr Arg Asp Gly Gln Thr His Ala
  1               5                  10                  15

Ile Ala Ser Tyr Ile Ala Ser Cys Met Lys Glu Lys Ala Glu Cys Asp
                 20                  25                  30

Val Ile Asp Leu Thr His Gly Glu His Val Asn Leu Thr Gln Tyr Asp
             35                  40                  45

Gln Val Leu Ile Gly Ala Ser Ile Arg Tyr Gly His Phe Asn Ala Val
         50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                     85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Leu Ile Met Arg Ala
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                    165                 170                 175

Lys Ala Leu

<210> SEQ ID NO 113
<211> LENGTH: 179
<212> TYPE: PRT
<213> ORGANISM: Artificial Sequence
<220> FEATURE:
<223> OTHER INFORMATION: Recombinant

<400> SEQUENCE: 113
```

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Leu Ile Met Arg Met
            130                 135                 140

Ala Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 114
<211> LENGTH: 179
<212> TYPE: PRT
<213> ORGANISM: Artificial Sequence
<220> FEATURE:
<223> OTHER INFORMATION: Recombinant

<400> SEQUENCE: 114

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Leu Ile Met Arg Met
            130                 135                 140

Thr Ala Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175
```

Lys Ala Leu

<210> SEQ ID NO 115
<211> LENGTH: 179
<212> TYPE: PRT
<213> ORGANISM: Artificial Sequence
<220> FEATURE:
<223> OTHER INFORMATION: Recombinant

<400> SEQUENCE: 115

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Met Arg Met
130                 135                 140

Thr Asp Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 116
<211> LENGTH: 179
<212> TYPE: PRT
<213> ORGANISM: Artificial Sequence
<220> FEATURE:
<223> OTHER INFORMATION: Recombinant

<400> SEQUENCE: 116

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro

```
                115                 120                 125
Arg Tyr Arg Trp Ile Asp Lys Val Met Ile Gln Leu Ile Met Arg Met
        130                 135                 140

Thr His Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 117
<211> LENGTH: 179
<212> TYPE: PRT
<213> ORGANISM: Artificial Sequence
<220> FEATURE:
<223> OTHER INFORMATION: Recombinant

<400> SEQUENCE: 117

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Met Arg Met
        130                 135                 140

Thr Lys Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 118
<211> LENGTH: 179
<212> TYPE: PRT
<213> ORGANISM: Artificial Sequence
<220> FEATURE:
<223> OTHER INFORMATION: Recombinant

<400> SEQUENCE: 118

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
    50                  55                  60
```

```
Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Ile Met Arg Met
        130                 135                 140

Thr Asn Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 119
<211> LENGTH: 179
<212> TYPE: PRT
<213> ORGANISM: Artificial Sequence
<220> FEATURE:
<223> OTHER INFORMATION: Recombinant

<400> SEQUENCE: 119

Met Lys Ala Leu Val Leu Tyr Ser Thr Arg Asp Gly Gln Thr His Ala
  1               5                  10                  15

Ile Ala Ser Tyr Ile Ala Ser Cys Met Lys Glu Lys Ala Glu Cys Asp
                 20                  25                  30

Val Ile Asp Leu Thr His Gly Glu His Val Asn Leu Thr Gln Tyr Asp
             35                  40                  45

Gln Val Leu Ile Gly Ala Ser Ile Arg Tyr Gly His Phe Asn Ala Val
         50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Ile Met Arg Met
        130                 135                 140

Thr Gly Ala Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 120
<211> LENGTH: 179
<212> TYPE: PRT
<213> ORGANISM: Artificial Sequence
<220> FEATURE:
<223> OTHER INFORMATION: Recombinant

<400> SEQUENCE: 120
```

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Ile Met Arg Met
        130                 135                 140

Thr Gly Lys Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 121
<211> LENGTH: 179
<212> TYPE: PRT
<213> ORGANISM: Artificial Sequence
<220> FEATURE:
<223> OTHER INFORMATION: Recombinant

<400> SEQUENCE: 121

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Leu Ile Met Arg Met
        130                 135                 140

Thr Gly Met Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 122
<211> LENGTH: 179
<212> TYPE: PRT
<213> ORGANISM: Artificial Sequence
<220> FEATURE:
<223> OTHER INFORMATION: Recombinant

<400> SEQUENCE: 122

| Met | Lys | Ala | Leu | Val | Leu | Tyr | Ser | Thr | Arg | Asp | Gly | Gln | Thr | His | Ala |
|---|---|---|---|---|---|---|---|---|---|---|---|---|---|---|---|
| 1 | | | | 5 | | | | | 10 | | | | | 15 | |

| Ile | Ala | Ser | Tyr | Ile | Ala | Ser | Cys | Met | Lys | Glu | Lys | Ala | Glu | Cys | Asp |
|---|---|---|---|---|---|---|---|---|---|---|---|---|---|---|---|
| | | | 20 | | | | | 25 | | | | | 30 | | |

| Val | Ile | Asp | Leu | Thr | His | Gly | Glu | His | Val | Asn | Leu | Thr | Gln | Tyr | Asp |
|---|---|---|---|---|---|---|---|---|---|---|---|---|---|---|---|
| | | | 35 | | | | | 40 | | | | | 45 | | |

| Gln | Val | Leu | Ile | Gly | Ala | Ser | Ile | Arg | Tyr | Gly | His | Phe | Asn | Ala | Val |
|---|---|---|---|---|---|---|---|---|---|---|---|---|---|---|---|
| | | 50 | | | | | 55 | | | | | 60 | | | |

| Leu | Asp | Lys | Phe | Ile | Lys | Arg | Asn | Val | Asp | Gln | Leu | Asn | Asn | Met | Pro |
|---|---|---|---|---|---|---|---|---|---|---|---|---|---|---|---|
| 65 | | | | | 70 | | | | | 75 | | | | | 80 |

| Ser | Ala | Phe | Phe | Cys | Val | Asn | Leu | Thr | Ala | Arg | Lys | Pro | Glu | Lys | Arg |
|---|---|---|---|---|---|---|---|---|---|---|---|---|---|---|---|
| | | | | 85 | | | | | 90 | | | | | 95 | |

| Thr | Pro | Gln | Thr | Asn | Pro | Tyr | Val | Arg | Lys | Phe | Leu | Leu | Ala | Thr | Pro |
|---|---|---|---|---|---|---|---|---|---|---|---|---|---|---|---|
| | | | 100 | | | | | 105 | | | | | 110 | | |

| Trp | Gln | Pro | Ala | Leu | Cys | Gly | Val | Phe | Ala | Gly | Ala | Leu | Arg | Tyr | Pro |
|---|---|---|---|---|---|---|---|---|---|---|---|---|---|---|---|
| | | | 115 | | | | | 120 | | | | | 125 | | |

| Arg | Tyr | Arg | Trp | Ile | Asp | Lys | Val | Met | Ile | Gln | Leu | Ile | Met | Arg | Met |
|---|---|---|---|---|---|---|---|---|---|---|---|---|---|---|---|
| | 130 | | | | | 135 | | | | | 140 | | | | |

| Thr | Gly | Arg | Glu | Thr | Asp | Thr | Ser | Lys | Glu | Val | Gly | Tyr | Thr | Asp | Trp |
|---|---|---|---|---|---|---|---|---|---|---|---|---|---|---|---|
| 145 | | | | | 150 | | | | | 155 | | | | | 160 |

| Glu | Gln | Val | Lys | Lys | Phe | Ala | Glu | Asp | Phe | Ala | Lys | Leu | Ser | Tyr | Lys |
|---|---|---|---|---|---|---|---|---|---|---|---|---|---|---|---|
| | | | | 165 | | | | | 170 | | | | | 175 | |

| Lys | Ala | Leu |
|---|---|---|

<210> SEQ ID NO 123
<211> LENGTH: 179
<212> TYPE: PRT
<213> ORGANISM: Artificial Sequence
<220> FEATURE:
<223> OTHER INFORMATION: Recombinant

<400> SEQUENCE: 123

| Met | Lys | Ala | Leu | Val | Leu | Tyr | Ser | Thr | Arg | Asp | Gly | Gln | Thr | His | Ala |
|---|---|---|---|---|---|---|---|---|---|---|---|---|---|---|---|
| 1 | | | | 5 | | | | | 10 | | | | | 15 | |

| Ile | Ala | Ser | Tyr | Ile | Ala | Ser | Cys | Met | Lys | Glu | Lys | Ala | Glu | Cys | Asp |
|---|---|---|---|---|---|---|---|---|---|---|---|---|---|---|---|
| | | | 20 | | | | | 25 | | | | | 30 | | |

| Val | Ile | Asp | Leu | Thr | His | Gly | Glu | His | Val | Asn | Leu | Thr | Gln | Tyr | Asp |
|---|---|---|---|---|---|---|---|---|---|---|---|---|---|---|---|
| | | | 35 | | | | | 40 | | | | | 45 | | |

| Gln | Val | Leu | Ile | Gly | Ala | Ser | Ile | Arg | Tyr | Gly | His | Phe | Asn | Ala | Val |
|---|---|---|---|---|---|---|---|---|---|---|---|---|---|---|---|
| | | 50 | | | | | 55 | | | | | 60 | | | |

| Leu | Asp | Lys | Phe | Ile | Lys | Arg | Asn | Val | Asp | Gln | Leu | Asn | Asn | Met | Pro |
|---|---|---|---|---|---|---|---|---|---|---|---|---|---|---|---|
| 65 | | | | | 70 | | | | | 75 | | | | | 80 |

| Ser | Ala | Phe | Phe | Cys | Val | Asn | Leu | Thr | Ala | Arg | Lys | Pro | Glu | Lys | Arg |
|---|---|---|---|---|---|---|---|---|---|---|---|---|---|---|---|
| | | | | 85 | | | | | 90 | | | | | 95 | |

| Thr | Pro | Gln | Thr | Asn | Pro | Tyr | Val | Arg | Lys | Phe | Leu | Leu | Ala | Thr | Pro |
|---|---|---|---|---|---|---|---|---|---|---|---|---|---|---|---|
| | | | 100 | | | | | 105 | | | | | 110 | | |

| Trp | Gln | Pro | Ala | Leu | Cys | Gly | Val | Phe | Ala | Gly | Ala | Leu | Arg | Tyr | Pro |
|---|---|---|---|---|---|---|---|---|---|---|---|---|---|---|---|
| | | | 115 | | | | | 120 | | | | | 125 | | |

```
Arg Tyr Arg Trp Ile Asp Lys Val Met Ile Gln Leu Ile Met Arg Met
            130                 135                 140

Thr Gly Ser Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 124
<211> LENGTH: 179
<212> TYPE: PRT
<213> ORGANISM: Artificial Sequence
<220> FEATURE:
<223> OTHER INFORMATION: Recombinant

<400> SEQUENCE: 124

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Ala Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 125
<211> LENGTH: 540
<212> TYPE: DNA
<213> ORGANISM: Enterobacter cloacae

<400> SEQUENCE: 125
atgaaggcct tggtactgta ctcgacgcgg gacggccaga cccacgcaat tgcttcatac      60
atcgcctcct gcatgaagga aaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct accccctggc agcccgcgtt gtgcggagtg     360
ttcgcagggg cccttcggta cccgcgatac cggtggatcg acaaggtgat gatccagcta     420
```

```
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 126
<211> LENGTH: 546
<212> TYPE: DNA
<213> ORGANISM: Escherichia coli

<400> SEQUENCE: 126

```
atgaagacct tgattctatt ctccacaagg gacggccaga ctagggagat cgcttcctac     60
ctggccagcg agctaaagga gcttggcatt caggcagacg tggctaacgt gcaccgaatt    120
gaggagccgc agtgggagaa ctacgatcgg gtcgtgatcg gcgccagcat ccggtatgga    180
cactaccaca gcgcgttcca ggagttcgtg aaaaagcacg cgacccgtct gaatagcatg    240
ccatcagcgt tctactcggt caacctcgtg gctcgtaagc ccgagaagcg gacacccag     300 accaactcgt atgccaggaa gttccttatg aactcgcagt ggcgaccgga ccgctgcgcg    360
gtgatcgccg gtgcgctcag gtaccctcgt tataggtggg acgacaggtt tatgattaaa    420
cttataatga aaatgagcgg cggagagacc gacaccagaa agaggtggt ttacacagac     480 tgggagcagg tagcaaactt cgctagggag attgctcacc tcaccgacaa gccgaccttg    540
aagtaa                                                              546
```

<210> SEQ ID NO 127
<211> LENGTH: 537
<212> TYPE: DNA
<213> ORGANISM: Pantoea ananatis

<400> SEQUENCE: 127

```
atgaaggcct tgatcctgtt ctctacacgc gacggacaga cacagaagat cgcatctgcc     60
atcgctgatg agataaaggg gcagcaatcg tgcgacgtga ttaacataca ggatgccaaa    120
accctcgact ggcagcagta cgaccgggta ctcatcggcg cctccattcg ttacgggcat    180
ttccagcccg ttgtgaatga gtttgtcaag cacaacctct ggccctaca gcagagagtt     240 tccggattct ctccgtgaa cttgacagcc cgaaagccag agaagcggag ccccgagact     300
aacgcttata cagtcaaatt cttggcgcag tcaccctggc aaccggactg ctgcgctgtt    360 tttgcgggg ccctgtacta cccacgggtac cggtggttcg ataggtgat gatacagttc    420 ataatgcgaa tgacgggggg agagaccgac gcatcgaaag aggtggagta cactgactgg    480
cagcaggtgc agcggttcgc gcgagacttc gcgcagttac cgggtaagtc ctactga      537
```

<210> SEQ ID NO 128
<211> LENGTH: 537
<212> TYPE: DNA
<213> ORGANISM: Erwinia toletana

<400> SEQUENCE: 128

```
atgaaggccc ttatactgtt cagttccaga gaaggccaga cgagggagat agcgagttac     60
attgccaact cgataaagga ggaaatggaa tgcgacgtgt tcaacatcct tcgtgtggag    120
cagatcgact ggtctcaata cgaccgcgtc ctgatcgggg ctcgatacac ctacggccat    180
ttccacccag cggtggcaaa atttgtcaag aggcacctcc atgagttgca acagaggtct    240
tccggctttt tctgcgtcaa cctgacggcc aggaaggccg acaagcggac tcccagacc     300 aatgcctaca tgaaaagtt cttgttgcag tccccatggc aacccgattg ctgcgccgtg    360
tttgcggggg cccttaggta cacccgttac aggtggttcg acagggtaat gattcagctg    420
```

```
atcatgagga tgacgggcgg agagactgac acatcgaagg aggtggagta cacagactgg    480
acgcaggtcg cccgcttcgc gcaggagttc gcccatttgc ccggcaaaac tcagtga       537
```

<210> SEQ ID NO 129
<211> LENGTH: 540
<212> TYPE: DNA
<213> ORGANISM: Pectobacterium carotovorum

<400> SEQUENCE: 129

```
atgaaggctc ttatcgtatt ctcttcgagg gatggccaaa cccgagcgat cgcgtcttat    60
attgctaata ccctcaaagg daccctagag tgcgacgtcg tcaacgtcct caatgctaac    120
gacattgatt tgagccagta cgaccgtgtg gccattggcg cctccattcg ctacgggagg    180
ttccacccag ctgttaacca gtttatccgg aagcaccta cgagcctcca gcagctacca    240
tctgcgttct ctccgtgaa cctcacagct cggaagcccg agaagaggac tatacaaacc    300
aacgcgtaca ctaggaagtt tctactgaac tcgccgtggc agccggacct gtgctgcgtg    360
ttcgcgggag cccttcgcta tccccgttac aggtggtttg accgagtgat gattcaactc    420
ataatgcgca taacgggggg cgagacagac tccaccaagg agatcgagta caccgactgg    480
cagcaggtcg cgcgattcgc ccaggatttt gcacagcttg ccgcaaagaa cccggcatga   540
```

<210> SEQ ID NO 130
<211> LENGTH: 540
<212> TYPE: DNA
<213> ORGANISM: Shimwellia blattae

<400> SEQUENCE: 130

```
atgaagacct tgatcctatt ctccaccagg gacggccaaa cacacaagat cgcaaggcac    60
atcgcaggag tcctcgaaga gcaggggaag gcctgcgagt tggtcgatct gttacagccc   120
ggcgaaccag actggagtac cgttgaatgc gtcgttctag ggccagcat tagatatggt    180 cacttccata agtctttcat caggttcgta aacactcacg cgcagcgctt gaataatatg    240
ccaggcgccc ttttcacagt taacttagtc gcccgaaagc ccgagaagca gagtccacag    300
acgaactctt acacccgcaa gtttctcgcc gcctccccctt ggcagccaca gcgatgccaa    360
gttttcgcgg gcgctttgag gtaccctagg tactcgtggt acgacagaat gatgatacgt    420 tgataatga agatggccgg gggcgagact gacacaagga aggaggttga gtacactgac    480
tggcagtcgg tgactcggtt cgcgagggag atcgctcagc tgccgggaga gacgcggtag    540
```

<210> SEQ ID NO 131
<211> LENGTH: 534
<212> TYPE: DNA
<213> ORGANISM: Pantoea stewardii

<400> SEQUENCE: 131

```
atgaaggcgc tgatcttgta ctcaaccagg gacggtcaga ctcgcaagat tgcaagtagc    60
attgcggacg tcatcaggca gcagcagcag tgcgacgtct taaacattaa agacgcatca    120
cttcctgact gggcccaata tgaccgagtg ctcatcggag ctagcatccg ttacgggcat    180
ttccagcccg ttgtagacaa gttcgtgaag cagcacttgc acgagcttca gcagcggacc    240
tccggcttct ctccgtgaa cctgacggcg aggaagcctg aaaaaggag ccctgagacc    300 aatgcctaca cccagaaatt cttggcgcac tccccttggc agcccgattg ctgtgccgtt    360
ttcgcggggg ccctttacta ccccaggtac cgttggttcg accgggtgat gatccagttg    420
```
attatgcgca tgactggtgg agagaccgac tctaccaagg aagtggagta cactgactgg    480
cagcaggtga gtaccttcgc caacgatttt gcccagcttc caggcaagag ctaa          534

<210> SEQ ID NO 132
<211> LENGTH: 537
<212> TYPE: DNA
<213> ORGANISM: Pantoea stewardii

<400> SEQUENCE: 132
atgaaggccc taattttatt cagtagtagg gacggccaga cccagcttat agcatcgtct    60
atcgccaagg agctcgaagg gaagcaggcg tgcgacgtgt tgaatatcct cgacacgact    120
aatgtggagt ggacccagta cgaccgcgtg ctgattggag catccatccg gtacgggcac    180
tttcaccctg cggtcgccga gttcgtaaag cgtcaccagc gagagctaca gcagagaagt    240
agtggctttt tctctgtgaa cttgacggcc cgtaagccgg aaaagaggtc ccccgagact    300
aacgcctata ccgccaagtt ccttaaccaa agtccatggc agcctgactg ttgcgctgtg    360
ttcgctgggg ctttgcgata ccctcggtac cgctggttcg acagaattat gatccagcta    420
atcatgcgga tgactggggg tgagacagat tcttcaaagg aggtcgagta caccgactgg    480
cagcaggtga cccgcttcgc gcaagagttc gccaggcttc cgggaaagac cagttga       537

<210> SEQ ID NO 133
<211> LENGTH: 543
<212> TYPE: DNA
<213> ORGANISM: Enterobacter cloacae

<400> SEQUENCE: 133
atgaagaccc taatactgtt ctctacccgc gacgggcaga caagggagat cgccgcgttc    60
cttgcctcgg agctgaagga gcaggggatt tacgctgacg tcataaacct taaccggacg    120
gaggagatag cttggcagga gtatgataga gtcgtaatcg gggcgtcgat ccgatacggg    180
catttccacc ctgctgtcga ccgcttcgtg aagaagcaca cagagacact caactcactg    240
cccggcgcct ttttctctgt aaaccttgtt gcccggaaag ccgagaagag aacgccgcag    300
acgaactcat acaccaggaa gttcctatta aacagcccgt ggaagccagc ggcctgcgcg    360
gtctttgctg ggccctccg ctaccctaga taccgctggt acgacaggtt catgatacga    420
ctgattatga aaatgacagg cggggagacg gatacccgaa aggaggtagt ctacactgac    480
tggtcgcagg tcgcgtcgtt tgccagagag atagtccagt tgaccaggtc atcgcgcttg    540
tga                                                                 543

<210> SEQ ID NO 134
<211> LENGTH: 534
<212> TYPE: DNA
<213> ORGANISM: Enterobacter mori

<400> SEQUENCE: 134
atgaagatat taatccttt ctccacccgt gacggccaaa cccgtgagat tgcggcgtcc    60
ttggcgtccg aactcaagga gcaggcattc gacgtggacg tcgtcaacct tcaccgggcc    120
gagaacatcg catgggagga gtacgacggt gttgtcatcg gagcgtccat caggtacggc    180
cactttcata gtaccctgaa ctcatttgtc aagaagcatc agcaggctct taagaagctt    240
cccggggctt tctacagcgt gaacctcgtc gcccggaagc ctgagaagcg cacaccgcag    300
accaatagct acacccgcaa gttcctcttg gattccccgt ggcagcccga cctttcagcc    360
gtgttcgccg gggcactcag gtaccctcgg tacaattggt acgaccgtat catgattaga    420

```
cttatcatga agattacagg cggcgagact gataccagga aggaagtagt ctacacagac   480
tggcagcagt tcactcactt tgctcacgag atcgtccagc tcgtgcggaa gtag         534
```

<210> SEQ ID NO 135
<211> LENGTH: 540
<212> TYPE: DNA
<213> ORGANISM: ahnella aquatilis

<400> SEQUENCE: 135

```
atgaaggctc ttatcctcta ctctagcaga gacggacaga cacacgccat tgcctcctac   60
atcgcaaatg aactcaagga gaagtgctcc tgcgatgtcg tggacctggc gcacgctgag  120
cgggttgatc tgaagtcata cgaccaggtc atgattggcg cttccatacg ctacggacac  180
ttcaatcccg ttctcgacaa gtttgtgaag aagcacgccg ggatcttaaa ccacatgcca  240
tctgccttct tcggcgtgaa cttaacagcc cggaagcccg agaagcgtac accacagacg  300
aacgcctacg tccgcaagtt cttgctcgca tcaccctggg agcccgcaat gtgcggcgtg  360
ttcgctggtg ccctgcgata cccgcgctac cgctggttcg acaaggtcat gattcagctc  420
atcatgcgga tgacaggagg cgaaacggac actaggaagg aagtagagta caccgactgg  480
caacaagtgg ccaaattcgc agaggacttc gggcagatta gctacaagaa gtctcattag  540
```

<210> SEQ ID NO 136
<211> LENGTH: 546
<212> TYPE: DNA
<213> ORGANISM: Salmonella enterica subsp enterica serovar

<400> SEQUENCE: 136

```
atgaagacgc tcattctctt ctcgacgcgg gacgggcaaa ctcgggaaat cgcgtcatac   60
ctggcgtccg agctcaagga gatgggcatc tgggccgatg tcgtgaacct ccacagagcg  120
gaggagcccg attgggactc ctacgacagg gttgtcatag gtgcctcgat ccgctacgga  180
cattatcact ccgcttttcca ggagttcgtt aagaagtacg ccacgcgatt gaacggtatg  240
ccaagtgcct tctactcggt gaatcttgtt gcacggaagg ccgagaagcg aactccacag  300
accaacagct acgcacggaa attcctcatg tcaagtcctt ggagacctga ttattgcgcc  360
gtgattgcgg gtgccttgcg ttaccctcgc tatcgctggt acgaccgact catgatcaaa  420
cttatcatga agatgtctgg cggcgagacc gacacgagca aggaggtggt gtacactgat  480
tgggaacaag tggcgcactt cgcacgagag attgcacacc ttacgaacaa gtcctcggcc  540
aaatag                                                              546
```

<210> SEQ ID NO 137
<211> LENGTH: 540
<212> TYPE: DNA
<213> ORGANISM: Rahnella aquatilis

<400> SEQUENCE: 137

```
atgaaggccc tcatcttgta ctccagccgc gacgggcaaa cccatgctat cgcctcttac   60
attgcgaacg agcttaagga gaagtgttcc tgcgatgtcg tggacctcgc ccacgcggaa  120
agagtggacc tcaagtcgta tgaccaagtg atgatcggcg cttccatccg atacggccac  180
ttcaatccag tgctcgacaa gttcgttaag aagcacgcgg agactcttaa ccgtatgccc  240
tcagccttct tcggagtcaa cttgaccgct aggaaacctg agaagcgcac gccgcagacc  300
aatgcttacg tgaggaagtt cctccttgca agcccttggg agccagccat gtgcggtgtg  360
```

```
ttcgctggtg ccctccgcta cccacgctac cgttggtttg acaaggtcat gattcagttg    420
attatgagaa tgacaggcgg tgagacagac acacgcaagg aagtcgagta caccgattgg    480
cagcaagtgg ctaagttcgc agaggacttc ggtcagatca gctacaagaa atctcattga    540
```

<210> SEQ ID NO 138
<211> LENGTH: 528
<212> TYPE: DNA
<213> ORGANISM: Vibrio pacinii

<400> SEQUENCE: 138

```
atggcaaagg cactcttcct ctactctacc cgcgagggcc agaccaagaa gatcttccag     60
cacatctccg agcagatgaa ggagttcgat tgcgagatga tcgacctgca ctccgtcgag    120
tccgtggact ctcccagta ccaacgggta ctcatcggcg catccatccg atacggccac    180
cttaacaaga aactctatca attcatcgag cacaatctga gccagttgca gaccgctaag    240
tcggcgttct tctgcgtgaa cctcactgct cgaaaggagg accaggcgaa ggatactcct    300
gagggctcgg cctacatcaa gacgttctta tccaagtcgc cttggcagcc ggaactaata    360
ggcgtgttcg ctggtgccct gtactaccct cgctacaact ggttcgacaa gacgatgatt    420
aagttcatca tgtccatgac gggcggcgag accgacacct ccaaggaggt ggagtacact    480
aactggggca aggtgacctt gttcgcagac aagttccaga acctctag                 528
```

<210> SEQ ID NO 139
<211> LENGTH: 525
<212> TYPE: DNA
<213> ORGANISM: Xenorhabdus nematophila

<400> SEQUENCE: 139

```
atgtcctacc tgctcttgta cagcacccag gatggtcaga ccaagaagat catcatgcgt     60
attgccgaga acctccgccg ctctggtgtt tcgtgcgacc tgagagactt ggccgcagtg    120
aagcaagtga acttagcgag ctaccagaag gtgatggtcg gtgcctcgat ccggtacggc    180
cacttcaact ccgttctgca caagttcgtg acccaccacc agaagcagct gaaccagaag    240
ccgacggcct tcttcggagt caaccctcaca gcaaggaagc cggagaagcg cactccggag    300
actaacgcct acgttcgcaa gttcctcatg aagtcgccct ggcagcctga cctttgtgag    360
gtcttcgctg cgctctcct gtacccgcgt tacaagtggc tcgaccgtgt gatgatccag    420
attattatgc ggatgactgg tggcgagacc gataccacca aggagatcga gtacaccgat    480
tgggcacaag tcgatcggtt cagtgagatg ttccttcaga tttga                    525
```

<210> SEQ ID NO 140
<211> LENGTH: 525
<212> TYPE: DNA
<213> ORGANISM: Vibrio diazotrophicus

<400> SEQUENCE: 140

```
atgaaggcac tcctcttgta ctccacccgc gagggccaga ccaagaagat tatgcaccac     60
atcgcccagc agctccaggg ctatgaatgc cagttcgtgg acctccacga gtgccacact    120
atggacttga ctcaatacga taaggtctta attggtgcct ccattcgtta cgggaagctc    180
aacgcaaagc tgtaccaatt catcgacgcc cacatcaagc agctcgaaca agttaaggcc    240
gccttctatt gcgtcaacct caccgcacgc aaggtggaac agggcaagga tactcccgaa    300
gggtcagtgt acatcaagac gttcctcaag aagtcgccct ggcagccgag cctgatcggc    360
gtgttcgccg gtgcattgta ctatccgcgc taccgtccaa tcgaccgcat gatgataagg    420
```

```
ttcatcatga agctcacagg cggcgaaact gataccacca aggaggtcga gtacaccgac    480
tgggagaagg tctcactgtt cgcaaagaag ttcgagcagt tgtga                    525

<210> SEQ ID NO 141
<211> LENGTH: 525
<212> TYPE: DNA
<213> ORGANISM: Grimontia hollisae

<400> SEQUENCE: 141
atgaagaagg ccctcctcct gcattcttcg cgcgagggcc agacacttaa gatcctcagg    60
gccatcgagt cagaactaag cgagtcatac cagtgcgagc ttgtggacct gcacgagatg    120
ccagaggtga actgggaaga ttacgataag gtgcttatcg gtgcctccat cagatacggc    180
cacttgaaca agaagctgta ccgtttcatc gagactaacc tctcgtccct caagaacaag    240
aaggccgcgt tcttctgcgt gaacttgacc gcgaggaagc ccggcaagga cacgccggag    300
ggctcggtgt acatgaagaa attcctcaag cgttcgccgt ggcagccgca gctccttgat    360
gtgttcgctg cgctctgta ctacccacgc taccgattct tcgaccgtgt gatgatccag    420
ttcattatga agatgactgg tggagagacc gacccaacta aggaaatcga gtacaccaac    480
tgggacaggg tgaaggtctt ctcaggccaa tttcggtcgt tgtga                   525

<210> SEQ ID NO 142
<211> LENGTH: 534
<212> TYPE: DNA
<213> ORGANISM: Gilliamella apicola

<400> SEQUENCE: 142
atgaaggtgc tcttgcttta caccactcac gagaagcaga cctttaagat catgcagcgc    60
atcgagaacc agctcgccgg gaagtgcgac tgcgacgtca ttgaactcct tccctctacg    120
aacatcgacc ttacgaagta ccaggccgtc ctcctcgggt gctccattcg ctacggcttc    180
tactctaagg tgatgaagaa gttcatcgac aacaactacc agcagttgaa caagatgagg    240
tccggcttct tcggcgtaaa cgtggtggca cgcaagccgc acaagaacac gccggagacc    300
aacagttaca cgcgcaagtt cctggccaag atcgcgtggc agcctaccat caaggcggtg    360
ttcgcgggcg ctctttacta cccaaagtac aactggttcg accggaacat ggtgaggttc    420
atcatgtggc ttgggaaggg cgacaccgac gtcaccaagc caattattga gtacacggac    480
tgggccaagg tggaccagtt cgcagaactg ttctacacgc agacgtactc gtga          534

<210> SEQ ID NO 143
<211> LENGTH: 525
<212> TYPE: DNA
<213> ORGANISM: Shewanella oneidensis

<400> SEQUENCE: 143
atgcagaccc tcatcatcta ctccacaata gacggtcaga cacttgaaat ctgccgtaag    60
atcaaagcgt tcgccgagcg cgctggcgag aaggtgtccc tgttctcact ggaacaggct    120
gaggccatca acctggcgga cgttgataag gttctcatcg gcgcatccat ccgctatggc    180
aagcaccgtc ccgagctgta ccaattcgtc aaccgcaacc acgccgtact atcagccaaa    240
gtcaacggct tcttcaccgt gaatgtggtg gcgaggaagc cattgaagaa cactccggag    300
accaaccctt acatgcagaa gttcctcaag ttgtcgctct ggcagcctca acaccttgca    360
gtgttcgccg ggaagataga ctacccgaag tacgggctat tcgaccgaac catgatctgc    420
```

| | |
|---|---|
| ttcatcatgt ggatgaccaa agggccgacg gacctgaaag gcaccttcga gttcacagac | 480 |
| tgggccaagg tcgaggcttt cgggacacac ttctccaagt tgtga | 525 |

<210> SEQ ID NO 144
<211> LENGTH: 528
<212> TYPE: DNA
<213> ORGANISM: Shewanella benthica

<400> SEQUENCE: 144

| | |
|---|---|
| atgaacaaga ttctcatcat ctactctagc gtccacgggc agaccaggaa gatttgcgag | 60 |
| tacatcgcca gtcagctcag ggcgtccgat tatgggtgcg aggtccgact ggcctcgctg | 120 |
| gaggaacagt tcgatctgga ctcattcgac aagatcatca tcggtgcctc catccgccac | 180 |
| ggcaagcaca acccggaggt gtaccacttc atcgacactc accttgtggc acttgagacg | 240 |
| aagtccagct cgttcttctc cgtgtcccta gtcgcccgca aggcaagtcg caacacgccg | 300 |
| gagtcaaacc cgtacatgca agcgtttctg tccaagactc tgtggagacc aaacctggtc | 360 |
| aaggtgttcg ccggaaagct cgactaccag ggctacaact ggcttgatcg cagcatcata | 420 |
| aggtttatca tgtggatcac gaagggccct acggccgtga acactaagat cgagtacacc | 480 |
| gactggcaac ttgtggatgt gttcgtgaag gaattggagc tgctttag | 528 |

<210> SEQ ID NO 145
<211> LENGTH: 531
<212> TYPE: DNA
<213> ORGANISM: Marinomonas ushuaiensis

<400> SEQUENCE: 145

| | |
|---|---|
| atgtccacca ccctcctgat ctactcgact acagacgggc atacgaagaa gatttcccag | 60 |
| aagatccagg agatcatcga ggcgaagggc cagaaggtca cccttcttcc catcgaggag | 120 |
| attacggcgg cggccctaga ctcccacgat aagatcgtga tcggcgcgtc catccgctac | 180 |
| ggcaagcacc agaaggtcgt ggcggacttc attgagcaga acaagactac tctggagtca | 240 |
| aagccgtccg ccttctacac cgtcaacctg gtggcccgca agcctgagaa gtgccagccc | 300 |
| gacacgaacc cttacatcat caaattcttg tcacagctcg actggcagcc ctcccttcaa | 360 |
| ggagtcttcg ctggcaaact cgactaccag aagtacggct tcattgacag aaacatgata | 420 |
| cggttcatca tgtggatgac caaaggccct accgacccaa agacgaacat cgagttcact | 480 |
| aactgggagg cggttgacca gttcgccaac ggcgttgtgg agcttagctg a | 531 |

<210> SEQ ID NO 146
<211> LENGTH: 522
<212> TYPE: DNA
<213> ORGANISM: Shewanella woodyi

<400> SEQUENCE: 146

| | |
|---|---|
| atgagcaaca tccttattat ctactccagt gtgcacggcc agacgcggaa gatttgcgct | 60 |
| tacttggagg acaagttcgt tgcccttggc gacaaggtga ccatgtcgtc cctcgaccaa | 120 |
| gtgcccgacc tcaacgactt cgacaaggtg gtactcggtg ccagcatccg acacgggaag | 180 |
| cacaacccga acgtttacga cttcatcagt cagaatcgtg catcctcga gaagaagacc | 240 |
| agctcattct tcagcgtcaa cctcgtggca aggaagcctg caaagaacac tccacagacg | 300 |
| aatccctaca tgcttgcctt catcgagaag tccgagtgga gcccaacttg cttcaagtg | 360 |
| ttcgcgggct cgctaaacta ccagggttac ggcatagtgg accgtaacat tatccggttc | 420 |
| atcatgtgga tgactaaggg accgacggac gcccagacca acattgagta cactgattgg | 480 |

```
gctaaagttg atctgtttag ttccgagttc cacgcgctgt ag               522
```

<210> SEQ ID NO 147
<211> LENGTH: 531
<212> TYPE: DNA
<213> ORGANISM: Agarivorans albus

<400> SEQUENCE: 147

```
atgaagttgc tcgtgcttta ctcatcctgt gagggacaga ctctcaagat cgctaagcac    60
atcgtctctc aacaggccgg agaagtggcg gccgactaca ttcagatcga ctccaaccag   120
cagtcactgg acctcaccgc ttacgacaag gtcttaatcg gcgcgtccat cagatacggg   180
aagttccgac cgcagctcta ctccctactg gctgagtacc agaaccagct cgcaaacgtc   240
cctgtggcct tcttcggcgt ttgcctcaca gcgcgaaagc ccgagaagaa tacgccggag   300
actagcgtgt acatgaagaa gctgaacttg aacgccgctt ggatgcctaa gctccaggct   360
gtgttcgctg agccctctt gtacagtaag tacacctggt ggcaagccct gctcatacag   420
ttcatcatga agatgacggg cgggagcact gaccgctcac aagacctgga actcacagat   480
tgggccaagg tggatgagtt cgccactcag ttcgccaagt ggacaagta g             531
```

<210> SEQ ID NO 148
<211> LENGTH: 540
<212> TYPE: DNA
<213> ORGANISM: Artificial Sequence
<220> FEATURE:
<223> OTHER INFORMATION: Recombinant

<400> SEQUENCE: 148

```
atgaaggcct tggtactgta ctcgacgcgg gacggccaga cccacgcaat tgcttcatac    60
atcgcctcct gcatgaagga aaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagctg cccttcggta cccgcgatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 149
<211> LENGTH: 540
<212> TYPE: DNA
<213> ORGANISM: Artificial Sequence
<220> FEATURE:
<223> OTHER INFORMATION: Recombinant

<400> SEQUENCE: 149

```
atgaaggcct tggtactgta ctcgacgcgg gacggccaga cccacgcaat tgcttcatac    60
atcgcctcct gcatgaagga aaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
``` ttcgcaggggg ccgctcggta cccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 150
<211> LENGTH: 540
<212> TYPE: DNA
<213> ORGANISM: Artificial Sequence
<220> FEATURE:
<223> OTHER INFORMATION: Recombinant

<400> SEQUENCE: 150
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccttccggta cccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 151
<211> LENGTH: 540
<212> TYPE: DNA
<213> ORGANISM: Artificial Sequence
<220> FEATURE:
<223> OTHER INFORMATION: Recombinant

<400> SEQUENCE: 151
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccatacggta cccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 152
<211> LENGTH: 540
<212> TYPE: DNA
<213> ORGANISM: Artificial Sequence
<220> FEATURE:
<223> OTHER INFORMATION: Recombinant

<400> SEQUENCE: 152
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240

```
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccgtccggta cccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 153
<211> LENGTH: 540
<212> TYPE: DNA
<213> ORGANISM: Artificial Sequence
<220> FEATURE:
<223> OTHER INFORMATION: Recombinant

<400> SEQUENCE: 153

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttgctta cccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 154
<211> LENGTH: 540
<212> TYPE: DNA
<213> ORGANISM: Artificial Sequence
<220> FEATURE:
<223> OTHER INFORMATION: Recombinant

<400> SEQUENCE: 154

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcgggc tccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 155
<211> LENGTH: 540
<212> TYPE: DNA
<213> ORGANISM: Artificial Sequence
<220> FEATURE:
<223> OTHER INFORMATION: Recombinant

<400> SEQUENCE: 155

```
atgaaggcct tggtactgta ctcgacgcgg gacggccaga cccacgcaat tgcttcatac     60
```

```
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggca tccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 156
<211> LENGTH: 540
<212> TYPE: DNA
<213> ORGANISM: Artificial Sequence
<220> FEATURE:
<223> OTHER INFORMATION: Recombinant

<400> SEQUENCE: 156

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggat gccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 157
<211> LENGTH: 540
<212> TYPE: DNA
<213> ORGANISM: Artificial Sequence
<220> FEATURE:
<223> OTHER INFORMATION: Recombinant

<400> SEQUENCE: 157

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggtg gccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 158
<211> LENGTH: 540
<212> TYPE: DNA
<213> ORGANISM: Artificial Sequence
<220> FEATURE:
<223> OTHER INFORMATION: Recombinant

<400> SEQUENCE: 158

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg cccttcggta cgctcgatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 159
<211> LENGTH: 540
<212> TYPE: DNA
<213> ORGANISM: Artificial Sequence
<220> FEATURE:
<223> OTHER INFORMATION: Recombinant

<400> SEQUENCE: 159

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg cccttcggta cgatcgatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 160
<211> LENGTH: 540
<212> TYPE: DNA
<213> ORGANISM: Artificial Sequence
<220> FEATURE:
<223> OTHER INFORMATION: Recombinant

<400> SEQUENCE: 160

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg cccttcggta cgaacgatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 161

```
<211> LENGTH: 540
<212> TYPE: DNA
<213> ORGANISM: Artificial Sequence
<220> FEATURE:
<223> OTHER INFORMATION: Recombinant

<400> SEQUENCE: 161
atgaaggcct tggtactgta ctcgacgcgg gacggccaga cccacgcaat tgcttcatac    60
atcgcctcct gcatgaagga aaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg cccttcggta caaacgatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540

<210> SEQ ID NO 162
<211> LENGTH: 540
<212> TYPE: DNA
<213> ORGANISM: Artificial Sequence
<220> FEATURE:
<223> OTHER INFORMATION: Recombinant

<400> SEQUENCE: 162
atgaaggcct tggtactgta ctcgacgcgg gacggccaga cccacgcaat tgcttcatac    60
atcgcctcct gcatgaagga aaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg cccttcggta cctacgatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540

<210> SEQ ID NO 163
<211> LENGTH: 540
<212> TYPE: DNA
<213> ORGANISM: Artificial Sequence
<220> FEATURE:
<223> OTHER INFORMATION: Recombinant

<400> SEQUENCE: 163
atgaaggcct tggtactgta ctcgacgcgg gacggccaga cccacgcaat tgcttcatac    60
atcgcctcct gcatgaagga aaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg cccttcggta ccaacgatac cggtggatcg acaaggtgat gatccagcta   420
ataatgcgga tgactggggg agagacagac acgagcaagg aggtcgagta cacggattgg   480
```
gagcaggtta agaagttcgc ggaggatttt gcaaagctat cgtacaagaa ggccctctag    540

<210> SEQ ID NO 164
<211> LENGTH: 540
<212> TYPE: DNA
<213> ORGANISM: Artificial Sequence
<220> FEATURE:
<223> OTHER INFORMATION: Recombinant

<400> SEQUENCE: 164
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta ccggcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 165
<211> LENGTH: 540
<212> TYPE: DNA
<213> ORGANISM: Artificial Sequence
<220> FEATURE:
<223> OTHER INFORMATION: Recombinant

<400> SEQUENCE: 165
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta ctctcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 166
<211> LENGTH: 540
<212> TYPE: DNA
<213> ORGANISM: Artificial Sequence
<220> FEATURE:
<223> OTHER INFORMATION: Recombinant

<400> SEQUENCE: 166
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300

```
aacccttatg tccgaaaatt cttgcttgct accccctggc agcccgcgtt gtgcggagtg    360
ttcgcagggg cccttcggta cactcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 167
<211> LENGTH: 540
<212> TYPE: DNA
<213> ORGANISM: Artificial Sequence
<220> FEATURE:
<223> OTHER INFORMATION: Recombinant

<400> SEQUENCE: 167

```
atgaaggcct tggtactgta ctcgacgcgg gacggccaga cccacgcaat tgcttcatac     60
atcgcctcct gcatgaagga aaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccggcttac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 168
<211> LENGTH: 540
<212> TYPE: DNA
<213> ORGANISM: Artificial Sequence
<220> FEATURE:
<223> OTHER INFORMATION: Recombinant

<400> SEQUENCE: 168

```
atgaaggcct tggtactgta ctcgacgcgg gacggccaga cccacgcaat tgcttcatac     60
atcgcctcct gcatgaagga aaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccggaatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 169
<211> LENGTH: 540
<212> TYPE: DNA
<213> ORGANISM: Artificial Sequence
<220> FEATURE:
<223> OTHER INFORMATION: Recombinant

<400> SEQUENCE: 169

```
atgaaggcct tggtactgta ctcgacgcgg gacggccaga cccacgcaat tgcttcatac     60
atcgcctcct gcatgaagga aaggccgaa tgcgacgtga tcgacctcac ccacggggag    120
cacgtgaacc tcacccaata cgatcaggtg ctaatcggtg cgagtattcg ttacggccac    180
```

```
ttcaacgccg tgcttgacaa gttcatcaag agaaacgtgg atcagctgaa caacatgcca      240
agcgcgttct tctgcgtaaa cctcacagca aggaagcccg agaagcgtac tccccagaca      300
aacccttatg tccgaaaatt cttgcttgct accccctggc agcccgcgtt gtgcggagtg      360
ttcgcagggg cccttcggta cccgggctac cggtggatcg acaaggtgat gatccagcta      420
ataatgcgga tgactggggg agagacagac acgagcaagg aggtcgagta cacggattgg      480
gagcaggtta agaagttcgc ggaggatttt gcaaagctat cgtacaagaa ggccctctag      540
```

<210> SEQ ID NO 170
<211> LENGTH: 540
<212> TYPE: DNA
<213> ORGANISM: Artificial Sequence
<220> FEATURE:
<223> OTHER INFORMATION: Recombinant

<400> SEQUENCE: 170

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcattac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 171
<211> LENGTH: 540
<212> TYPE: DNA
<213> ORGANISM: Artificial Sequence
<220> FEATURE:
<223> OTHER INFORMATION: Recombinant

<400> SEQUENCE: 171

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgatatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 172
<211> LENGTH: 540
<212> TYPE: DNA
<213> ORGANISM: Artificial Sequence
<220> FEATURE:
<223> OTHER INFORMATION: Recombinant

<400> SEQUENCE: 172

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg ccctttcggta cccgaaatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 173
<211> LENGTH: 540
<212> TYPE: DNA
<213> ORGANISM: Artificial Sequence
<220> FEATURE:
<223> OTHER INFORMATION: Recombinant

<400> SEQUENCE: 173

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg ccctttcggta cccgctatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 174
<211> LENGTH: 540
<212> TYPE: DNA
<213> ORGANISM: Artificial Sequence
<220> FEATURE:
<223> OTHER INFORMATION: Recombinant

<400> SEQUENCE: 174

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg ccctttcggta cccgaattac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 175
<211> LENGTH: 540
<212> TYPE: DNA
<213> ORGANISM: Artificial Sequence
<220> FEATURE:
<223> OTHER INFORMATION: Recombinant

<400> SEQUENCE: 175

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aaccctatg tccgaaaatt cttgcttgct acccccctggc agcccgcgtt gtgcggagtg   360
ttcgcagggg cccttcggta cccgcaatac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 176
<211> LENGTH: 540
<212> TYPE: DNA
<213> ORGANISM: Artificial Sequence
<220> FEATURE:
<223> OTHER INFORMATION: Recombinant

<400> SEQUENCE: 176

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aaccctatg tccgaaaatt cttgcttgct acccccctggc agcccgcgtt gtgcggagtg   360
ttcgcagggg cccttcggta cccgtcttac cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 177
<211> LENGTH: 540
<212> TYPE: DNA
<213> ORGANISM: Artificial Sequence
<220> FEATURE:
<223> OTHER INFORMATION: Recombinant

<400> SEQUENCE: 177

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aaccctatg tccgaaaatt cttgcttgct acccccctggc agcccgcgtt gtgcggagtg   360
ttcgcagggg cccttcggta cccgcgagct cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 178
<211> LENGTH: 540
<212> TYPE: DNA
<213> ORGANISM: Artificial Sequence
<220> FEATURE:
<223> OTHER INFORMATION: Recombinant

<400> SEQUENCE: 178

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg cccttcggta cccgcgatgc cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 179
<211> LENGTH: 540
<212> TYPE: DNA
<213> ORGANISM: Artificial Sequence
<220> FEATURE:
<223> OTHER INFORMATION: Recombinant

<400> SEQUENCE: 179

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg cccttcggta cccgcgacta cggtggatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 180
<211> LENGTH: 540
<212> TYPE: DNA
<213> ORGANISM: Artificial Sequence
<220> FEATURE:
<223> OTHER INFORMATION: Recombinant

<400> SEQUENCE: 180

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg cccttcggta cccgcgatgg cggtggatcg acaaggtgat gatccagcta   420
```

```
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 181
<211> LENGTH: 540
<212> TYPE: DNA
<213> ORGANISM: Artificial Sequence
<220> FEATURE:
<223> OTHER INFORMATION: Recombinant

<400> SEQUENCE: 181
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac gcttggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 182
<211> LENGTH: 540
<212> TYPE: DNA
<213> ORGANISM: Artificial Sequence
<220> FEATURE:
<223> OTHER INFORMATION: Recombinant

<400> SEQUENCE: 182
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cgggctatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 183
<211> LENGTH: 540
<212> TYPE: DNA
<213> ORGANISM: Artificial Sequence
<220> FEATURE:
<223> OTHER INFORMATION: Recombinant

<400> SEQUENCE: 183
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
```

```
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggttcatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 184
<211> LENGTH: 540
<212> TYPE: DNA
<213> ORGANISM: Artificial Sequence
<220> FEATURE:
<223> OTHER INFORMATION: Recombinant

<400> SEQUENCE: 184

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggataatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 185
<211> LENGTH: 540
<212> TYPE: DNA
<213> ORGANISM: Artificial Sequence
<220> FEATURE:
<223> OTHER INFORMATION: Recombinant

<400> SEQUENCE: 185

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggaaaatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 186
<211> LENGTH: 540
<212> TYPE: DNA
<213> ORGANISM: Artificial Sequence
<220> FEATURE:
<223> OTHER INFORMATION: Recombinant

<400> SEQUENCE: 186

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
```

```
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggctaatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 187
<211> LENGTH: 540
<212> TYPE: DNA
<213> ORGANISM: Artificial Sequence
<220> FEATURE:
<223> OTHER INFORMATION: Recombinant

<400> SEQUENCE: 187

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggcctatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 188
<211> LENGTH: 540
<212> TYPE: DNA
<213> ORGANISM: Artificial Sequence
<220> FEATURE:
<223> OTHER INFORMATION: Recombinant

<400> SEQUENCE: 188

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggcggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 189
<211> LENGTH: 540
<212> TYPE: DNA
<213> ORGANISM: Artificial Sequence
<220> FEATURE:
<223> OTHER INFORMATION: Recombinant

<400> SEQUENCE: 189

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccgggc agcccgcgtt gtgcggagtg   360
ttcgcagggg ccttcggta cccgcgatac cggtctatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 190
<211> LENGTH: 540
<212> TYPE: DNA
<213> ORGANISM: Artificial Sequence
<220> FEATURE:
<223> OTHER INFORMATION: Recombinant

<400> SEQUENCE: 190

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccgggc agcccgcgtt gtgcggagtg   360
ttcgcagggg ccttcggta cccgcgatac cggactatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 191
<211> LENGTH: 540
<212> TYPE: DNA
<213> ORGANISM: Artificial Sequence
<220> FEATURE:
<223> OTHER INFORMATION: Recombinant

<400> SEQUENCE: 191

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccgggc agcccgcgtt gtgcggagtg   360
ttcgcagggg ccttcggta cccgcgatac cgggtcatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 192
<211> LENGTH: 540

```
<212> TYPE: DNA
<213> ORGANISM: Artificial Sequence
<220> FEATURE:
<223> OTHER INFORMATION: Recombinant

<400> SEQUENCE: 192
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg cccttcggta cccgcgatac cggtatatcg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540

<210> SEQ ID NO 193
<211> LENGTH: 540
<212> TYPE: DNA
<213> ORGANISM: Artificial Sequence
<220> FEATURE:
<223> OTHER INFORMATION: Recombinant

<400> SEQUENCE: 193
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg cccttcggta cccgcgatac cggtgggctg acaaggtgat gatccagcta   420
ataatgcgga tgactggggg agagacagac acgagcaagg aggtcgagta cacggattgg   480
gagcaggtta agaagttcgc ggaggatttt gcaaagctat cgtacaagaa ggccctctag   540

<210> SEQ ID NO 194
<211> LENGTH: 540
<212> TYPE: DNA
<213> ORGANISM: Artificial Sequence
<220> FEATURE:
<223> OTHER INFORMATION: Recombinant

<400> SEQUENCE: 194
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct acccccctggc agcccgcgtt gtgcggagtg   360
ttcgcagggg cccttcggta cccgcgatac cggtggatcg ctaaggtgat gatccagcta   420
ataatgcgga tgactggggg agagacagac acgagcaagg aggtcgagta cacggattgg   480
```
gagcaggtta agaagttcgc ggaggatttt gcaaagctat cgtacaagaa ggccctctag    540

<210> SEQ ID NO 195
<211> LENGTH: 540
<212> TYPE: DNA
<213> ORGANISM: Artificial Sequence
<220> FEATURE:
<223> OTHER INFORMATION: Recombinant

<400> SEQUENCE: 195
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccttcggta cccgcgatac cggtggatca aaaggtgat gatccagcta    420 ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 196
<211> LENGTH: 540
<212> TYPE: DNA
<213> ORGANISM: Artificial Sequence
<220> FEATURE:
<223> OTHER INFORMATION: Recombinant

<400> SEQUENCE: 196
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccttcggta cccgcgatac cggtggatca ataagtgat gatccagcta    420 ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 197
<211> LENGTH: 540
<212> TYPE: DNA
<213> ORGANISM: Artificial Sequence
<220> FEATURE:
<223> OTHER INFORMATION: Recombinant

<400> SEQUENCE: 197
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccctccggta cccgcgatac cggtggatcc aaaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 198
<211> LENGTH: 540
<212> TYPE: DNA
<213> ORGANISM: Artificial Sequence
<220> FEATURE:
<223> OTHER INFORMATION: Recombinant

<400> SEQUENCE: 198
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccctccggta cccgcgatac cggtggatca ctaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 199
<211> LENGTH: 540
<212> TYPE: DNA
<213> ORGANISM: Artificial Sequence
<220> FEATURE:
<223> OTHER INFORMATION: Recombinant

<400> SEQUENCE: 199
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg ccctccggta cccgcgatac cggtggatcg acgctgtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 200
<211> LENGTH: 540
<212> TYPE: DNA
<213> ORGANISM: Artificial Sequence
<220> FEATURE:
<223> OTHER INFORMATION: Recombinant

<400> SEQUENCE: 200
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180

| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct accccctggc agcccgcgtt gtgcggagtg | 360 |
| ttcgcagggg cccttcggta cccgcgatac cggtggatcg accaagtgat gatccagcta | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

```
<210> SEQ ID NO 201
<211> LENGTH: 540
<212> TYPE: DNA
<213> ORGANISM: Artificial Sequence
<220> FEATURE:
<223> OTHER INFORMATION: Recombinant

<400> SEQUENCE: 201
```

| atgaaggcct tggtactgta ctcgacgcgg gacggccaga cccacgcaat tgcttcatac | 60 |
| atcgcctcct gcatgaagga gaaggccgaa tgcgacgtga tcgacctcac ccacggggag | 120 |
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct accccctggc agcccgcgtt gtgcggagtg | 360 |
| ttcgcagggg cccttcggta cccgcgatac cggtggatcg accgggtgat gatccagcta | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

```
<210> SEQ ID NO 202
<211> LENGTH: 540
<212> TYPE: DNA
<213> ORGANISM: Artificial Sequence
<220> FEATURE:
<223> OTHER INFORMATION: Recombinant

<400> SEQUENCE: 202
```

| atgaaggcct tggtactgta ctcgacgcgg gacggccaga cccacgcaat tgcttcatac | 60 |
| atcgcctcct gcatgaagga gaaggccgaa tgcgacgtga tcgacctcac ccacggggag | 120 |
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct accccctggc agcccgcgtt gtgcggagtg | 360 |
| ttcgcagggg cccttcggta cccgcgatac cggtggatcg actctgtgat gatccagcta | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

```
<210> SEQ ID NO 203
<211> LENGTH: 540
<212> TYPE: DNA
<213> ORGANISM: Artificial Sequence
<220> FEATURE:
<223> OTHER INFORMATION: Recombinant

<400> SEQUENCE: 203
```

| atgaaggcct tggtactgta ctcgacgcgg gacggccaga cccacgcaat tgcttcatac | 60 |

```
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acactgtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 204
<211> LENGTH: 540
<212> TYPE: DNA
<213> ORGANISM: Artificial Sequence
<220> FEATURE:
<223> OTHER INFORMATION: Recombinant

<400> SEQUENCE: 204

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acgtcgtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 205
<211> LENGTH: 540
<212> TYPE: DNA
<213> ORGANISM: Artificial Sequence
<220> FEATURE:
<223> OTHER INFORMATION: Recombinant

<400> SEQUENCE: 205

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggctat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 206
<211> LENGTH: 540
<212> TYPE: DNA
<213> ORGANISM: Artificial Sequence
<220> FEATURE:

<223> OTHER INFORMATION: Recombinant

<400> SEQUENCE: 206

| | |
|---|---|
| atgaaggcct tggtactgta ctcgacgcgg gacggccaga cccacgcaat tgcttcatac | 60 |
| atcgcctcct gcatgaagga gaaggccgaa tgcgacgtga tcgacctcac ccacggggag | 120 |
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct acccccctggc agcccgcgtt gtgcggagtg | 360 |
| ttcgcagggg cccttcggta cccgcgatac cggtggatcg acaaggtggc tatccagcta | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

<210> SEQ ID NO 207
<211> LENGTH: 540
<212> TYPE: DNA
<213> ORGANISM: Artificial Sequence
<220> FEATURE:
<223> OTHER INFORMATION: Recombinant

<400> SEQUENCE: 207

| | |
|---|---|
| atgaaggcct tggtactgta ctcgacgcgg gacggccaga cccacgcaat tgcttcatac | 60 |
| atcgcctcct gcatgaagga gaaggccgaa tgcgacgtga tcgacctcac ccacggggag | 120 |
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct acccccctggc agcccgcgtt gtgcggagtg | 360 |
| ttcgcagggg cccttcggta cccgcgatac cggtggatcg acaaggtgtg catccagcta | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

<210> SEQ ID NO 208
<211> LENGTH: 540
<212> TYPE: DNA
<213> ORGANISM: Artificial Sequence
<220> FEATURE:
<223> OTHER INFORMATION: Recombinant

<400> SEQUENCE: 208

| | |
|---|---|
| atgaaggcct tggtactgta ctcgacgcgg gacggccaga cccacgcaat tgcttcatac | 60 |
| atcgcctcct gcatgaagga gaaggccgaa tgcgacgtga tcgacctcac ccacggggag | 120 |
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct acccccctggc agcccgcgtt gtgcggagtg | 360 |
| ttcgcagggg cccttcggta cccgcgatac cggtggatcg acaaggtgat aatccagcta | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

<210> SEQ ID NO 209
<211> LENGTH: 540
<212> TYPE: DNA
<213> ORGANISM: Artificial Sequence
<220> FEATURE:
<223> OTHER INFORMATION: Recombinant

<400> SEQUENCE: 209

| | | | | | |
|---|---|---|---|---|---|
| atgaaggcct | tggtactgta | ctcgacgcgg | gacggccaga | cccacgcaat | tgcttcatac | 60 |
| atcgcctcct | gcatgaagga | gaaggccgaa | tgcgacgtga | tcgacctcac | ccacggggag | 120 |
| cacgtgaacc | tcacccaata | cgatcaggtg | ctaatcggtg | cgagtattcg | ttacggccac | 180 |
| ttcaacgccg | tgcttgacaa | gttcatcaag | agaaacgtgg | atcagctgaa | caacatgcca | 240 |
| agcgcgttct | tctgcgtaaa | cctcacagca | aggaagcccg | agaagcgtac | tccccagaca | 300 |
| aacccttatg | tccgaaaatt | cttgcttgct | accccctggc | agcccgcgtt | gtgcggagtg | 360 |
| ttcgcagggg | cccttcggta | cccgcgatac | cggtggatcg | acaaggtgct | aatccagcta | 420 |
| ataatgcgga | tgactggggg | agagacagac | acgagcaagg | aggtcgagta | cacggattgg | 480 |
| gagcaggtta | agaagttcgc | ggaggatttt | gcaaagctat | cgtacaagaa | ggccctctag | 540 |

<210> SEQ ID NO 210
<211> LENGTH: 540
<212> TYPE: DNA
<213> ORGANISM: Artificial Sequence
<220> FEATURE:
<223> OTHER INFORMATION: Recombinant

<400> SEQUENCE: 210

| | | | | | |
|---|---|---|---|---|---|
| atgaaggcct | tggtactgta | ctcgacgcgg | gacggccaga | cccacgcaat | tgcttcatac | 60 |
| atcgcctcct | gcatgaagga | gaaggccgaa | tgcgacgtga | tcgacctcac | ccacggggag | 120 |
| cacgtgaacc | tcacccaata | cgatcaggtg | ctaatcggtg | cgagtattcg | ttacggccac | 180 |
| ttcaacgccg | tgcttgacaa | gttcatcaag | agaaacgtgg | atcagctgaa | caacatgcca | 240 |
| agcgcgttct | tctgcgtaaa | cctcacagca | aggaagcccg | agaagcgtac | tccccagaca | 300 |
| aacccttatg | tccgaaaatt | cttgcttgct | accccctggc | agcccgcgtt | gtgcggagtg | 360 |
| ttcgcagggg | cccttcggta | cccgcgatac | cggtggatcg | acaaggtgtc | tatccagcta | 420 |
| ataatgcgga | tgactggggg | agagacagac | acgagcaagg | aggtcgagta | cacggattgg | 480 |
| gagcaggtta | agaagttcgc | ggaggatttt | gcaaagctat | cgtacaagaa | ggccctctag | 540 |

<210> SEQ ID NO 211
<211> LENGTH: 540
<212> TYPE: DNA
<213> ORGANISM: Artificial Sequence
<220> FEATURE:
<223> OTHER INFORMATION: Recombinant

<400> SEQUENCE: 211

| | | | | | |
|---|---|---|---|---|---|
| atgaaggcct | tggtactgta | ctcgacgcgg | gacggccaga | cccacgcaat | tgcttcatac | 60 |
| atcgcctcct | gcatgaagga | gaaggccgaa | tgcgacgtga | tcgacctcac | ccacggggag | 120 |
| cacgtgaacc | tcacccaata | cgatcaggtg | ctaatcggtg | cgagtattcg | ttacggccac | 180 |
| ttcaacgccg | tgcttgacaa | gttcatcaag | agaaacgtgg | atcagctgaa | caacatgcca | 240 |
| agcgcgttct | tctgcgtaaa | cctcacagca | aggaagcccg | agaagcgtac | tccccagaca | 300 |
| aacccttatg | tccgaaaatt | cttgcttgct | accccctggc | agcccgcgtt | gtgcggagtg | 360 |
| ttcgcagggg | cccttcggta | cccgcgatac | cggtggatcg | acaaggtggt | catccagcta | 420 |

```
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 212
<211> LENGTH: 540
<212> TYPE: DNA
<213> ORGANISM: Artificial Sequence
<220> FEATURE:
<223> OTHER INFORMATION: Recombinant

<400> SEQUENCE: 212

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct acccccctggc agcccgcgtt gtgcggagtg   360
ttcgcagggg cccttcggta cccgcgatac cggtggatcg acaaggtgat ggctcagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 213
<211> LENGTH: 540
<212> TYPE: DNA
<213> ORGANISM: Artificial Sequence
<220> FEATURE:
<223> OTHER INFORMATION: Recombinant

<400> SEQUENCE: 213

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct acccccctggc agcccgcgtt gtgcggagtg   360
ttcgcagggg cccttcggta cccgcgatac cggtggatcg acaaggtgat gctacagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 214
<211> LENGTH: 540
<212> TYPE: DNA
<213> ORGANISM: Artificial Sequence
<220> FEATURE:
<223> OTHER INFORMATION: Recombinant

<400> SEQUENCE: 214

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
```

```
aacccttatg tccgaaaatt cttgcttgct accccctggc agcccgcgtt gtgcggagtg    360
ttcgcagggg cccttcggta cccgcgatac cggtggatcg acaaggtgat gatgcagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 215
<211> LENGTH: 540
<212> TYPE: DNA
<213> ORGANISM: Artificial Sequence
<220> FEATURE:
<223> OTHER INFORMATION: Recombinant

<400> SEQUENCE: 215
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat ggtccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 216
<211> LENGTH: 540
<212> TYPE: DNA
<213> ORGANISM: Artificial Sequence
<220> FEATURE:
<223> OTHER INFORMATION: Recombinant

<400> SEQUENCE: 216
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccaggct    420
ataatgcgga tgactggggg agagacagac acgagcaagg aggtcgagta cacggattgg    480
gagcaggtta agaagttcgc ggaggatttt gcaaagctat cgtacaagaa ggccctctag    540

<210> SEQ ID NO 217
<211> LENGTH: 540
<212> TYPE: DNA
<213> ORGANISM: Artificial Sequence
<220> FEATURE:
<223> OTHER INFORMATION: Recombinant

<400> SEQUENCE: 217
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
```

| | |
|---|---|
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct accccctggc agcccgcgtt gtgcggagtg | 360 |
| ttcgcagggg cccttcggta cccgcgatac cggtggatcg acaaggtgat gatccagtgc | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

<210> SEQ ID NO 218
<211> LENGTH: 540
<212> TYPE: DNA
<213> ORGANISM: Artificial Sequence
<220> FEATURE:
<223> OTHER INFORMATION: Recombinant

<400> SEQUENCE: 218

| | |
|---|---|
| atgaaggcct tggtactgta ctcgacgcgg gacggccaga cccacgcaat tgcttcatac | 60 |
| atcgcctcct gcatgaagga gaaggccgaa tgcgacgtga tcgacctcac ccacggggag | 120 |
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct accccctggc agcccgcgtt gtgcggagtg | 360 |
| ttcgcagggg cccttcggta cccgcgatac cggtggatcg acaaggtgat gatccagttc | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

<210> SEQ ID NO 219
<211> LENGTH: 540
<212> TYPE: DNA
<213> ORGANISM: Artificial Sequence
<220> FEATURE:
<223> OTHER INFORMATION: Recombinant

<400> SEQUENCE: 219

| | |
|---|---|
| atgaaggcct tggtactgta ctcgacgcgg gacggccaga cccacgcaat tgcttcatac | 60 |
| atcgcctcct gcatgaagga gaaggccgaa tgcgacgtga tcgacctcac ccacggggag | 120 |
| cacgtgaacc tcacccaata cgatcaggtg ctaatcggtg cgagtattcg ttacggccac | 180 |
| ttcaacgccg tgcttgacaa gttcatcaag agaaacgtgg atcagctgaa caacatgcca | 240 |
| agcgcgttct tctgcgtaaa cctcacagca aggaagcccg agaagcgtac tccccagaca | 300 |
| aacccttatg tccgaaaatt cttgcttgct accccctggc agcccgcgtt gtgcggagtg | 360 |
| ttcgcagggg cccttcggta cccgcgatac cggtggatcg acaaggtgat gatccagggc | 420 |
| ataatgcgga tgactggggg agagacagac acgagcaagg aggtcgagta cacggattgg | 480 |
| gagcaggtta agaagttcgc ggaggatttt gcaaagctat cgtacaagaa ggccctctag | 540 |

<210> SEQ ID NO 220
<211> LENGTH: 540
<212> TYPE: DNA
<213> ORGANISM: Artificial Sequence
<220> FEATURE:
<223> OTHER INFORMATION: Recombinant

<400> SEQUENCE: 220

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg ccttcggta cccgcgatac cggtggatcg acaaggtgat gatccagcat   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 221
<211> LENGTH: 540
<212> TYPE: DNA
<213> ORGANISM: Artificial Sequence
<220> FEATURE:
<223> OTHER INFORMATION: Recombinant

<400> SEQUENCE: 221

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg ccttcggta cccgcgatac cggtggatcg acaaggtgat gatccagata   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 222
<211> LENGTH: 540
<212> TYPE: DNA
<213> ORGANISM: Artificial Sequence
<220> FEATURE:
<223> OTHER INFORMATION: Recombinant

<400> SEQUENCE: 222

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag   120
cacgtgaacc tcacccaata cgatcaggtg ctaatcggtg cgagtattcg ttacggccac   180
ttcaacgccg tgcttgacaa gttcatcaag agaaacgtgg atcagctgaa caacatgcca   240
agcgcgttct tctgcgtaaa cctcacagca aggaagcccg agaagcgtac tccccagaca   300
aacccttatg tccgaaaatt cttgcttgct accccctggc agcccgcgtt gtgcggagtg   360
ttcgcagggg ccttcggta cccgcgatac cggtggatcg acaaggtgat gatccagaaa   420
ataatgcgga tgactggggg agagacagac acgagcaagg aggtcgagta cacggattgg   480
gagcaggtta agaagttcgc ggaggatttt gcaaagctat cgtacaagaa ggccctctag   540
```

<210> SEQ ID NO 223
<211> LENGTH: 540
<212> TYPE: DNA

```
<213> ORGANISM: Artificial Sequence
<220> FEATURE:
<223> OTHER INFORMATION: Recombinant

<400> SEQUENCE: 223
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300 aaccctatg tccgaaaatt cttgcttgct accccctggc agcccgcgtt gtgcggagtg      360
ttcgcagggg cccttcggta cccgcgatac cggtggatcg acaaggtgat gatccagatg     420
ataatgcgga tgactggggg agagacagac acgagcaagg aggtcgagta cacggattgg     480
gagcaggtta agaagttcgc ggaggatttt gcaaagctat cgtacaagaa ggccctctag     540

<210> SEQ ID NO 224
<211> LENGTH: 540
<212> TYPE: DNA
<213> ORGANISM: Artificial Sequence
<220> FEATURE:
<223> OTHER INFORMATION: Recombinant

<400> SEQUENCE: 224
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300 aaccctatg tccgaaaatt cttgcttgct accccctggc agcccgcgtt gtgcggagtg      360
ttcgcagggg cccttcggta cccgcgatac cggtggatcg acaaggtgat gatccagcgg     420
ataatgcgga tgactggggg agagacagac acgagcaagg aggtcgagta cacggattgg     480
gagcaggtta agaagttcgc ggaggatttt gcaaagctat cgtacaagaa ggccctctag     540

<210> SEQ ID NO 225
<211> LENGTH: 540
<212> TYPE: DNA
<213> ORGANISM: Artificial Sequence
<220> FEATURE:
<223> OTHER INFORMATION: Recombinant

<400> SEQUENCE: 225
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300 aaccctatg tccgaaaatt cttgcttgct accccctggc agcccgcgtt gtgcggagtg      360
ttcgcagggg cccttcggta cccgcgatac cggtggatcg acaaggtgat gatccagact     420
ataatgcgga tgactggggg agagacagac acgagcaagg aggtcgagta cacggattgg     480
gagcaggtta agaagttcgc ggaggatttt gcaaagctat cgtacaagaa ggccctctag     540
```

<210> SEQ ID NO 226
<211> LENGTH: 540
<212> TYPE: DNA
<213> ORGANISM: Artificial Sequence
<220> FEATURE:
<223> OTHER INFORMATION: Recombinant

<400> SEQUENCE: 226

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct accccctggc agcccgcgtt gtgcggagtg     360
ttcgcagggg cccttcggta cccgcgatac cggtggatcg acaaggtgat gatccagcta     420
gctatgcgga tgactggggg agagacagac acgagcaagg aggtcgagta cacggattgg     480
gagcaggtta agaagttcgc ggaggatttt gcaaagctat cgtacaagaa ggccctctag     540
```

<210> SEQ ID NO 227
<211> LENGTH: 540
<212> TYPE: DNA
<213> ORGANISM: Artificial Sequence
<220> FEATURE:
<223> OTHER INFORMATION: Recombinant

<400> SEQUENCE: 227

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct accccctggc agcccgcgtt gtgcggagtg     360
ttcgcagggg cccttcggta cccgcgatac cggtggatcg acaaggtgat gatccagcta     420
ctaatgcgga tgactggggg agagacagac acgagcaagg aggtcgagta cacggattgg     480
gagcaggtta agaagttcgc ggaggatttt gcaaagctat cgtacaagaa ggccctctag     540
```

<210> SEQ ID NO 228
<211> LENGTH: 540
<212> TYPE: DNA
<213> ORGANISM: Artificial Sequence
<220> FEATURE:
<223> OTHER INFORMATION: Recombinant

<400> SEQUENCE: 228

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct accccctggc agcccgcgtt gtgcggagtg     360
```

```
ttcgcagggg cccttcggta cccgcgatac cggtggatcg acaaggtgat gatccagcta    420
atgatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 229
<211> LENGTH: 540
<212> TYPE: DNA
<213> ORGANISM: Artificial Sequence
<220> FEATURE:
<223> OTHER INFORMATION: Recombinant

<400> SEQUENCE: 229

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
gtcatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 230
<211> LENGTH: 540
<212> TYPE: DNA
<213> ORGANISM: Artificial Sequence
<220> FEATURE:
<223> OTHER INFORMATION: Recombinant

<400> SEQUENCE: 230

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
atagctcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 231
<211> LENGTH: 540
<212> TYPE: DNA
<213> ORGANISM: Artificial Sequence
<220> FEATURE:
<223> OTHER INFORMATION: Recombinant

<400> SEQUENCE: 231

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
```

```
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
atagatcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 232
<211> LENGTH: 540
<212> TYPE: DNA
<213> ORGANISM: Artificial Sequence
<220> FEATURE:
<223> OTHER INFORMATION: Recombinant

<400> SEQUENCE: 232

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
atactacgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 233
<211> LENGTH: 540
<212> TYPE: DNA
<213> ORGANISM: Artificial Sequence
<220> FEATURE:
<223> OTHER INFORMATION: Recombinant

<400> SEQUENCE: 233

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
atatctcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 234
<211> LENGTH: 540
<212> TYPE: DNA
<213> ORGANISM: Artificial Sequence
<220> FEATURE:
<223> OTHER INFORMATION: Recombinant

<400> SEQUENCE: 234

```
atgaaggcct tggtactgta ctcgacgcgg gacggccaga cccacgcaat tgcttcatac     60
```

```
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct acccctggc agcccgcgtt gtgcggagtg     360
ttcgcagggg ccttcggta cccgcgatac cggtggatcg acaaggtgat gatccagcta     420
atagtccgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 235
<211> LENGTH: 540
<212> TYPE: DNA
<213> ORGANISM: Artificial Sequence
<220> FEATURE:
<223> OTHER INFORMATION: Recombinant

<400> SEQUENCE: 235

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct acccctggc agcccgcgtt gtgcggagtg     360
ttcgcagggg ccttcggta cccgcgatac cggtggatcg acaaggtgat gatccagcta     420
ataatggcta tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 236
<211> LENGTH: 540
<212> TYPE: DNA
<213> ORGANISM: Artificial Sequence
<220> FEATURE:
<223> OTHER INFORMATION: Recombinant

<400> SEQUENCE: 236

```
atgaaggcct tggtactgta ctcgacgcgg gacggccaga cccacgcaat tgcttcatac    60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct acccctggc agcccgcgtt gtgcggagtg     360
ttcgcagggg ccttcggta cccgcgatac cggtggatcg acaaggtgat gatccagcta     420
ataatgcggg ctactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 237
<211> LENGTH: 540
<212> TYPE: DNA
<213> ORGANISM: Artificial Sequence
<220> FEATURE:
<223> OTHER INFORMATION: Recombinant

<400> SEQUENCE: 237

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct acccccctggc agcccgcgtt gtgcggagtg    360
ttcgcagggg cccttcggta cccgcgatac cggtggatcg acaaggtgat gatccagcta    420
ataatgcgga tggctggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 238
<211> LENGTH: 540
<212> TYPE: DNA
<213> ORGANISM: Artificial Sequence
<220> FEATURE:
<223> OTHER INFORMATION: Recombinant

<400> SEQUENCE: 238

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct acccccctggc agcccgcgtt gtgcggagtg    360
ttcgcagggg cccttcggta cccgcgatac cggtggatcg acaaggtgat gatccagcta    420
ataatgcgga tgactgctgg agagacagac acgagcaagg aggtcgagta cacggattgg    480
gagcaggtta agaagttcgc ggaggatttt gcaaagctat cgtacaagaa ggccctctag    540
```

<210> SEQ ID NO 239
<211> LENGTH: 540
<212> TYPE: DNA
<213> ORGANISM: Artificial Sequence
<220> FEATURE:
<223> OTHER INFORMATION: Recombinant

<400> SEQUENCE: 239

```
atgaaggcct tggtactgta ctcgacgcgg gacggccaga cccacgcaat tgcttcatac      60
atcgcctcct gcatgaagga gaaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct acccccctggc agcccgcgtt gtgcggagtg    360
ttcgcagggg cccttcggta cccgcgatac cggtggatcg acaaggtgat gatccagcta    420
ataatgcgga tgactgatgg agagacagac acgagcaagg aggtcgagta cacggattgg    480
gagcaggtta agaagttcgc ggaggatttt gcaaagctat cgtacaagaa ggccctctag    540
```

<210> SEQ ID NO 240

```
<211> LENGTH: 540
<212> TYPE: DNA
<213> ORGANISM: Artificial Sequence
<220> FEATURE:
<223> OTHER INFORMATION: Recombinant

<400> SEQUENCE: 240
atgaaggcct tggtactgta ctcgacgcgg gacggccaga cccacgcaat tgcttcatac      60
atcgcctcct gcatgaagga aaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct accccctggc agcccgcgtt gtgcggagtg     360
ttcgcagggg cccttcggta cccgcgatac cggtggatcg acaaggtgat gatccagcta     420
ataatgcgga tgactcatgg agagacagac acgagcaagg aggtcgagta cacggattgg     480
gagcaggtta agaagttcgc ggaggatttt gcaaagctat cgtacaagaa ggccctctag     540

<210> SEQ ID NO 241
<211> LENGTH: 540
<212> TYPE: DNA
<213> ORGANISM: Artificial Sequence
<220> FEATURE:
<223> OTHER INFORMATION: Recombinant

<400> SEQUENCE: 241
atgaaggcct tggtactgta ctcgacgcgg gacggccaga cccacgcaat tgcttcatac      60
atcgcctcct gcatgaagga aaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct accccctggc agcccgcgtt gtgcggagtg     360
ttcgcagggg cccttcggta cccgcgatac cggtggatcg acaaggtgat gatccagcta     420
ataatgcgga tgactaaagg agagacagac acgagcaagg aggtcgagta cacggattgg     480
gagcaggtta agaagttcgc ggaggatttt gcaaagctat cgtacaagaa ggccctctag     540

<210> SEQ ID NO 242
<211> LENGTH: 540
<212> TYPE: DNA
<213> ORGANISM: Artificial Sequence
<220> FEATURE:
<223> OTHER INFORMATION: Recombinant

<400> SEQUENCE: 242
atgaaggcct tggtactgta ctcgacgcgg gacggccaga cccacgcaat tgcttcatac      60
atcgcctcct gcatgaagga aaggccgaa tgcgacgtga tcgacctcac ccacggggag     120
cacgtgaacc tcacccaata cgatcaggtg ctaatcggtg cgagtattcg ttacggccac     180
ttcaacgccg tgcttgacaa gttcatcaag agaaacgtgg atcagctgaa caacatgcca     240
agcgcgttct tctgcgtaaa cctcacagca aggaagcccg agaagcgtac tccccagaca     300
aacccttatg tccgaaaatt cttgcttgct accccctggc agcccgcgtt gtgcggagtg     360
ttcgcagggg cccttcggta cccgcgatac cggtggatcg acaaggtgat gatccagcta     420
ataatgcgga tgactaatgg agagacagac acgagcaagg aggtcgagta cacggattgg     480
```

```
gagcaggtta agaagttcgc ggaggatttt gcaaagctat cgtacaagaa ggccctctag    540
```

<210> SEQ ID NO 243
<211> LENGTH: 540
<212> TYPE: DNA
<213> ORGANISM: Artificial Sequence
<220> FEATURE:
<223> OTHER INFORMATION: Recombinant

<400> SEQUENCE: 243

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
ataatgcgga tgactggggc tgagacagac acgagcaagg aggtcgagta cacggattgg    480
gagcaggtta agaagttcgc ggaggatttt gcaaagctat cgtacaagaa ggccctctag    540
```

<210> SEQ ID NO 244
<211> LENGTH: 540
<212> TYPE: DNA
<213> ORGANISM: Artificial Sequence
<220> FEATURE:
<223> OTHER INFORMATION: Recombinant

<400> SEQUENCE: 244

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
ataatgcgga tgactgggaa agagacagac acgagcaagg aggtcgagta cacggattgg    480
gagcaggtta agaagttcgc ggaggatttt gcaaagctat cgtacaagaa ggccctctag    540
```

<210> SEQ ID NO 245
<211> LENGTH: 540
<212> TYPE: DNA
<213> ORGANISM: Artificial Sequence
<220> FEATURE:
<223> OTHER INFORMATION: Recombinant

<400> SEQUENCE: 245

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
```

```
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
ataatgcgga tgactgggat ggagacagac acgagcaagg aggtcgagta cacggattgg    480
gagcaggtta agaagttcgc ggaggatttt gcaaagctat cgtacaagaa ggccctctag    540
```

<210> SEQ ID NO 246
<211> LENGTH: 540
<212> TYPE: DNA
<213> ORGANISM: Artificial Sequence
<220> FEATURE:
<223> OTHER INFORMATION: Recombinant

<400> SEQUENCE: 246

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
ataatgcgga tgactgggcg ggagacagac acgagcaagg aggtcgagta cacggattgg    480
gagcaggtta agaagttcgc ggaggatttt gcaaagctat cgtacaagaa ggccctctag    540
```

<210> SEQ ID NO 247
<211> LENGTH: 540
<212> TYPE: DNA
<213> ORGANISM: Artificial Sequence
<220> FEATURE:
<223> OTHER INFORMATION: Recombinant

<400> SEQUENCE: 247

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatccagcta    420
ataatgcgga tgactgggtc tgagacagac acgagcaagg aggtcgagta cacggattgg    480
gagcaggtta agaagttcgc ggaggatttt gcaaagctat cgtacaagaa ggccctctag    540
```

<210> SEQ ID NO 248
<211> LENGTH: 540
<212> TYPE: DNA
<213> ORGANISM: Artificial Sequence
<220> FEATURE:
<223> OTHER INFORMATION: Recombinant

<400> SEQUENCE: 248

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
```

```
ttcaacgccg tgcttgacaa gttcatcaag agaaacgtgg atcagctgaa caacatgcca    240
agcgcgttct tctgcgtaaa cctcacagca aggaagcccg agaagcgtac tccccagaca    300
aacccttatg tccgaaaatt cttgcttgct accccctggc agcccgcgtt gtgcggagtg    360
ttcgcagggg cccttcggta cccgcgatac cggtggatcg acaaggtgat gatcgctcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 249
<211> LENGTH: 179
<212> TYPE: PRT
<213> ORGANISM: Artificial Sequence
<220> FEATURE:
<223> OTHER INFORMATION: Recombinant

<400> SEQUENCE: 249

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Cys Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 250
<211> LENGTH: 179
<212> TYPE: PRT
<213> ORGANISM: Artificial Sequence
<220> FEATURE:
<223> OTHER INFORMATION: Recombinant

<400> SEQUENCE: 250

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60
```

```
Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Glu Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 251
<211> LENGTH: 179
<212> TYPE: PRT
<213> ORGANISM: Artificial Sequence
<220> FEATURE:
<223> OTHER INFORMATION: Recombinant

<400> SEQUENCE: 251

```
Met Lys Ala Leu Val Leu Tyr Ser Thr Arg Asp Gly Gln Thr His Ala
  1               5                  10                  15

Ile Ala Ser Tyr Ile Ala Ser Cys Met Lys Glu Lys Ala Glu Cys Asp
                 20                  25                  30

Val Ile Asp Leu Thr His Gly Glu His Val Asn Leu Thr Gln Tyr Asp
             35                  40                  45

Gln Val Leu Ile Gly Ala Ser Ile Arg Tyr Gly His Phe Asn Ala Val
 50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gly Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 252
<211> LENGTH: 179
<212> TYPE: PRT
<213> ORGANISM: Artificial Sequence
<220> FEATURE:
<223> OTHER INFORMATION: Recombinant

<400> SEQUENCE: 252

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile His Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                    165                 170                 175

Lys Ala Leu

<210> SEQ ID NO 253
<211> LENGTH: 179
<212> TYPE: PRT
<213> ORGANISM: Artificial Sequence
<220> FEATURE:
<223> OTHER INFORMATION: Recombinant

<400> SEQUENCE: 253

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Lys Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                    165                 170                 175

Lys Ala Leu
```

<210> SEQ ID NO 254
<211> LENGTH: 179
<212> TYPE: PRT
<213> ORGANISM: Artificial Sequence
<220> FEATURE:
<223> OTHER INFORMATION: Recombinant

<400> SEQUENCE: 254

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Leu Leu Ile Met Arg Met
    130                 135                 140

Thr Gly Gly Glu Thr Asp Thr Ser Lys Glu Val Gly Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 255
<211> LENGTH: 179
<212> TYPE: PRT
<213> ORGANISM: Artificial Sequence
<220> FEATURE:
<223> OTHER INFORMATION: Recombinant

<400> SEQUENCE: 255

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Met Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 256
<211> LENGTH: 179
<212> TYPE: PRT
<213> ORGANISM: Artificial Sequence
<220> FEATURE:
<223> OTHER INFORMATION: Recombinant

<400> SEQUENCE: 256

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Arg Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 257
<211> LENGTH: 179
<212> TYPE: PRT
<213> ORGANISM: Artificial Sequence
<220> FEATURE:
<223> OTHER INFORMATION: Recombinant

<400> SEQUENCE: 257

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

```
Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Ser Leu Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 258
<211> LENGTH: 179
<212> TYPE: PRT
<213> ORGANISM: Artificial Sequence
<220> FEATURE:
<223> OTHER INFORMATION: Recombinant

<400> SEQUENCE: 258

Met Lys Ala Leu Val Leu Tyr Ser Thr Arg Asp Gly Gln Thr His Ala
 1               5                  10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
 65                  70                  75                  80

Ser Ala Phe Phe Cys Val Asn Leu Thr Ala Arg Lys Pro Glu Lys Arg
                 85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
                115                 120                 125

Arg Tyr Arg Trp Ile Asp Lys Val Met Ile Gln Asn Ile Met Arg Met
            130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 259
<211> LENGTH: 179
<212> TYPE: PRT
<213> ORGANISM: Artificial Sequence
<220> FEATURE:
<223> OTHER INFORMATION: Recombinant

<400> SEQUENCE: 259

Met Lys Ala Leu Val Leu Tyr Ser Thr Arg Asp Gly Gln Thr His Ala
```

```
1               5                   10                  15
Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 260
<211> LENGTH: 179
<212> TYPE: PRT
<213> ORGANISM: Artificial Sequence
<220> FEATURE:
<223> OTHER INFORMATION: Recombinant

<400> SEQUENCE: 260

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Ser Ile Met Arg Met
130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 261
<211> LENGTH: 179
<212> TYPE: PRT
<213> ORGANISM: Artificial Sequence
<220> FEATURE:
<223> OTHER INFORMATION: Recombinant

<400> SEQUENCE: 261

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Val Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 262
<211> LENGTH: 179
<212> TYPE: PRT
<213> ORGANISM: Artificial Sequence
<220> FEATURE:
<223> OTHER INFORMATION: Recombinant

<400> SEQUENCE: 262

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125
```

Arg Tyr Arg Trp Ile Asp Lys Val Met Ile Gln Trp Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 263
<211> LENGTH: 179
<212> TYPE: PRT
<213> ORGANISM: Artificial Sequence
<220> FEATURE:
<223> OTHER INFORMATION: Recombinant

<400> SEQUENCE: 263

Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
                20                  25                  30

Val Ile Asp Leu Thr His Gly Glu His Val Asn Leu Thr Gln Tyr Asp
            35                  40                  45

Gln Val Leu Ile Gly Ala Ser Ile Arg Tyr Gly His Phe Asn Ala Val
        50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
                100                 105                 110

Trp Gln Pro Ala Leu Cys Gly Val Phe Ala Gly Ala Leu Arg Tyr Pro
            115                 120                 125

Arg Tyr Arg Trp Ile Asp Lys Val Met Ile Gln Tyr Ile Met Arg Met
        130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu

<210> SEQ ID NO 264
<211> LENGTH: 537
<212> TYPE: DNA
<213> ORGANISM: Artificial Sequence
<220> FEATURE:
<223> OTHER INFORMATION: Recombinant

<400> SEQUENCE: 264
atgaaagcgc tggtgctgta tagcacccgc gatggccaga cccatgcgat tgcgagctat     60
attgcgagct gcatgaaaga aaaagcggaa tgcgatgtga ttgatctgac ccatggcgaa    120
catgtgaacc tgacccagta tgatcaggtg ctgattggcg cgagcattcg ctatggccat    180
tttaacgcgg tgctggataa atttattaaa cgcaacgtgg atcagctgaa caacatgccg    240
agcgcgtttt tttgcgtgaa cctgaccgcg cgcaaaccgg aaaaacgcac cccgcagacc    300
aacccgtatg tgcgcaaatt tctgctggcg acccgtggc agccggcgct gtgcggcgtg    360
tttgcgggcg cgctgcgcta tccgcgctat cgctggattg ataaagtgat gatttgcctg    420

```
attatgcgca tgaccggcgg cgaaaccgat accagcaaag aagtggaata taccgattgg    480
gaacaggtga aaaaatttgc ggaagatttt gcgaaactga gctataaaaa agcgctg      537
```

<210> SEQ ID NO 265
<211> LENGTH: 537
<212> TYPE: DNA
<213> ORGANISM: Artificial Sequence
<220> FEATURE:
<223> OTHER INFORMATION: Recombinant

<400> SEQUENCE: 265

```
atgaaagcgc tggtgctgta tagcacccgc gatggccaga cccatgcgat tgcgagctat    60
attgcgagct gcatgaaaga aaaagcggaa tgcgatgtga ttgatctgac ccatggcgaa   120
catgtgaacc tgacccagta tgatcaggtg ctgattggcg cgagcattcg ctatggccat   180
tttaacgcgg tgctggataa atttattaaa cgcaacgtgg atcagctgaa caacatgccg   240
agcgcgtttt tttgcgtgaa cctgaccgcg cgcaaaccgg aaaaacgcac cccgcagacc   300
aacccgtatg tgcgcaaatt tctgctggcg accccgtggc agccggcgct gtgcggcgtg   360
tttgcgggcg cgctgcgcta tccgcgctat cgctggattg ataaagtgat gattgaactg   420
attatgcgca tgaccggcgg cgaaaccgat accagcaaag aagtggaata taccgattgg   480
gaacaggtga aaaaatttgc ggaagatttt gcgaaactga gctataaaaa agcgctg      537
```

<210> SEQ ID NO 266
<211> LENGTH: 537
<212> TYPE: DNA
<213> ORGANISM: Artificial Sequence
<220> FEATURE:
<223> OTHER INFORMATION: Recombinant

<400> SEQUENCE: 266

```
atgaaagcgc tggtgctgta tagcacccgc gatggccaga cccatgcgat tgcgagctat    60
attgcgagct gcatgaaaga aaaagcggaa tgcgatgtga ttgatctgac ccatggcgaa   120
catgtgaacc tgacccagta tgatcaggtg ctgattggcg cgagcattcg ctatggccat   180
tttaacgcgg tgctggataa atttattaaa cgcaacgtgg atcagctgaa caacatgccg   240
agcgcgtttt tttgcgtgaa cctgaccgcg cgcaaaccgg aaaaacgcac cccgcagacc   300
aacccgtatg tgcgcaaatt tctgctggcg accccgtggc agccggcgct gtgcggcgtg   360
tttgcgggcg cgctgcgcta tccgcgctat cgctggattg ataaagtgat gattggcctg   420
attatgcgca tgaccggcgg cgaaaccgat accagcaaag aagtggaata taccgattgg   480
gaacaggtga aaaaatttgc ggaagatttt gcgaaactga gctataaaaa agcgctg      537
```

<210> SEQ ID NO 267
<211> LENGTH: 537
<212> TYPE: DNA
<213> ORGANISM: Artificial Sequence
<220> FEATURE:
<223> OTHER INFORMATION: Recombinant

<400> SEQUENCE: 267

```
atgaaagcgc tggtgctgta tagcacccgc gatggccaga cccatgcgat tgcgagctat    60
attgcgagct gcatgaaaga aaaagcggaa tgcgatgtga ttgatctgac ccatggcgaa   120
catgtgaacc tgacccagta tgatcaggtg ctgattggcg cgagcattcg ctatggccat   180
tttaacgcgg tgctggataa atttattaaa cgcaacgtgg atcagctgaa caacatgccg   240
```

| | |
|---|---|
| agcgcgtttt tttgcgtgaa cctgaccgcg cgcaaaccgg aaaaacgcac cccgcagacc | 300 |
| aacccgtatg tgcgcaaatt tctgctggcg accccgtggc agccggcgct gtgcggcgtg | 360 |
| tttgcgggcg cgctgcgcta tccgcgctat cgctggattg ataaagtgat gattcatctg | 420 |
| attatgcgca tgaccggcgg cgaaaccgat accagcaaag aagtggaata taccgattgg | 480 |
| gaacaggtga aaaatttgc ggaagatttt gcgaaactga gctataaaaa agcgctg | 537 |

```
<210> SEQ ID NO 268
<211> LENGTH: 537
<212> TYPE: DNA
<213> ORGANISM: Artificial Sequence
<220> FEATURE:
<223> OTHER INFORMATION: Recombinant

<400> SEQUENCE: 268
```

| | |
|---|---|
| atgaaagcgc tggtgctgta tagcacccgc gatggccaga cccatgcgat tgcgagctat | 60 |
| attgcgagct gcatgaaaga aaaagcggaa tgcgatgtga ttgatctgac ccatggcgaa | 120 |
| catgtgaacc tgacccagta tgatcaggtg ctgattggcg cgagcattcg ctatggccat | 180 |
| tttaacgcgg tgctggataa atttattaaa cgcaacgtgg atcagctgaa caacatgccg | 240 |
| agcgcgtttt tttgcgtgaa cctgaccgcg cgcaaaccgg aaaaacgcac cccgcagacc | 300 |
| aacccgtatg tgcgcaaatt tctgctggcg accccgtggc agccggcgct gtgcggcgtg | 360 |
| tttgcgggcg cgctgcgcta tccgcgctat cgctggattg ataaagtgat gattaaactg | 420 |
| attatgcgca tgaccggcgg cgaaaccgat accagcaaag aagtggaata taccgattgg | 480 |
| gaacaggtga aaaatttgc ggaagatttt gcgaaactga gctataaaaa agcgctg | 537 |

```
<210> SEQ ID NO 269
<211> LENGTH: 537
<212> TYPE: DNA
<213> ORGANISM: Artificial Sequence
<220> FEATURE:
<223> OTHER INFORMATION: Recombinant

<400> SEQUENCE: 269
```

| | |
|---|---|
| atgaaagcgc tggtgctgta tagcacccgc gatggccaga cccatgcgat tgcgagctat | 60 |
| attgcgagct gcatgaaaga aaaagcggaa tgcgatgtga ttgatctgac ccatggcgaa | 120 |
| catgtgaacc tgacccagta tgatcaggtg ctgattggcg cgagcattcg ctatggccat | 180 |
| tttaacgcgg tgctggataa atttattaaa cgcaacgtgg atcagctgaa caacatgccg | 240 |
| agcgcgtttt tttgcgtgaa cctgaccgcg cgcaaaccgg aaaaacgcac cccgcagacc | 300 |
| aacccgtatg tgcgcaaatt tctgctggcg accccgtggc agccggcgct gtgcggcgtg | 360 |
| tttgcgggcg cgctgcgcta tccgcgctat cgctggattg ataaagtgat gattctgctg | 420 |
| attatgcgca tgaccggcgg cgaaaccgat accagcaaag aagtggaata taccgattgg | 480 |
| gaacaggtga aaaatttgc ggaagatttt gcgaaactga gctataaaaa agcgctg | 537 |

```
<210> SEQ ID NO 270
<211> LENGTH: 537
<212> TYPE: DNA
<213> ORGANISM: Artificial Sequence
<220> FEATURE:
<223> OTHER INFORMATION: Recombinant

<400> SEQUENCE: 270
```

| | |
|---|---|
| atgaaagcgc tggtgctgta tagcacccgc gatggccaga cccatgcgat tgcgagctat | 60 |
| attgcgagct gcatgaaaga aaaagcggaa tgcgatgtga ttgatctgac ccatggcgaa | 120 |

```
catgtgaacc tgacccagta tgatcaggtg ctgattggcg cgagcattcg ctatggccat    180
tttaacgcgg tgctggataa atttattaaa cgcaacgtgg atcagctgaa caacatgccg    240
agcgcgtttt tttgcgtgaa cctgaccgcg cgcaaaccgg aaaaacgcac cccgcagacc    300
aacccgtatg tgcgcaaatt tctgctggcg accccgtggc agccggcgct gtgcggcgtg    360
tttgcgggcg cgctgcgcta tccgcgctat cgctggattg ataaagtgat gattatgctg    420
attatgcgca tgaccggcgg cgaaaccgat accagcaaag aagtggaata taccgattgg    480
gaacaggtga aaaatttgc ggaagatttt gcgaaactga gctataaaaa agcgctg       537
```

<210> SEQ ID NO 271
<211> LENGTH: 537
<212> TYPE: DNA
<213> ORGANISM: Artificial Sequence
<220> FEATURE:
<223> OTHER INFORMATION: Recombinant

<400> SEQUENCE: 271

```
atgaaagcgc tggtgctgta tagcacccgc gatggccaga cccatgcgat tgcgagctat    60
attgcgagct gcatgaaaga aaaagcggaa tgcgatgtga ttgatctgac ccatggcgaa    120
catgtgaacc tgacccagta tgatcaggtg ctgattggcg cgagcattcg ctatggccat    180
tttaacgcgg tgctggataa atttattaaa cgcaacgtgg atcagctgaa caacatgccg    240
agcgcgtttt tttgcgtgaa cctgaccgcg cgcaaaccgg aaaaacgcac cccgcagacc    300
aacccgtatg tgcgcaaatt tctgctggcg accccgtggc agccggcgct gtgcggcgtg    360
tttgcgggcg cgctgcgcta tccgcgctat cgctggattg ataaagtgat gattcgcctg    420
attatgcgca tgaccggcgg cgaaaccgat accagcaaag aagtggaata taccgattgg    480
gaacaggtga aaaatttgc ggaagatttt gcgaaactga gctataaaaa agcgctg       537
```

<210> SEQ ID NO 272
<211> LENGTH: 537
<212> TYPE: DNA
<213> ORGANISM: Artificial Sequence
<220> FEATURE:
<223> OTHER INFORMATION: Recombinant

<400> SEQUENCE: 272

```
atgaaagcgc tggtgctgta tagcacccgc gatggccaga cccatgcgat tgcgagctat    60
attgcgagct gcatgaaaga aaaagcggaa tgcgatgtga ttgatctgac ccatggcgaa    120
catgtgaacc tgacccagta tgatcaggtg ctgattggcg cgagcattcg ctatggccat    180
tttaacgcgg tgctggataa atttattaaa cgcaacgtgg atcagctgaa caacatgccg    240
agcgcgtttt tttgcgtgaa cctgaccgcg cgcaaaccgg aaaaacgcac cccgcagacc    300
aacccgtatg tgcgcaaatt tctgctggcg accccgtggc agccggcgct gtgcggcgtg    360
tttgcgggcg cgctgcgcta tccgcgctat cgctggattg ataaagtgat gattagcctg    420
attatgcgca tgaccggcgg cgaaaccgat accagcaaag aagtggaata taccgattgg    480
gaacaggtga aaaatttgc ggaagatttt gcgaaactga gctataaaaa agcgctg       537
```

<210> SEQ ID NO 273
<211> LENGTH: 537
<212> TYPE: DNA
<213> ORGANISM: Artificial Sequence
<220> FEATURE:
<223> OTHER INFORMATION: Recombinant

<400> SEQUENCE: 273

```
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcagaac     420
attatgcgca tgaccggcgg cgaaaccgat accagcaaag aagtggaata taccgattgg     480
gaacaggtga aaaatttgc ggaagatttt gcgaaactga gctataaaaa agcgctg         537
```

<210> SEQ ID NO 274
<211> LENGTH: 537
<212> TYPE: DNA
<213> ORGANISM: Artificial Sequence
<220> FEATURE:
<223> OTHER INFORMATION: Recombinant

<400> SEQUENCE: 274

```
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcagcag     420
attatgcgca tgaccggcgg cgaaaccgat accagcaaag aagtggaata taccgattgg     480
gaacaggtga aaaatttgc ggaagatttt gcgaaactga gctataaaaa agcgctg         537
```

<210> SEQ ID NO 275
<211> LENGTH: 537
<212> TYPE: DNA
<213> ORGANISM: Artificial Sequence
<220> FEATURE:
<223> OTHER INFORMATION: Recombinant

<400> SEQUENCE: 275

```
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcagagc     420
attatgcgca tgaccggcgg cgaaaccgat accagcaaag aagtggaata taccgattgg     480
gaacaggtga aaaatttgc ggaagatttt gcgaaactga gctataaaaa agcgctg         537
```

<210> SEQ ID NO 276
<211> LENGTH: 537

<212> TYPE: DNA
<213> ORGANISM: Artificial Sequence
<220> FEATURE:
<223> OTHER INFORMATION: Recombinant

<400> SEQUENCE: 276

```
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcaggtg     420
attatgcgca tgaccggcgg cgaaaccgat accagcaaag aagtggaata taccgattgg     480
gaacaggtga aaaatttgc ggaagatttt gcgaaactga gctataaaaa agcgctg        537
```

<210> SEQ ID NO 277
<211> LENGTH: 537
<212> TYPE: DNA
<213> ORGANISM: Artificial Sequence
<220> FEATURE:
<223> OTHER INFORMATION: Recombinant

<400> SEQUENCE: 277

```
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcagtgg     420
attatgcgca tgaccggcgg cgaaaccgat accagcaaag aagtggaata taccgattgg     480
gaacaggtga aaaatttgc ggaagatttt gcgaaactga gctataaaaa agcgctg        537
```

<210> SEQ ID NO 278
<211> LENGTH: 537
<212> TYPE: DNA
<213> ORGANISM: Artificial Sequence
<220> FEATURE:
<223> OTHER INFORMATION: Recombinant

<400> SEQUENCE: 278

```
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
```

```
tttgcgggcg  cgctgcgcta  tccgcgctat  cgctggattg  ataaagtgat  gattcagtat    420
attatgcgca  tgaccggcgg  cgaaaccgat  accagcaaag  aagtggaata  taccgattgg    480
gaacaggtga  aaaaatttgc  ggaagatttt  gcgaaactga  gctataaaaa  agcgctg       537
```

US 11,124,803 B2

METHODS AND COMPOSITIONS FOR PPO HERBICIDE TOLERANCE

CROSS-REFERENCE TO RELATED APPLICATIONS

This application claims the benefit of priority of U.S. Provisional Application No. 62/599,386, filed Dec. 15, 2017, the disclosure of which is hereby incorporated by reference in its entirety.

FIELD OF THE INVENTION

The present invention relates to the fields of agriculture, plant biotechnology, and molecular biology. More specifically, the invention relates to recombinant DNA molecules encoding engineered proteins that provide tolerance to herbicides that inhibit protoporphyrinogen oxidase and methods of use thereof.

INCORPORATION OF SEQUENCE LISTING

A computer readable form of a sequence listing is filed with this application by electronic submission and is incorporated into this application by reference in its entirety. The sequence listing is contained in the file named MONS429US_ST25.txt, which is 331 kilobytes in size (measured in operating system MS Windows) and was created on Nov. 28, 2018.

BACKGROUND OF THE INVENTION

Agricultural crop production often utilizes transgenic traits created using the methods of biotechnology. A heterologous gene, also known as a transgene, can be introduced into a plant to produce a transgenic trait. Expression of the transgene in the plant confers a trait, such as herbicide tolerance, to the plant. Examples of transgenic herbicide tolerance traits include glyphosate tolerance, glufosinate tolerance, and dicamba tolerance. With the increase of weed species resistant to the commonly used herbicides, new herbicide tolerance traits are needed in the field. Herbicides of particular interest include herbicides that inhibit protoporphyrinogen oxidase (PPO, EC 1.3.3.4), referred to as PPO herbicides. PPO herbicides provide control of a spectrum of herbicide-resistant weeds, thus making a trait conferring tolerance to these herbicides particularly useful in a cropping system combined with one or more other herbicide-tolerance trait(s). This invention provides novel, engineered herbicide-tolerant protoporphyrinogen oxidases useful for providing PPO herbicide tolerance in plants.

SUMMARY OF THE INVENTION

In one aspect, the present invention provides a recombinant DNA molecule comprising a heterologous promoter operably linked to a nucleic acid molecule encoding a protein with herbicide-tolerant protoporphyrinogen oxidase activity, wherein the protein has at least about 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N. In certain embodiments, the protein has at least about 50% sequence identity, at least about 60% sequence identity, at least about 70% sequence identity, at least about 80% sequence identity, at least about 85% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, and at least about 99% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N. In some embodiments, the protein comprises at least 2, at least 3, at least 4, at least 5, at least 6, at least 7, at least 8, at least 9, or at least 10 of said amino acid substitutions. In another embodiment, the protein has at least about 90% sequence identity to an amino acid sequence selected from the group consisting of SEQ ID NOs:24-124 and 249-263. In another embodiment, the protein comprises a HemG class protoporphyrinogen oxidase enzyme. In a further embodiment, at least a first amino acid substitution is located in a long chain insert loop of such a HemG class protoporphyrinogen oxidase enzyme. In yet a further embodiment, a recombinant DNA molecule of the invention is comprised in a genome of a plant cell.

In certain embodiments, a heterologous promoter, for instance, a promoter functional in a plant cell, is operably linked to the nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N. Such a resulting DNA molecule may further comprise a transit sequence that functions to localize the protein within a cell.

In another aspect, the present invention provides a DNA construct comprising a recombinant DNA molecule provided herein, such as a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N. In another embodiment, an engineered protein is encoded by the recombinant DNA molecule provided herein.

In a further aspect, the present invention provides a transgenic plant, seed, cell, or plant part comprising a recombinant DNA molecule provided herein, such as a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N. In one embodiment, the transgenic plant, seed, cell, or plant part is tolerant to at least one PPO herbicide. In another embodiment, the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100. In a further embodiment, the transgenic plant, seed, cell, or plant part is tolerant to at least a second herbicide.

In another aspect, the invention provides a method for conferring PPO herbicide tolerance to a plant, seed, cell, or plant part comprising: heterologously expressing an engineered protein of the invention in said plant, seed, cell, or plant part. In some embodiments, the herbicide tolerance is to at least one PPO herbicide selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

In yet another aspect, the invention provides a method for producing an herbicide-tolerant plant, comprising the steps of: a) transforming a plant cell with a recombinant DNA molecule provided herein, such as a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N; and b) regenerating a plant from the plant cell that comprises the recombinant DNA molecule. In one embodiment, the method further comprises the step of selecting said plant or a progeny thereof for PPO herbicide tolerance. In another embodiment, the method further comprises the step of crossing the regenerated plant with itself or with a second plant to produce progeny.

In another aspect, the present invention provides a method for controlling or preventing weed growth in a plant growth area, comprising applying an effective amount of at least one PPO herbicide to a plant growth area that comprises the transgenic plant or seed as provided herein, such as a transgenic plant or seed comprising a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N, wherein the transgenic plant or seed is tolerant to the PPO herbicide. In certain embodiments, the PPO herbicide selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

In yet another aspect, the present invention provides a method of identifying a nucleotide sequence encoding a protein having herbicide-tolerant protoporphyrinogen oxidase activity, the method comprising: a) transforming an *E. coli* strain lacking herbicide-tolerant PPO enzyme activity with a bacterial expression vector comprising a recombinant DNA molecule provided herein, such as a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N; and b) growing said transformed *E. coli* to identify a protein having herbicide-tolerant protoporphyrinogen oxidase activity.

In yet a further aspect, the present invention provides a method of screening for a herbicide tolerance gene comprising: a) expressing a recombinant DNA molecule provided herein, such as a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N in a plant cell; and b) identifying a plant cell that displays tolerance to a PPO herbicide.

In another aspect, the present invention provides a method of producing a plant tolerant to a PPO herbicide and at least one other herbicide comprising: a) obtaining a transgenic plant comprising a recombinant DNA molecule provided herein, such as a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N; b) crossing the plant with a second plant comprising tolerance to the at least one other herbicide, and c) selecting a progeny plant resulting from said crossing that comprises tolerance to a PPO herbicide and the at least one other herbicide.

In yet another aspect, the present invention provides a method for reducing the development of herbicide-tolerant weeds comprising: a) cultivating in a crop growing environment a transgenic plant comprising a recombinant DNA molecule provided herein, such as a recombinant DNA molecule comprising a heterologous promoter operably linked to a nucleic acid molecule encoding a protein with herbicide-tolerant protoporphyrinogen oxidase activity, wherein the protein has at least 50% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N; and b) applying a PPO herbicide and at least one other herbicide to the crop growing environment, wherein the crop plant is tolerant to the PPO herbicide and the at least one other herbicide. In one embodiment, the PPO herbicide is selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100. In another embodiment, the at least one other herbicide is selected from the group consisting of: an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor. In a further embodiment, the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A and FIG. 1B: Shows a sequence alignment of the long chain insert loop of a subset of 23 microbial HemG PPO enzymes with the conserved long chain insert loop highlighted in black. Sequences are arranged in descending order of overall sequence identity relative to H_N90 (SEQ ID NO:1). HemG001 (SEQ ID NO:11) and HemG003 (SEQ ID NO:13) represent HemG PPO proteins with overall sequence identity above 70% to H_N90. The next 15 unboxed sequences, which are H_N30 (SEQ ID NO:4), H_N40 (SEQ ID NO:5), H_N60 (SEQ ID NO:7), H_N20 (SEQ ID NO:3), H_N70 (SEQ ID NO:8), HemG005 (SEQ ID NO:15), H_N100 (SEQ ID NO:9), HemG002 (SEQ ID NO:12), HemG004 (SEQ ID NO:14), H_N110 (SEQ ID NO:10), H_N10 (SEQ ID NO:2), HemG006 (SEQ ID NO:16), HemG007 (SEQ ID NO:17), H_N50 (SEQ ID NO:6), and HemG013 (SEQ ID NO:23), represent HemG PPO proteins with overall sequence identity of 50-70% to H_N90. The last box of 5 sequences, which are HemG008 (SEQ ID NO:18), HemG009 (SEQ ID NO:19), HemG011 (SEQ ID NO:21), HemG012 (SEQ ID NO:22), and HemG010 (SEQ ID NO:20), represent HemG PPO proteins with overall sequence identity of 40-50% to H_N90.

FIG. 2: Shows the universal genetic code chart showing all possible mRNA triplet codons (where T in the DNA molecule is replaced by U in the RNA molecule) and the amino acid encoded by each codon.

BRIEF DESCRIPTION OF THE SEQUENCES

Figure 3:
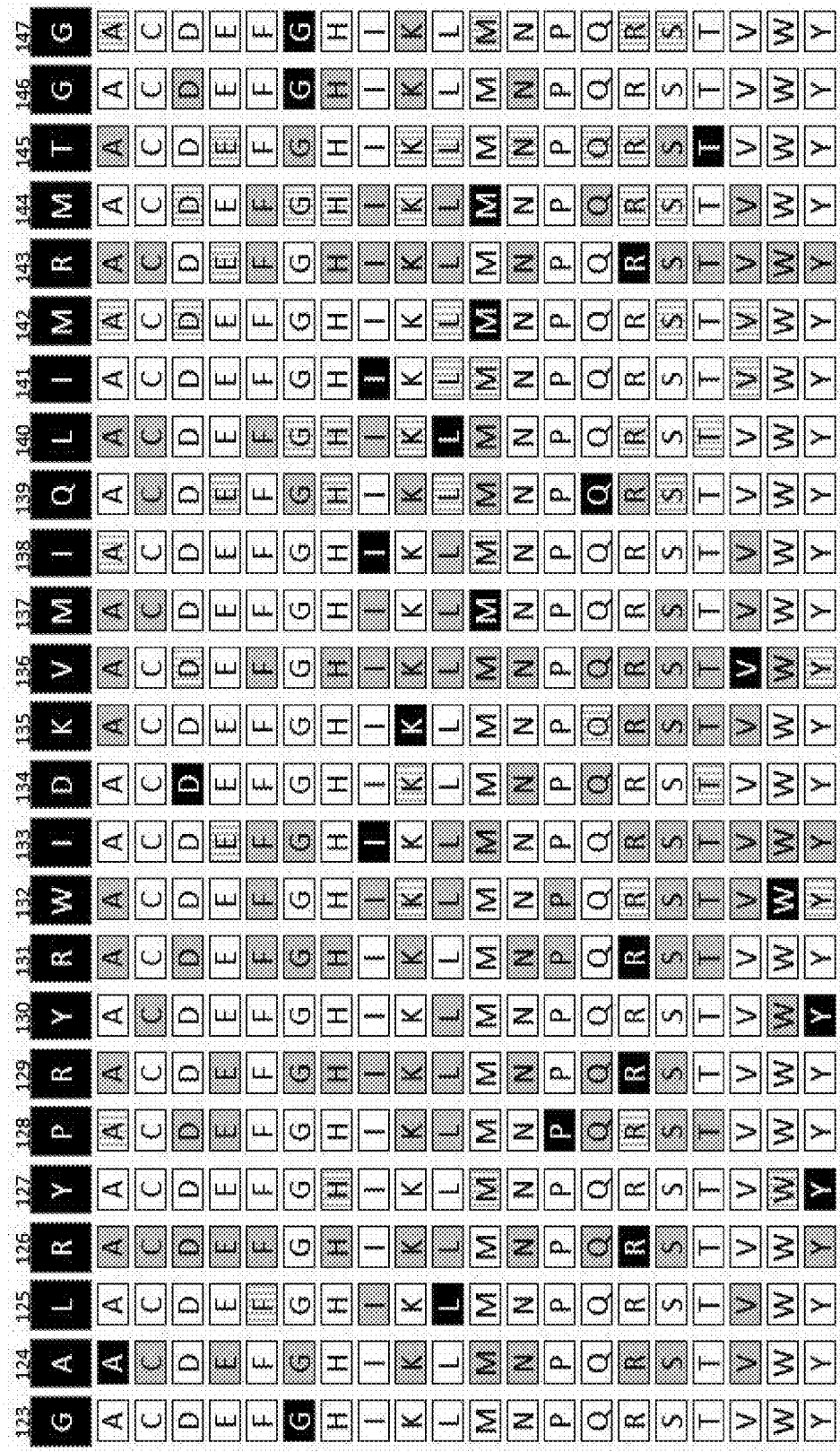
FIG. 3: Shows a diagrammatic representation of all the variation found at each residue in the long chain insert loop of H_N90 (SEQ ID NO:1) from the microbial genomic screen. The black boxes across the top represent the native H_N90 sequence. The boxes below the H_N90 sequence list each of the 20 amino acids. The numbers listed above the H_N90 sequence designate the relative amino acid positions. The solid gray shading represents amino acid variations identified in the ≥50% sequence identity groups. The vertical gray stripe shading represents amino acid variations identified in the 40%-50% sequence identity groups. The remaining white unfilled boxes represent amino acid variations not observed at ≥40% overall sequence identity in the starting microbial dataset.
Figure 4:
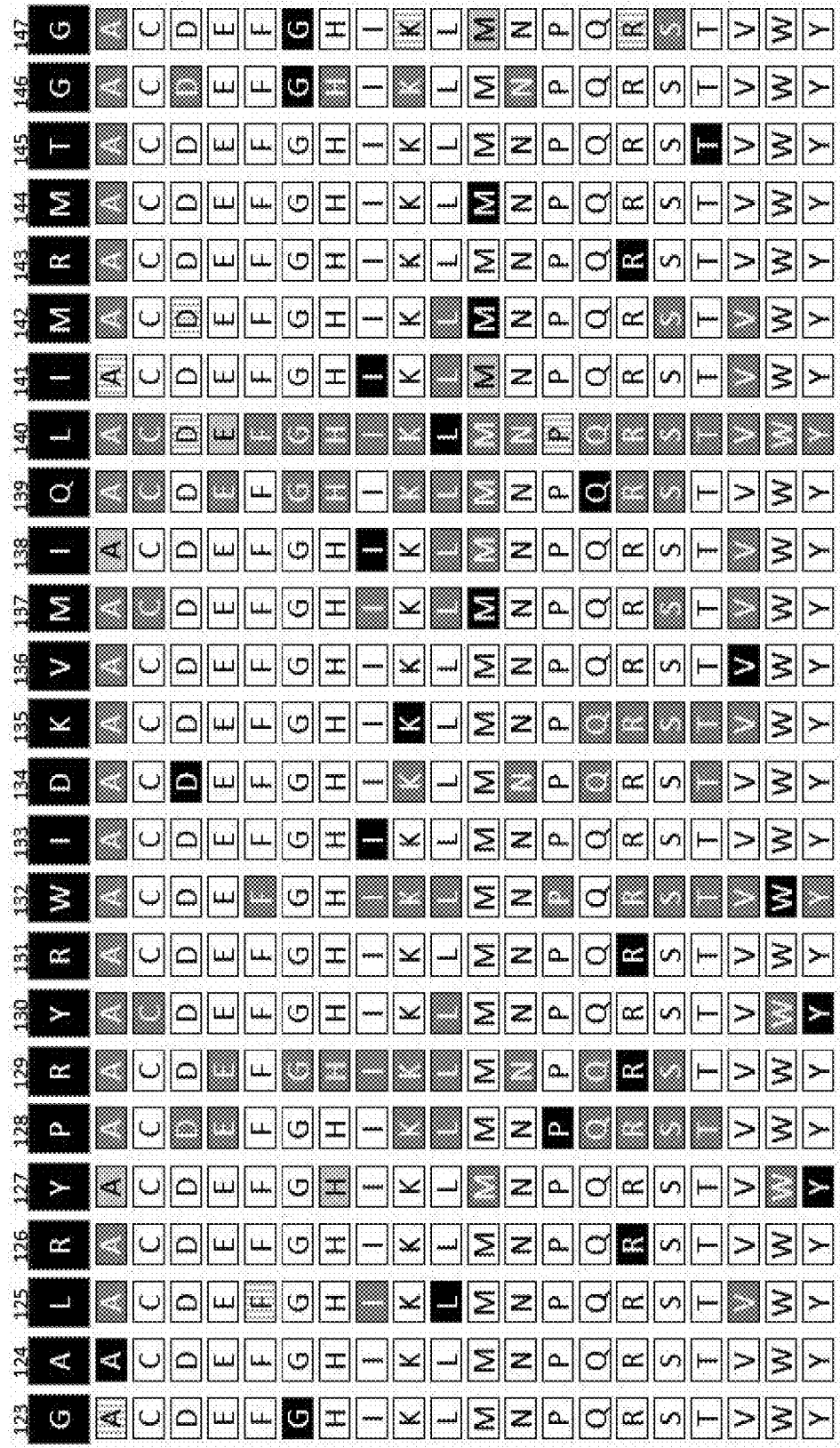
FIG. 4: Shows a diagrammatic representation of the results obtained from the enzyme function assay. The black boxes across the top represent the native H_N90 sequence (SEQ ID NO:1). The boxes below the H_N90 sequence list each of the 20 amino acids. The numbers listed above the H_N90 sequence are the relative amino acid positions. The vertical gray stripe shading indicates that the amino acid modification rendered the enzyme non-functional. The light gray shading with black letters indicates the amino acid modification caused impaired enzyme function. The dark gray shading with white letters indicates the amino acid change kept the enzyme fully functional. The black shading represents the native amino acid in the H_N90 sequence. The remaining white unfilled boxes represent amino acid variations not tested in this assay.
Figure 5:
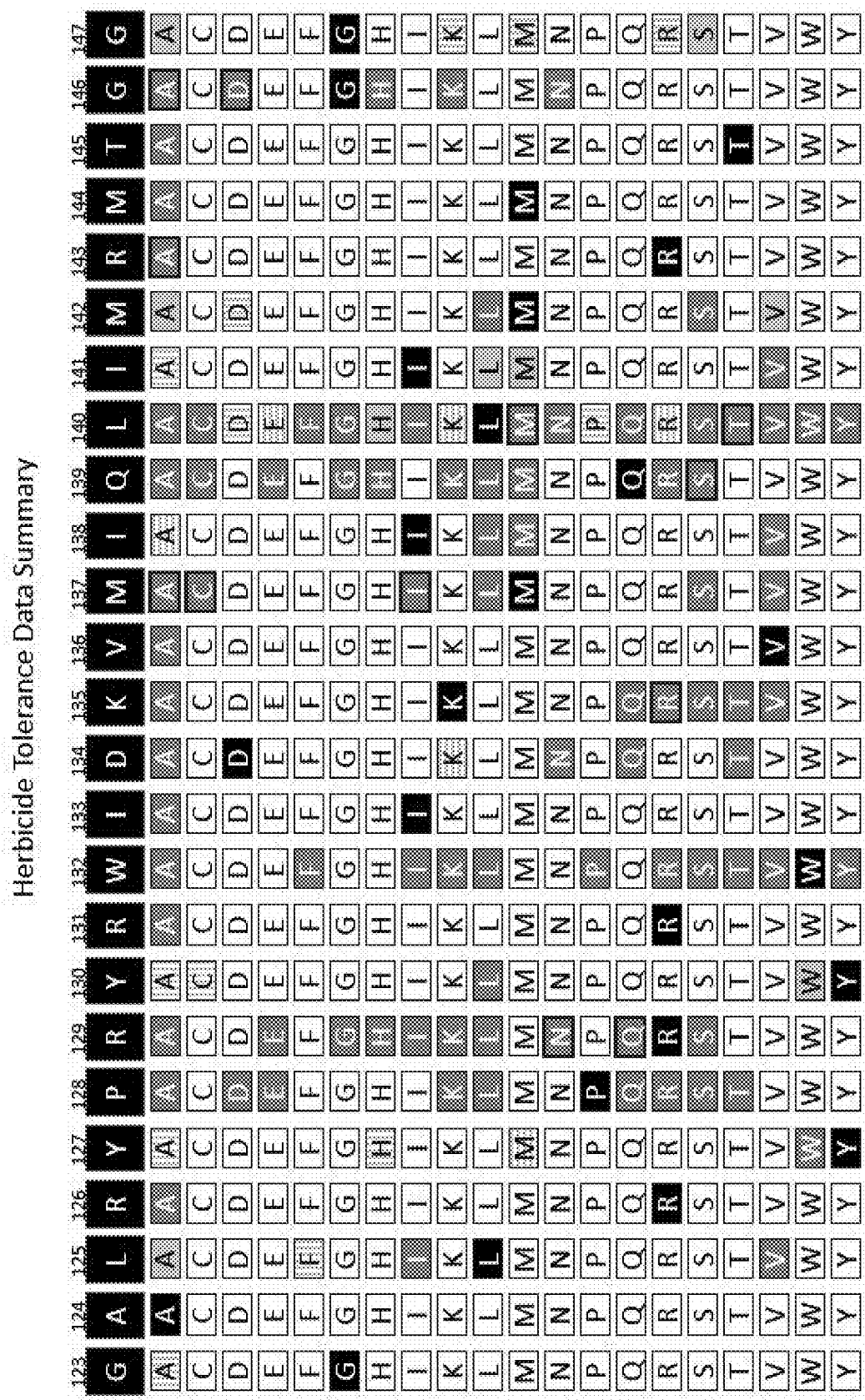
FIG. 5: Shows a diagrammatic version of the results obtained from the herbicide tolerance assay. Tolerance was measured relative to H_N90 tolerance. The black boxes across the top represent the native H_N90 sequence (SEQ ID NO:1). The boxes below the H_N90 sequence list each of the 20 amino acids. The numbers listed above the H_N90 sequence are the relative amino acid positions. The vertical gray stripe shading represents a relative tolerance score of 0-24, which indicates that the amino acid modification conferred little to no herbicide tolerance. The horizontal gray stripe shading represents a relative tolerance score of 25-49, which indicates that the amino acid modification conferred weak herbicide tolerance. The solid light gray shading with black letters represents a relative tolerance score of 50-74, which indicates that the amino acid modification conferred moderate herbicide tolerance. The solid dark gray shading with white letters represents a relative tolerance score of 75-100, which indicates that the amino acid modification conferred good herbicide tolerance. Boxes having dark gray shading and thick black borders represent amino acid modifications showing a relative tolerance score of greater than 100, which indicates that the amino acid modification conferred herbicide tolerance better than that of H_N90. The black shading represents the native amino acid in the H_N90 sequence. The remaining white unfilled boxes represent amino acid variations not tested in this assay.

SEQ ID NO:1 is the amino acid sequence of H_N90.

SEQ ID NO:2 through SEQ ID NO:10 are the amino acid sequences of microbial HemG PPO enzymes with the conserved long chain insert loop.

SEQ ID NO:11 through SEQ ID NO:23 are the amino acid sequences of diverse HemG PPO enzymes with variation in long chain insert loop.

SEQ ID NO:24 through SEQ ID NO:124 and SEQ ID NO:249 through SEQ ID NO:263 are the amino acid sequences of 116 recombinant HemG PPO variants each incorporating a mutation to the long chain insert loop.

SEQ ID NO:125 is a DNA sequence encoding SEQ ID NO:1.

SEQ ID NO:126 through SEQ ID NO:147 are the DNA sequences encoding SEQ ID NO:2 through SEQ ID NO:23, respectively.

SEQ ID NO:148 through SEQ ID NO:248 and SEQ ID NO:264 through SEQ ID NO:278 are the DNA sequences encoding SEQ ID NO:24 through SEQ ID NO:124 and SEQ ID NO:249 through SEQ ID NO:263, respectively.

DETAILED DESCRIPTION

The following descriptions and definitions are provided to better define the invention and to guide those of ordinary skill in the art in the practice of the invention. Unless otherwise noted, terms are to be understood according to conventional usage by those of ordinary skill in the relevant art.

Protoporphyrinogen oxidase functions in both chlorophyll and heme biosynthesis pathways where it converts protoporphyrinogen IX to protoporphyrin IX. Herbicide-tolerant protoporphyrinogen oxidases are useful for producing cells, plants, and seeds that are not sensitive to the application of one or more PPO herbicides and are useful with the methods of agriculture and weed control. The present invention provides novel, engineered proteins that are herbicide-tolerant protoporphyrinogen oxidases, as well as the recombinant DNA molecules encoding these, compositions comprising these, and methods of using these. For example, in one embodiment, the invention provides DNA constructs comprising recombinant DNA molecules encoding engineered herbicide-tolerant protoporphyrinogen oxidases for expression in cells, plants, and seeds. In another embodiment, the invention provides engineered proteins having herbicide-tolerant protoporphyrinogen oxidase activity. In another embodiment, the invention provides methods and compositions for using protein engineering and bioinformatics tools to obtain and improve herbicide-tolerant protoporphyrinogen oxidases. The invention further provides methods and compositions for producing cells, plants, and seeds tolerant to PPO herbicides, and methods of weed control using the cells, plants, and seeds.

The invention provides novel, engineered proteins and the recombinant DNA molecules that encode them. As used herein, the term "engineered" refers to a non-natural DNA, protein, cell, or organism that would not normally be found in nature and was created by human intervention. An "engineered protein," "engineered enzyme," or "engineered PPO," refers to a protein, enzyme, or PPO whose amino acid sequence was conceived of and created in the laboratory using one or more of the techniques of biotechnology, protein design, or protein engineering, such as molecular biology, protein biochemistry, bacterial transformation, plant transformation, site-directed mutagenesis, directed evolution using random mutagenesis, genome editing, gene editing, gene cloning, DNA ligation, DNA synthesis, protein synthesis, and DNA shuffling. For example, an engineered protein may have one or more deletions, insertions, or substitutions relative to the coding sequence of the wild-type protein and each deletion, insertion, or substitution may consist of one or more amino acids. Genetic engineering can be used to create a DNA molecule encoding an engineered protein, such as an engineered PPO that is herbicide tolerant and comprises at least a first amino acid substitution relative to a wild-type PPO protein as described herein.

Examples of engineered proteins provided herein are herbicide-tolerant PPOs comprising one or more amino acid substitution(s) chosen from L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N, including all possible combinations thereof, wherein the position of the amino acid substitution(s) is relative to the amino acid position set forth in SEQ ID NO:1. In specific embodiments, an engineered protein provided herein comprises one, two, three, four, five, six, seven, eight, nine, ten, or more of any combination of such substitutions.

In one embodiment, engineered proteins provided by the invention have herbicide-tolerant protoporphyrinogen oxidase activity. As used herein, "herbicide-tolerant protoporphyrinogen oxidase" means the ability of a protoporphyrinogen oxidase to maintain at least some of its protoporphyrinogen oxidase activity in the presence of one or more PPO herbicide(s). The term "protoporphyrinogen oxidase activity" means the ability to catalyze the six-electron oxidation (removal of electrons) of protoporphyrinogen IX to form protoporphyrin IX, that is, to catalyze the dehydrogenation of protoporphyrinogen to form protoporphyrin. Enzymatic activity of a protoporphyrinogen oxidase can be measured by any means known in the art, for example, by an enzymatic assay in which the production of the product of protoporphyrinogen oxidase or the consumption of the substrate of protoporphyrinogen oxidase in the presence of one or more PPO herbicide(s) is measured via fluorescence, high performance liquid chromatography (HPLC), or mass spectrometry (MS). Another example of an assay for measuring enzymatic activity of a protoporphyrinogen oxidase is a bacterial assay, such as the assays described herein, whereby a recombinant protoporphyrinogen oxidase is expressed in a bacterial cell otherwise lacking PPO activity and the ability of the recombinant protoporphyrinogen oxidase to complement this knockout phenotype is measured. As used herein, a "hemG knockout strain" means an organism or cell of an organism, such as *E. coli*, that lacks HemG activity to the extent that it is unable to grow on heme-free growth medium, or such that its growth is detectably impaired in the absence of heme relative to an otherwise isogenic strain comprising a functional HemG. A hemG knockout strain of, for instance, *E. coli* may be prepared in view of knowledge in the art, for instance in view of the *E. coli* HemG PPO sequence (Ecogene Accession No. EG11485; Sasarman et al., "Nucleotide sequence of the hemG gene involved in the protoporphyrinogen oxidase activity of *E. coli* K12" *Can J Microbiol* 39:1155-1161, 1993).

Engineered proteins may be produced by changing or modifying a wild-type protein sequence to produce a new protein with modified characteristic(s) or a novel combination of useful protein characteristics, such as altered $V_{max}$, $K_m$, $K_i$, $IC_{50}$, substrate specificity, inhibitor/herbicide specificity, substrate selectivity, ability to interact with other components in the cell such as partner proteins or membranes, and protein stability, among others. Modifications may be made at specific amino acid positions in a protein and may be made by substituting an alternate amino acid for the typical amino acid found at that same position in nature (that is, in the wild-type protein). Amino acid modifications may be made as a single amino acid substitution in the protein sequence or in combination with one or more other modifications, such as one or more other amino acid substitution(s), deletions, or additions. In one embodiment of the invention, an engineered protein has altered protein characteristics, such as those that result in decreased sensitivity to one or more herbicides as compared to the wild-type protein or ability to confer tolerance to one or more herbicides on a transgenic plant expressing the engineered protein. In one embodiment, the invention therefore provides an engineered protein such as a PPO enzyme that has herbicide-tolerant protoporphyrinogen oxidase activity, and the recombinant DNA molecule encoding it, having one or more amino acid substitution(s) selected from the group consisting of L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N, and all combinations thereof, wherein the position of the amino acid substitution(s) is relative to the amino acid position set forth in SEQ ID NO:1. In specific embodiments, an engineered protein provided herein comprises one, two, three, four, five, six, seven, eight, nine, ten, or more of any combination of such substitutions, wherein the modification is made at a position relative to a position comparable in function to that in the amino acid sequence provided as SEQ ID NO:1. Amino acid sequences of recombinant or engineered HemG variant PPOs are provided in Table

TABLE 1

Amino Acid Sequences of Recombinant or Engineered HemG Variant PPOs.

| Recombinant HemG Variant | Amino Acid Sequence (SEQ ID NO) | DNA Sequence (SEQ ID NO) |
|---|---|---|
| G123A | 24 | 148 |
| L125A | 25 | 149 |
| L125F | 26 | 150 |
| L125I | 27 | 151 |
| L125V | 28 | 152 |
| R126A | 29 | 153 |
| Y127A | 30 | 154 |
| Y127H | 31 | 155 |
| Y127M | 32 | 156 |
| Y127W | 33 | 157 |
| P128A | 34 | 158 |
| P128D | 35 | 159 |
| P128E | 36 | 160 |
| P128K | 37 | 161 |
| P128L | 38 | 162 |
| P128Q | 39 | 163 |
| P128R | 40 | 164 |
| P128S | 41 | 165 |
| P128T | 42 | 166 |
| R129A | 43 | 167 |
| R129E | 44 | 168 |
| R129G | 45 | 169 |
| R129H | 46 | 170 |
| R129I | 47 | 171 |
| R129K | 48 | 172 |
| R129L | 49 | 173 |
| R129N | 50 | 174 |
| R129Q | 51 | 175 |
| R129S | 52 | 176 |
| Y130A | 53 | 177 |

TABLE 1-continued

Amino Acid Sequences of Recombinant or Engineered HemG Variant PPOs.

| Recombinant HemG Variant | Amino Acid Sequence (SEQ ID NO) | DNA Sequence (SEQ ID NO) |
|---|---|---|
| Y130C | 54 | 178 |
| Y130L | 55 | 179 |
| Y130W | 56 | 180 |
| R131A | 57 | 181 |
| W132A | 58 | 182 |
| W132F | 59 | 183 |
| W132I | 60 | 184 |
| W132K | 61 | 185 |
| W132L | 62 | 186 |
| W132P | 63 | 187 |
| W132R | 64 | 188 |
| W132S | 65 | 189 |
| W132T | 66 | 190 |
| W132V | 67 | 191 |
| W132Y | 68 | 192 |
| I133A | 69 | 193 |
| D134A | 70 | 194 |
| D134K | 71 | 195 |
| D134N | 72 | 196 |
| D134Q | 73 | 197 |
| D134T | 74 | 198 |
| K135A | 75 | 199 |
| K135Q | 76 | 200 |
| K135R | 77 | 201 |
| K135S | 78 | 202 |
| K135T | 79 | 203 |
| K135V | 80 | 204 |
| V136A | 81 | 205 |
| M137A | 82 | 206 |
| M137C | 83 | 207 |
| M137I | 84 | 208 |
| M137L | 85 | 209 |
| M137S | 86 | 210 |
| M137V | 87 | 211 |
| I138A | 88 | 212 |
| I138L | 89 | 213 |
| I138M | 90 | 214 |
| I138V | 91 | 215 |
| L140A | 92 | 216 |
| L140C | 93 | 217 |
| L140F | 94 | 218 |
| L140G | 95 | 219 |
| L140H | 96 | 220 |
| L140I | 97 | 212 |
| L140K | 98 | 222 |
| L140M | 99 | 223 |
| L140R | 100 | 224 |
| L140T | 101 | 225 |
| I141A | 102 | 226 |
| I141L | 103 | 227 |
| I141M | 104 | 228 |
| I141V | 105 | 229 |
| M142A | 106 | 230 |
| M142D | 107 | 231 |
| M142L | 108 | 232 |
| M142S | 109 | 233 |
| M142V | 110 | 234 |
| R143A | 111 | 235 |
| M144A | 112 | 236 |
| T145A | 113 | 237 |
| G146A | 114 | 238 |
| G146D | 115 | 239 |
| G146H | 116 | 240 |
| G146K | 117 | 241 |
| G146N | 118 | 242 |
| G147A | 119 | 243 |
| G147K | 120 | 244 |
| G147M | 121 | 245 |
| G147R | 122 | 246 |
| G147S | 123 | 247 |
| Q139A | 124 | 248 |
| Q139C | 249 | 264 |
| Q139E | 250 | 265 |
| Q139G | 251 | 266 |

TABLE 1-continued

Amino Acid Sequences of Recombinant
or Engineered HemG Variant PPOs.

| Recombinant<br>HemG Variant | Amino Acid Sequence<br>(SEQ ID NO) | DNA Sequence<br>(SEQ ID NO) |
|---|---|---|
| Q139H | 252 | 267 |
| Q139K | 253 | 268 |
| Q139L | 254 | 269 |
| Q139M | 255 | 270 |
| Q139R | 256 | 271 |
| Q139S | 257 | 272 |
| L140N | 258 | 273 |
| L140Q | 259 | 274 |
| L140S | 260 | 275 |
| L140V | 261 | 276 |
| L140W | 262 | 277 |
| L140Y | 263 | 278 |

Similar modifications can be made in analogous positions of any PPO enzyme by alignment of the amino acid sequence of the PPO enzyme to be mutated with the amino acid sequence of a PPO enzyme that has herbicide-tolerant protoporphyrinogen oxidase activity. One example of a sequence coding a PPO enzyme that has herbicide-tolerant protoporphyrinogen oxidase activity that can be used for alignment is SEQ ID NO:1. FIGS. 1A and 1B show an alignment of H_N90, the PPO enzyme of SEQ ID NO:1, exemplary known PPO enzymes (SEQ ID NOs:2-10), and diverse PPO enzymes (SEQ ID NOs:11-23). It is well within the capability of one of skill in the art to use sequence identity information, as shown in FIGS. 1A and 1B, to make the amino acid modifications described herein, for example, in the proteins of SEQ ID NOs: 2-23, to generate PPO enzymes that have herbicide-tolerant protoporphyrinogen oxidase activity. Amino acid sequences of microbial HemG PPOs are provided in Table 2.

TABLE 2

Amino Acid Sequences of Microbial HemG PPOs.

| HemG PPO<br>Protein | Amino Acid Sequence<br>(SEQ ID NO) | DNA Sequence<br>(SEQ ID NO) |
|---|---|---|
| H_N90 | 1 | 125 |
| H_N10 | 2 | 126 |
| H_N20 | 3 | 127 |
| H_N30 | 4 | 128 |
| H_N40 | 5 | 129 |
| H_N50 | 6 | 130 |
| H_N60 | 7 | 131 |
| H_N70 | 8 | 132 |
| H_N100 | 9 | 133 |
| H_N110 | 10 | 134 |
| HemG001 | 11 | 135 |
| HemG002 | 12 | 136 |
| HemG003 | 13 | 137 |
| HemG004 | 14 | 138 |
| HemG005 | 15 | 139 |
| HemG006 | 16 | 140 |
| HemG007 | 17 | 141 |
| HemG008 | 18 | 142 |
| HemG009 | 19 | 143 |
| HemG010 | 20 | 144 |
| HemG011 | 21 | 145 |
| HemG012 | 22 | 146 |
| HemG013 | 23 | 147 |

As used herein, the term "recombinant" refers to a non-naturally occurring DNA, protein, cell, seed, or organism that is the result of genetic engineering and was created by human intervention. A "recombinant DNA molecule" is a DNA molecule comprising a DNA sequence that does not naturally occur and as such is the result of human intervention, such as a DNA molecule comprising at least two DNA molecules heterologous to each other. An example of a recombinant DNA molecule is a DNA molecule provided herein encoding an herbicide-tolerant protoporphyrinogen oxidase operably linked to a heterologous promoter. A "recombinant protein" is a protein comprising an amino acid sequence that does not naturally occur and as such is the result of human intervention, such as an engineered protein. A recombinant cell, seed, or organism is a cell, seed, or organism comprising transgenic or heterologous DNA or protein, for example a transgenic plant cell, seed, or plant comprising a DNA construct or engineered protein of the invention.

As used herein, "wild-type" means a naturally occurring. A "wild-type DNA molecule," "wild-type protein" is a naturally occurring version of a DNA molecule or protein, that is, a version of a DNA molecule or protein pre-existing in nature. A wild-type version of a DNA molecule or protein may be useful for comparison with a recombinant or engineered DNA molecule or protein. An example of a wild-type protein useful for comparison with the engineered proteins provided by the invention is the PPO enzyme from E. cloacae (H_N90) provided as SEQ ID NO:1.

A "wild-type plant" is a naturally occurring plant. Such wild-type plants may also be useful for comparison with a plant comprising a recombinant or engineered DNA molecule or protein. An example of a wild-type plant useful for comparison with plants comprising a recombinant or engineered DNA molecule or protein may be a plant of the same type as the plant comprising the engineered DNA molecule or protein, such as a protein conferring an herbicide tolerance trait, and as such is genetically distinct from the plant comprising the herbicide tolerance trait.

In certain embodiments, wild-type plants may also be used or referred to as "control plants." As used herein, "control" means an experimental control designed for comparison purposes. For example, a control plant in a transgenic plant analysis is a plant of the same type as the experimental plant (that is, the plant to be tested) but does not contain the transgenic insert, recombinant DNA molecule, or DNA construct of the experimental plant. Examples of control plants useful for comparison with transgenic plants include: for maize plants: non-transgenic LH244 maize (ATCC deposit number PTA-1173); for comparison with soybean plants: non-transgenic A3555 soybean (ATCC deposit number PTA-10207); for comparison with cotton plants: non-transgenic Coker 130 (Plant Variety Protection (PVP) Number 8900252); for comparison with canola or Brassica napus plants: non-transgenic Brassica napus variety 65037 Restorer line (Canada Plant Breeders' Rights Application 06-5517); for comparison with wheat plants: non-transgenic wheat variety Samson germplasm (PVP 1994).

As used herein, the term "DNA" or "DNA molecule" refers to a double-stranded DNA molecule of genomic or synthetic origin (that is, a polymer of deoxyribonucleotide bases or a polynucleotide molecule) read from the 5' (upstream) end to the 3' (downstream) end. As used herein, the term "DNA sequence" refers to the nucleotide sequence of a DNA molecule. The nomenclature used herein corresponds to that of by Title 37 of the United States Code of Federal Regulations § 1.822, and set forth in the tables in WIPO Standard ST.25 (1998), Appendix 2, Tables 1 and 3.

The present disclosure provides a nucleic acid molecule encoding a protein that has herbicide-tolerant protoporphyrinogen oxidase activity, having one or more amino acid substitution(s) selected from the group consisting of L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N, and all combinations thereof, wherein the position of the amino acid substitution(s) is relative to the amino acid position set forth in SEQ ID NO:1.

As used herein, the term "protein-coding DNA molecule" refers to a DNA molecule comprising a DNA sequence that encodes a protein. As used herein, the term "protein" refers to a chain of amino acids linked by peptide (amide) bonds and includes both polypeptide chains that are folded or arranged in a biologically functional way and polypeptide chains that are not. As used herein, a "protein-coding sequence" means a DNA sequence that encodes a protein. As used herein, a "sequence" means a sequential arrangement of nucleotides or amino acids. A "DNA sequence" may refer to a sequence of nucleotides or to the DNA molecule comprising of a sequence of nucleotides; a "protein sequence" may refer to a sequence of amino acids or to the protein comprising a sequence of amino acids. The boundaries of a protein-coding sequence are usually determined by a translation start codon at the 5'-terminus and a translation stop codon at the 3'-terminus.

As used herein, the term "isolated" refers to at least partially separating a molecule from other molecules typically associated with it in its natural state. In one embodiment, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

Any number of methods well known to those skilled in the art can be used to isolate and manipulate a DNA molecule, or fragment thereof, as disclosed herein. For example, polymerase chain reaction (PCR) technology can be used to amplify a particular starting DNA molecule or to produce variants of the original molecule. DNA molecules, or fragment thereof, can also be obtained by other techniques, such as by directly synthesizing the fragment by chemical means, as is commonly practiced by using an automated oligonucleotide synthesizer.

Because of the degeneracy of the genetic code, a variety of different DNA sequences can encode proteins, such as the altered or engineered proteins disclosed herein. For example, FIG. 2 provides the universal genetic code chart showing all possible mRNA triplet codons (where T in the DNA molecule is replaced by U in the RNA molecule) and the amino acid encoded by each codon. DNA sequences encoding PPO enzymes with the amino acid substitutions described herein can be produced by introducing mutations into the DNA sequence encoding a wild-type PPO enzyme using methods known in the art and the information provided in FIG. 2. It is well within the capability of one of skill in the art to create alternative DNA sequences encoding the same, or essentially the same, altered or engineered proteins as described herein. These variant or alternative DNA sequences are within the scope of the embodiments described herein. As used herein, references to "essentially the same" sequence refers to sequences which encode amino acid substitutions, deletions, additions, or insertions that do not materially alter the functional activity of the protein encoded by the DNA molecule of the embodiments described herein. Allelic variants of the nucleotide sequences encoding a wild-type or engineered protein are also encompassed within the scope of the embodiments described herein. Substitution of amino acids other than those specifically exemplified or naturally present in a wild-type or engineered PPO enzyme are also contemplated within the scope of the embodiments described herein, so long as the PPO enzyme having the substitution still retains substantially the same functional activity described herein.

Recombinant DNA molecules of the present invention may be synthesized and modified by methods known in the art, either completely or in part, where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes recombinant DNA molecules and engineered proteins having at least 50% sequence identity, at least 60% sequence identity, at least 70% sequence identity, at least 80% sequence identity, at least 85% sequence identity, at least 90% sequence identity, at least 91% sequence identity, at least 92% sequence identity, at least 93% sequence identity, at least 94% sequence identity, at least 95% sequence identity, at least 96% sequence identity, at least 97% sequence identity, at least 98% sequence identity, and at least 99% sequence identity to any of the recombinant DNA molecule or amino acid sequences provided herein, and having herbicide-tolerant protoporphyrinogen oxidase activity. As used herein, the term "percent sequence identity" or "% sequence identity" refers to the percentage of identical nucleotides or amino acids in a linear polynucleotide or amino acid sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local identity algorithm of Smith and Waterman, the identity alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar Inc., 1228 S. Park St., Madison, Wis. 53715), and MUSCLE (version 3.6) (RC Edgar, "MUSCLE: multiple sequence alignment with high accuracy and high throughput" *Nucleic Acids Research* 32(5):1792-7 (2004)) for instance with default parameters. An "identity fraction" for aligned segments of a test sequence and a reference sequence is the number of identical components that are shared by the two aligned sequences divided by the total number of components in the portion of the reference sequence segment being aligned, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

As used herein, a "DNA construct" is a recombinant DNA molecule comprising two or more heterologous DNA sequences. DNA constructs are useful for transgene expression and may be comprised in vectors and plasmids. DNA constructs may be used in vectors for transformation (that is, the introduction of heterologous DNA into a host cell) to produce recombinant bacteria or transgenic plants and cells (and as such may also be contained in the plastid DNA or genomic DNA of a transgenic plant, seed, cell, or plant part). As used herein, a "vector" means any recombinant DNA molecule that may be used for bacterial or plant transformation. DNA molecules provided by the invention can, for example, be inserted into a vector as part of a DNA construct having the DNA molecule operably linked to a heterologous gene expression element that functions in a plant to affect expression of the engineered protein encoded by the DNA molecule. Methods for making and using DNA constructs and vectors are well known in the art and described in detail in, for example, handbooks and laboratory manuals including Michael R. Green and Joseph Sambrook, "Molecular Cloning: A Laboratory Manual" (Fourth Edition) ISBN:978-1-936113-42-2, Cold Spring Harbor Laboratory Press, NY (2012). The components for a DNA construct, or a vector comprising a DNA construct, include one or more gene expression elements operably linked to a transcribable nucleic acid sequence, such as the following: a promoter for the expression of an operably linked DNA, an operably linked protein-coding DNA molecule, and an operably linked 3' untranslated region (UTR). Gene expression elements useful in practicing the present invention include, but are not limited to, one or more of the following type of elements: promoter, 5' UTR, enhancer, leader, cis-acting element, intron, transit sequence, 3' UTR, and one or more selectable marker transgenes.

The term "transgene" refers to a DNA molecule artificially incorporated into the genome of an organism as a result of human intervention, such as by plant transformation methods. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. As a result of such genomic alteration, the transgenic plant is something distinctly different from the related wild-type plant and the transgenic trait is a trait not naturally found in the wild-type plant. Transgenic plants of the invention comprise the recombinant DNA molecules and engineered proteins provided by the invention.

As used herein, the term "heterologous" refers to the relationship between two or more things not normally associated in nature, for instance that are derived from different sources or not normally found in nature together in any other manner. For example, a DNA molecule or protein may be heterologous with respect to another DNA molecule, protein, cell, plant, seed, or organism if not normally found in nature together or in the same context. In certain embodiments, a first DNA molecule is heterologous to a second DNA molecule if the two DNA molecules are not normally found in nature together in the same context. For instance, a protein-coding recombinant DNA molecule is heterologous with respect to an operably linked promoter if such a combination is not normally found in nature. Similarly, a protein is heterologous with respect to a second operably linked protein, such as a transit peptide, if such combination is not normally found in nature. In another embodiment, a recombinant DNA molecule encoding a PPO enzyme is heterologous with respect to an operably linked promoter that is functional in a plant cell if such combination is not normally found in nature. A recombinant DNA molecule also may be heterologous with respect to a cell, seed, or organism into which it is inserted when it would not naturally occur in that cell, seed, or organism.

A "heterologous protein" is a protein present in a plant, seed, cell, tissue, or organism in which it does not naturally occur or operably linked to a protein with which it is not naturally linked. An example of a heterologous protein is an engineered PPO enzyme comprising at least a first amino acid substitution described herein that is expressed in any plant, seed, cell, tissue, or organism. Another example is a protein operably linked to a second protein, such as a transit peptide or herbicide-tolerant protein, with which it is not naturally linked, or a protein introduced into a plant cell in which it does not naturally occur using the techniques of genetic engineering.

As used herein, "operably linked" means two or more DNA molecules or two or more proteins linked in manner so that one may affect the function of the other. Operably linked DNA molecules or operably linked proteins may be part of a single contiguous molecule and may or may not be adjacent. For example, a promoter is operably linked with a protein-coding DNA molecule in a DNA construct where the two DNA molecules are so arranged that the promoter may affect the expression of the transgene.

The DNA constructs of the invention may include a promoter operably linked to a protein-coding DNA molecule provided by the invention, whereby the promoter drives expression of the engineered protein. Promoters useful in practicing the present invention include those that function in a cell for expression of an operably linked DNA molecule, such as a bacterial or plant promoter. Plant promoters are varied and well known in the art and include, for instance, those that are inducible, viral, synthetic, constitutive, temporally regulated, spatially regulated, or spatio-temporally regulated.

In one embodiment of the invention, a DNA construct provided herein includes a DNA sequence encoding a transit sequence that is operably linked to a heterologous DNA sequence encoding a PPO enzyme, whereby the transit sequence facilitates localizing the protein molecule within the cell. Transit sequences are known in the art as signal sequences, targeting peptides, targeting sequences, localization sequences, and transit peptides. An example of a transit sequence is a chloroplast transit peptide (CTP), a mitochondrial transit sequence (MTS), or a dual chloroplast and mitochondrial transit peptide. By facilitating protein localization within the cell, the transit sequence may increase the accumulation of recombinant protein, protect the protein from proteolytic degradation, or enhance the level of herbicide tolerance, and thereby reduce levels of injury in the cell, seed, or organism after herbicide application. CTPs and other targeting molecules that may be used in connection with the present invention are well known in the art. A DNA sequence encoding a transit sequence may be operably linked to a DNA sequence encoding a PPO enzyme as provided herein. Such operable linkage may involve removal of the starting methionine codon (ATG) at the 5' end of the PPO sequence, although it is not necessary to do so and the transit sequence will facilitate localizing the protein molecule within the cell with or without removal of the starting methionine codon.

As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which are ultimately folded into proteins. A protein-coding DNA molecule may be operably linked to a heterologous promoter in a DNA construct for use in expressing the protein in a cell transformed with the recombinant DNA molecule.

In one aspect, the invention provides cells, tissues, plants, and seeds that comprising the recombinant DNA molecules or engineered proteins of the present invention. These cells, tissues, plants, and seeds comprising the recombinant DNA molecules or engineered proteins exhibit tolerance to one or more PPO herbicide(s).

One method of producing such cells, tissues, plants, and seeds is through plant transformation. Suitable methods for transformation of host plant cells for use with the current invention include any method by which DNA can be introduced into a cell (for example, where a recombinant DNA construct is stably integrated into a plant chromosome) and are well known in the art. Two effective, and widely utilized, methods for cell transformation are *Agrobacterium*-mediated transformation and microprojectile bombardment-mediated transformation. Microprojectile bombardment methods are illustrated, for example, in U.S. Pat. Nos. 5,550,318; 5,538,880; 6,160,208; and 6,399,861. *Agrobacterium*-mediated transformation methods are described, for example in U.S. Pat. No. 5,591,616, which is incorporated herein by reference in its entirety. A cell with a recombinant DNA molecule or engineered protein of the present invention may be selected for the presence of the recombinant DNA molecule or engineered protein, for instance through its encoded enzymatic activity, before or after regenerating such a cell into a plant.

Another method of producing the cells, plants, and seeds of the present invention is through genome modification using site-specific integration or genome editing. Targeted modification of plant genomes through the use of genome editing methods can be used to create improved plant lines through modification of plant genomic DNA. As used herein "site-directed integration" refers to genome editing methods the enable targeted insertion of one or more nucleic acids of interest into a plant genome. Suitable methods for altering a wild-type DNA sequence or a preexisting transgenic sequence or for inserting DNA into a plant genome at a pre-determined chromosomal site include any method known in the art. Exemplary methods include the use of sequence specific nucleases, such as zinc-finger nucleases, engineered or native meganucleases, TALE-endonucleases, or an RNA-guided endonucleases (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system). Several embodiments relate to methods of genome editing by using single-stranded oligonucleotides to introduce precise base pair modifications in a plant genome, as described by Sauer et al., Plant Physiology 170(4):1917-1928 (2016). Methods of genome editing to modify, delete, or insert nucleic acid sequences into genomic DNA are known in the art.

In certain embodiments, the present invention provides modification or replacement of an existing coding sequence, such as a PPO coding sequence or another existing transgenic insert, within a plant genome with a sequence encoding an engineered protein, such as an engineered PPO coding sequence of the present invention, or an expression cassette comprising such an engineered protein. Several embodiments relate to the use of a known genome editing methods, such as zinc-finger nucleases, engineered or native meganucleases, TALE-endonucleases, or an RNA-guided endonuclease (for example, a Clustered Regularly Interspersed Short Palindromic Repeat (CRISPR)/Cas9 system, a CRISPR/Cpf1 system, a CRISPR/CasX system, a CRISPR/CasY system, a CRISPR/Cascade system).

Several embodiments may therefore relate to a recombinant DNA construct comprising an expression cassette(s) encoding a site-specific nuclease and, optionally, any associated protein(s) to carry out genome modification. These nuclease-expressing cassette(s) may be present in the same molecule or vector as a donor template for templated editing or an expression cassette comprising nucleic acid sequence encoding a PPO protein as described herein (in cis) or on a separate molecule or vector (in trans). Several methods for site-directed integration are known in the art involving different sequence-specific nucleases (or complexes of proteins or guide RNA or both) that cut the genomic DNA to produce a double strand break (DSB) or nick at a desired genomic site or locus. As understood in the art, during the process of repairing the DSB or nick introduced by the nuclease enzyme, the donor template DNA, transgene, or expression cassette may become integrated into the genome at the site of the DSB or nick. The presence of the homology arm(s) in the DNA to be integrated may promote the adoption and targeting of the insertion sequence into the plant genome during the repair process through homologous recombination, although an insertion event may occur through non-homologous end joining (NHEJ).

As used herein, the term "double-strand break inducing agent" refers to any agent that can induce a double-strand break (DSB) in a DNA molecule. In some embodiments, the double-strand break inducing agent is a site-specific genome modification enzyme.

As used herein, the term "site-specific genome modification enzyme" refers to any enzyme that can modify a nucleotide sequence in a sequence-specific manner. In some embodiments, a site-specific genome modification enzyme modifies the genome by inducing a single-strand break. In some embodiments, a site-specific genome modification enzyme modifies the genome by inducing a double-strand break. In some embodiments, a site-specific genome modification enzyme comprises a cytidine deaminase. In some embodiments, a site-specific genome modification enzyme comprises an adenine deaminase. In the present disclosure, site-specific genome modification enzymes include endonucleases, recombinases, transposases, deaminases, helicases and any combination thereof. In some embodiments, the site-specific genome modification enzyme is a sequence-specific nuclease.

In one aspect, the endonuclease is selected from a meganuclease, a zinc-finger nuclease (ZFN), a transcription activator-like effector nucleases (TALEN), an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), an RNA-guided nuclease, such as a CRISPR associated nuclease (non-limiting examples of CRISPR associated nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof).

In some embodiments, the site-specific genome modification enzyme is a recombinase. Non-limiting examples of recombinases include a tyrosine recombinase attached to a DNA recognition motif provided herein is selected from the group consisting of a Cre recombinase, a Gin recombinase, a Flp recombinase, and a Tnp1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Any of the DNA of interest provided herein can be integrated into a target site of a chromosome sequence by introducing the DNA of interest and the provided site-specific genome modification enzymes. Any method provided herein can utilize any site-specific genome modification enzyme provided herein.

In one aspect, the invention provides cells, plants, and seeds that are tolerant to PPO inhibitor herbicides. Such cells, plants, and seeds are useful in the methods of agriculture, such as weed control and crop production.

As used herein, "herbicide" is any molecule that is used to control, prevent, or interfere with the growth of one or more plants. Exemplary herbicides include acetyl-CoA carboxylase (ACCase) inhibitors (for example aryloxyphenoxy propionates and cyclohexanediones); acetolactate synthase (ALS) inhibitors (for example sulfonylureas, imidazolinones, triazolopyrimidines, and triazolinones); 5-enolpyruvyl-shikimate-3-phosphate synthase (EPSPS) inhibitors (for example glyphosate), synthetic auxins (for example phenoxys, benzoic acids, carboxylic acids, semicarbazones), photosynthesis (photosystem II) inhibitors (for example triazines, triazinones, nitriles, benzothiadiazoles, and ureas), glutamine synthetase (GS) inhibitors (for example glufosinate and bialaphos), 4-hydroxyphenylpyruvate dioxygenase (HPPD) inhibitors (for example isoxazoles, pyrazolones, and triketones), protoporphyrinogen oxidase (PPO) inhibitors (for example diphenylethers, N-phenylphthalimide, aryl triazinones, and pyrimidinediones), very long-chain fatty acid inhibitors (for example chloroacetamides, oxyacetamides, and pyrazoles), cellulose biosynthesis inhibitors (for example indaziflam), photosystem I inhibitors (for example paraquat), microtubule assembly inhibitors (for example pendimethalin), and phytoene desaturase (PDS) inhibitors (for example norflurazone), among others.

As used herein, a "PPO herbicide" is a chemical that targets and inhibits the enzymatic activity of a protoporphyrinogen oxidase (PPO), which catalyzes the dehydrogenation of protoporphyrinogen IX to form protoporphyrin IX, which is the precursor to heme and chlorophyll. Inhibition of protoporphyrinogen oxidase causes formation of reactive oxygen species, resulting in cell membrane disruption and ultimately the death of susceptible cells. PPO herbicides are well-known in the art and commercially available. Examples of PPO herbicides include, but are not limited to, diphenylethers (such as acifluorfen, its salts and esters, aclonifen, bifenox, its salts and esters, ethoxyfen, its salts and esters, fluoronitrofen, furyloxyfen, halosafen, chlomethoxyfen, fluoroglycofen, its salts and esters, lactofen, its salts and esters, oxyfluorfen, and fomesafen, its salts and esters); thiadiazoles (such as fluthiacet-methyl and thidiazimin); pyrimidinediones or phenyluracils (such as benzfendizone, butafenacil, ethyl [3-2-chloro-4-fluoro-5-(1-methyl-6-trifluoromethyl-2,4-dioxo-1,2,3,4-tetrahydropyrimidin-3-yl) phenoxy]-2-pyridyloxy]acetate (CAS Registry Number 353292-31-6 and referred to herein as S-3100), flupropacil, saflufenacil, and tiafenacil); phenylpyrazoles (such as fluazolate, pyraflufen and pyraflufen-ethyl); oxadiazoles (such as oxadiargyl and oxadiazon); triazolinones (such as azafenidin, bencarbazone, carfentrazone, its salts and esters, and sulfentrazone); oxazolidinediones (such as pentoxazone); N-phenylphthalimides (such as cinidon-ethyl, flumiclorac, flumiclorac-pentyl, and flumioxazin); benzoxazinone derivatives (such as 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione); flufenpyr and flufenpyr-ethyl; pyraclonil; and profluazol. Protoporphyrinogen oxidases and cells, seeds, plants, and plant parts provided by the invention exhibit herbicide-tolerance to one or more PPO herbicide(s).

As used herein, "herbicide-tolerant" or "herbicide-tolerance" means the ability to be wholly or partially unaffected by the presence or application of one of more herbicide(s), for example to resist the toxic effects of an herbicide when applied. A cell or organism is "herbicide-tolerant" if it is able to maintain at least some normal growth or phenotype in the presence of one or more herbicide(s). A trait is an herbicide-tolerance trait if its presence can confer improved tolerance to an herbicide upon a cell, plant, or seed as compared to the wild-type or control cell, plant, or seed. Crops comprising a herbicide-tolerance trait can continue to grow and are minimally affected by the presence of the herbicide. A target enzyme is "herbicide-tolerant" if it exhibits improved enzyme activity relative to a wild-type or control enzyme in the presence of the herbicide. Herbicide-tolerance may be complete or partial insensitivity to a particular herbicide, and may be expressed as a percent (%) tolerance or insensitivity to a particular herbicide.

Contemplated plants which might be produced with an herbicide tolerance trait of the present invention could include, for instance, any plant including crop plants such as soybean (*Glycine max*), maize (*Zea mays*), cotton (*Gossypium* sp.), and *Brassica* plants, among others.

Herbicides may be applied to a plant growth area comprising the plants and seeds provided by the invention as a method for controlling weeds. Plants and seeds provided by the invention comprise an herbicide tolerance trait and as such are tolerant to the application of one or more PPO herbicides. The herbicide application may be the recommended commercial rate (1×) or any fraction or multiple thereof, such as twice the recommended commercial rate (2×). Herbicide rates may be expressed as acid equivalent per pound per acre (lb ae/acre) or acid equivalent per gram per hectare (g ae/ha) or as pounds active ingredient per acre (lb ai/acre) or grams active ingredient per hectare (g ai/ha), depending on the herbicide and the formulation. The herbicide application comprises at least one PPO herbicide. The plant growth area may or may not comprise weed plants at the time of herbicide application. A herbicidally-effective dose of PPO herbicide(s) for use in an area for controlling weeds may consist of a range from about 0.1× to about 30× label rate(s) over a growing season. The 1× label rate for some exemplary PPO herbicides is provided in Table 3. One (1) acre is equivalent to 2.47105 hectares and one (1) pound is equivalent to 453.592 grams. Herbicide rates can be converted between English and metric as: (lb ai/ac) multiplied by 1.12=(kg ai/ha) and (kg ai/ha) multiplied by 0.89= (lb ai/ac).

TABLE 3

Exemplary PPO Herbicides

| PPO Herbicide | Chemical Family | 1X Rate |
| --- | --- | --- |
| acifluorfen | Diphenylethers | 420 g ai/ha |
| fomesafen | Diphenylethers | 420 g ai/ha |
| lactofen | Diphenylethers | 70-220 g ai/ha |
| fluoroglycofen-ethyl | Diphenylethers | 15-40 g ai/ha |
| oxyfluorfen | Diphenylethers | 0.28-2.24 kg ai/ha |
| flumioxazin | N-phenylphthalimide | 70-105 g ai/ha |
| azafenidin | Triazolinone | 240 g ai/ha |
| carfentrazone-ethyl | Triazolinone | 4-36 g ai/ha |
| sulfentrazone | Triazolinone | 0.1-0.42 kg ai/ha |
| fluthiacet-methyl | Thiadiazole | 3-15 g ai/ha |
| oxadiargyl | Oxadiazole | 50-150 g ai/ha |
| oxadiazon | Oxadiazole | 2.24-4.48 kg ai/ha |
| pyraflufen-ethyl | Phenylpyrazole | 6-12 g ai/ha |
| saflufenacil | Pyrimidine dione | 25-50 g/ha |
| S-3100 | Pyrimidine dione | 5-80 g/ha |

Herbicide applications may be sequentially or tank mixed with one, two, or a combination of several PPO herbicides or any other compatible herbicide. Multiple applications of one herbicide or of two or more herbicides, in combination or alone, may be used over a growing season to areas comprising transgenic plants of the invention for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, a "weed" is any undesired plant. A plant may be considered generally undesirable for agriculture or horticulture purposes (for example, *Amaranthus* species) or may be considered undesirable in a particular situation (for example, a crop plant of one species in a field of a different species, also known as a volunteer plant).

The transgenic plants, progeny, seeds, plant cells, and plant parts of the invention may also contain one or more additional traits. Additional traits may be introduced by crossing a plant containing a transgene comprising the recombinant DNA molecules provided by the invention with another plant containing one or more additional trait(s). As used herein, "crossing" means breeding two individual plants to produce a progeny plant. Two plants may thus be crossed to produce progeny that contain the desirable traits from each parent. As used herein "progeny" means the offspring of any generation of a parent plant, and transgenic progeny comprise a DNA construct provided by the invention and inherited from at least one parent plant.

Additional trait(s) also may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation or genome editing on a transgenic plant or plant cell). Such additional traits include, but are not limited to, increased insect resistance, increased water use efficiency, increased yield performance, increased drought resistance, increased seed quality, improved nutritional quality, hybrid seed production, and herbicide-tolerance, in which the trait is measured with respect to a wild-type plant. Exemplary additional herbicide-tolerance traits may include transgenic or non-transgenic tolerance to one or more herbicides such as ACCase inhibitors (for example aryloxyphenoxy propionates and cyclohexanediones), ALS inhibitors (for example sulfonylureas, imidazolinones, triazolopyrimidines, and triazolinones) EPSPS inhibitors (for example glyphosate), synthetic auxins (for example phenoxys, benzoic acids, carboxylic acids, semicarbazones), photosynthesis inhibitors (for example triazines, triazinones, nitriles, benzothiadiazoles, and ureas), glutamine synthesis inhibitors (for example glufosinate), HPPD inhibitors (for example isoxazoles, pyrazolones, and triketones), PPO inhibitors (for example diphenylethers, N-phenylphthalimide, aryl triazinones, and pyrimidinediones), and long-chain fatty acid inhibitors (for example chloroacetamindes, oxyacetamides, and pyrazoles), among others. Examples of herbicide-tolerance proteins useful for producing additional herbicide-tolerance traits are well known in the art and include, but are not limited to, glyphosate-tolerant 5-enolypyruvyl shikimate 3-phosphate synthases (e.g., CP4 EPSPS, 2mEPSPS), glyphosate oxidoreductases (GOX), glyphosate N-acetyltransferases (GAT), herbicide-tolerant acetolactate synthases (ALS)/acetohydroxyacid synthases (AHAS), herbicide-tolerant 4-hydroxyphenylpyruvate dioxygenases (HPPD), dicamba monooxygenases (DMO), phosphinothricin acetyl transferases (PAT), herbicide-tolerant glutamine synthetases (GS), 2,4-dichlorophenoxyproprionate dioxygenases (TfdA), R-2,4-dichlorophenoxypropionate dioxygenases (RdpA), S-2,4-di chlorophenoxypropionate dioxygenases (SdpA), herbicide-tolerant protoporphyrinogen oxidases (PPO), and cytochrome P450 monooxygenases. Exemplary insect resistance traits may include resistance to one or more insect members within one or more of the orders of Lepidoptera, Coleoptera, Hemiptera, Thysanoptera, Diptera, Hymenoptera, and Orthoptera, among others. Such additional traits are well known to one of skill in the art; for example, and a list of such transgenic traits is provided by the United States Department of Agriculture's (USDA) Animal and Plant Health Inspection Service (APHIS).

Transgenic plants and progeny that are tolerant to PPO herbicides may be used with any breeding methods that are known in the art. In plant lines comprising two or more traits, the traits may be independently segregating, linked, or a combination of both in plant lines comprising three or more transgenic traits. Backcrossing to a parental plant and out-crossing with a non-transgenic plant are also contemplated, as is vegetative propagation. Descriptions of breeding methods that are commonly used for different traits and crops are well known to those of skill in the art. To confirm the presence of the transgene(s) in a particular plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and western blots) or by enzymatic function; plant part assays, such as leaf or root assays; and also, by analyzing the phenotype of the whole plant.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly a plant genotype lacking the desired transgenic trait may be referred to as an unconverted genotype, line, inbred, or hybrid.

As used herein, the term "comprising" means "including but not limited to".

Having described the invention in detail, it will be apparent that modifications, variations, and equivalent embodiments are possible without departing the scope of the invention defined in the appended claims. Furthermore, it should be appreciated that the examples in the present disclosure are provided as non-limiting examples.

EXAMPLES

Example 1: Sequence Diversity within the Long Chain Loop of Microbial HemG Proteins A diverse set of HemG PPO enzymes were examined for diversity in the long chain insert loop of the protein. The long chain insert loop is a defining characteristic of microbial HemG PPO enzymes and is approximately 25 residues long with key conserved residues (Boynton et al., *Biochemistry* (2009) 48:6705-6711).

Genomic analysis was conducted using a starting set of 1,013 HemG PPO sequences from various microorganisms. Algorithms were designed to capture both the overall sequence diversity of the proteins and the diversity within the long chain insert loop. The sequences were then sorted into groups based on their overall sequence similarity within the starting set.

To create the first group, all sequences from the starting set with ≥70% sequence identity to the HemG PPO H_N90 (SEQ ID NO:1), which has herbicide-tolerant protoporphyrinogen oxidase activity, were identified. Then, the analysis was repeated to identify sequences that had ≥70% sequence identity to any sequence identified in the first analysis. Lastly, the search was repeated a third time to identify sequences that had ≥70% sequence identity to any sequence identified in the second analysis. The results of the three analyses were pooled together to create the first group, which represented sequences from three iterations of ≥70% sequence identity analyses, for a total of 273 HemG PPO sequences.

The second group was created by focusing on the remaining ungrouped sequences from the starting set. All sequences with 50%-70% sequence identity to the HemG PPO H_N90 were identified. Then, the analysis was repeated to identify sequences that had ≥70% sequence identity to any sequence identified in the first analysis. Lastly, the search was repeated a third time to identify sequences that had ≥70% sequence identity to any sequence identified in the second analysis. The results of the three analyses were pooled together to create the second group, which represented sequences from all three iterations, for a total of 278 HemG PPO sequences.

The third group was created by focusing on the yet remaining ungrouped sequences from the starting set. All sequences with 40%-50% sequence identity to the HemG PPO H_N90 were identified. Then, the analysis was repeated to identify sequences that had ≥70% sequence identity to any sequence identified in the first analysis. A third search was done to identify sequences that had ≥70% sequence identity to any sequence identified in the second analysis, but this last iteration did not capture any additional sequences from the starting set. The results of the two analyses were pooled together to create the third group, which represented sequences from both iterations, for a total of 66 HemG PPO sequences.

The three groups of sequences were then used for analysis of the variation found at each of the 25 amino acids in the long chain insert loop. The long chain insert loop sequence from each PPO was identified and compiled. Surprisingly, the sequence variation in this domain was found to be similar for the first and second groups even though the sequences of these two groups when combined had an overall sequence variation of up to 50% and represented 551 diverse sequences. FIG. 3 provides an overview of the variation found in the long chain insert loop among the 617 sequences from the three groups. Among the 25 amino acid positions of the long chain insert loop, 211 different amino acids were identified from the 617 HemG PPO sequences. FIG. 1A and FIG. 1B show a sequence alignment of the long chain insert loop (highlighted in black) of a subset of 23 microbial HemG PPO sequences.

A group of 17 HemG PPO sequences was selected to represent variation found in the long chain insert loop. The protein sequences of the 17 diverse HemG PPO enzymes, when compared using pairwise sequence alignment, have a percent identity ranging from approximately 15% to 98% identity over the full length of the sequence. These 17 diverse HemG PPO enzymes were tested for protoporphyrinogen oxidase activity and herbicide tolerance.

A protoporphyrinogen oxidase bacterial screening system was used to test proteins for protoporphyrinogen oxidase activity and thus confirm that they are functional PPO enzymes. This screening system used a functional rescue assay in an *E. coli* strain that contained a gene knockout for the *E. coli* HemG PPO enzyme (referred to herein as H_N10 and corresponding to SEQ ID NO: 2). The hemG knockout *E. coli* strain was transformed with bacterial expression vectors each containing an expression cassette for one of the PPO enzymes and cultured on LB medium. The hemG knockout *E. coli* strain showed minimal growth on classical bacterial media (e.g., LB media), but normal growth could be restored when the bacterial media is supplemented with free heme or when a functional protoporphyrinogen oxidase was expressed in the cells. Two controls for comparison were used: Green Fluorescent Protein (GFP) and untransformed cells. Two of the HemG PPO enzymes (HemG014 and HemG015) were not able to rescue the hemG knockout *E. coli* strain (no protoporphyrinogen oxidase activity), two showed a partial rescue with slower growth (intermediate), and the remaining 13 showed a full rescue phenotype (functional). Results are shown in Table 4.

A protoplast herbicide tolerance assay was designed to test the 17 diverse HemG PPO enzymes for herbicide tolerance in plant cells. Recombinant DNA molecules encoding the 17 diverse HemG PPO enzymes (codon optimized for dicot expression) were synthesized and cloned into plant transformation vectors. The expression constructs contained a recombinant DNA molecule encoding one of the 17 diverse HemG PPO enzymes operably linked to a plant promoter, a chloroplast transit peptide, and a 3' untranslated region. Soy protoplasts were transformed using standard methods with the plant transformation vectors. The transformed protoplasts were grown in the presence of the PPO herbicide S-3100 at 1.0 µM concentration or mock treatments (negative control). Protoplasts were then assayed for PPO herbicide tolerance, standardized relative to the score of the HemG PPO enzyme H_N90, which was set at 100. Assays were done in two batches in four replications. Relative tolerance scores were averaged for each and standard error was calculated (SE). The GFP control assays had a tolerance score of 0, confirming that the soybean protoplasts were not tolerant to the PPO herbicide in the absence of an herbicide-tolerance protein. Two of the diverse HemG PPO enzymes (HemG014 and HemG015) provided no tolerance while the other 14 provided tolerance scores ranging from 24 to 89, relative to H_N90. Results are shown in Table 4.

Fifteen of the diverse HemG PPO enzymes were then expressed in transgenic plants, and the transgenic plants were analyzed for PPO herbicide tolerance. Recombinant DNA molecules encoding the 15 diverse HemG PPO enzymes (codon optimized for dicot or monocot expression) were synthesized and cloned into plant transformation vectors. The expression constructs contained a recombinant DNA molecule encoding one of the 15 diverse HemG PPO enzymes operably linked to a plant promoter, a chloroplast transit peptide, and a 3' untranslated region.

Maize cells were transformed with these vectors using *Agrobacterium tumefaciens* and standard methods known in the art. Regenerated $R_0$ transgenic plantlets were grown in the greenhouse. The plants were sprayed at approximately $V_2$ to $V_4$ growth stage with the PPO herbicide S3100 at a rate of 80 g/ha to evaluate tolerance. Plants were evaluated for injury 1-14 days after treatment and injury scores are recorded. The percentage of plants with visual injury scores of 20% or less was calculated for all plants for each of the diverse HemG PPO enzymes. Any construct where 25% or greater of the individual plants show good tolerance (visual injury scores of 20% or less) is considered efficacious for conferring herbicide tolerance. Eight of the diverse HemG PPO enzymes (HemG001, HemG002, HemG003, HemG004, HemG005, HemG006, HemG011, and HemG012) provided a substantial number of maize plants demonstrating tolerance to the PPO herbicide (having 20% injury or less after treatment). Results are shown in Table 4.

Soybean cells were transformed with these vectors using *Agrobacterium tumefaciens* and standard methods known in the art. Regenerated $R_0$ transgenic plantlets were grown in the greenhouse. The plants were sprayed at approximately $V_2$ to $V_4$ growth stage with the PPO herbicide S3100 at a rate of 20 g/ha to evaluate tolerance. Plants were evaluated for injury 1-14 days after treatment and injury scores are recorded. The percentage of plants with visual injury scores of 20% or less was calculated for all plants for each of the diverse HemG PPO enzymes. Any construct where 25% or greater of the individual plants show good tolerance (visual injury scores of 20% or less) is considered efficacious for conferring herbicide tolerance. Ten of the diverse HemG PPO enzymes (HemG001, HemG002, HemG003, HemG004, HemG005, HemG006, HemG007, HemG009, HemG011, and HemG013) provided a substantial number of soybean plants demonstrating tolerance to the PPO herbicide (having 20% injury or less after treatment). Results are shown in Table 4.

TABLE 4

Testing of Diverse HemG PPO Enzymes

| Gene/Protein | PPO Complementation Assay in *E. coli* | Protoplast Tolerance Score (% of H_N90 - CTP) | Maize Pass Rate | Soy Pass Rate |
| --- | --- | --- | --- | --- |
| Control - GFP | none | 0 | no data | no data |
| Control - Blank | none | 7 | no data | no data |
| H_N90 | functional | 100 | no data | no data |
| H_N10 | functional | 61 | no data | no data |
| HemG001 | functional | 85 | 58 | 66 |
| HemG002 | functional | 77 | 43 | 80 |
| HemG003 | functional | 87 | 44 | 66 |
| HemG004 | functional | 87 | 47 | 50 |
| HemG005 | functional | 85 | 29 | 50 |
| HemG006 | functional | 84 | 36 | 100 |
| HemG007 | functional | 81 | no data | 50 |
| HemG008 | functional | 51 | 4 | 0 |
| HemG009 | functional | 82 | no data | 100 |
| HemG010 | intermediate | 24 | 2 | 0 |
| HemG011 | functional | 86 | 52 | 75 |
| HemG012 | intermediate | 45 | 0 | 0 |
| HemG013 | functional | 89 | 30 | 90 |
| HemG014 | none | −9 | 0 | 0 |
| HemG015 | none | −15 | 0 | 0 |

Of the 15 diverse HemG PPO enzymes tested in stably transformed maize and soy (or both), 10 were found to be efficacious for conferring herbicide tolerance (producing greater than 25% of plants having visual injury scores of 20% or less). The sequences of these HemG PPO enzymes that are efficacious for conferring herbicide tolerance to plants are provided as: HemG001 (SEQ ID NO:11), HemG002 (SEQ ID NO:12), HemG003 (SEQ ID NO:13), HemG004 (SEQ ID NO:14), HemG005 (SEQ ID NO:15), HemG006 (SEQ ID NO:16), HemG007 (SEQ ID NO:17), HemG009 (SEQ ID NO:19), HemG011 (SEQ ID NO:21), and HemG013 (SEQ ID NO:23).

Example 2: Functional Characterization of Long Chain Insert Loop Variants

The long chain insert loop of the HemG protein has been described as being essential for PPO enzyme function and many of the residues are reported to be highly conserved (Boynton et al., *Biochemistry* (2009) 48:6705-6711). Recombinant HemG PPO enzymes with amino acid variations introduced within the long chain insert loop were created and then analyzed for changes to enzymatic function in a bacterial assay.

The protoporphyrinogen oxidase bacterial screening system described in Example 2 was used to test variant proteins for protoporphyrinogen oxidase activity. This assay provides a means to quickly and easily assay variant proteins for protoporphyrinogen oxidase activity.

Recombinant HemG PPO enzymes incorporating mutations to the long chain insert loop were designed as follows. Each amino acid of the long chain insert loop was considered independently and ranked in priority based on the amount of variation identified at the position and how much of the variation was found in which of the sequence groups. Based on this assessment, 21 of the 25 amino acids in the long chain insert loop were selected for mutagenesis. Mutations were created in the H_N90 sequence to represent the variation observed at each of these 21 positions, resulting in 109 single amino acid variants. In addition, an alanine scanning mutagenesis was performed using the H_N90 sequence to produce mutants having an alanine at each position in the long chain insert loop that was not already an alanine in H_N90, resulting in 10 additional variants. A total of 119 single amino acid variants were then used for screening.

Recombinant DNA molecules encoding the 119 variants were then synthesized and cloned into expression constructs in bacterial transformation vectors. For each variant, the entire nucleotide sequence was kept identical to that of the H_N90 nucleotide sequence, except for the codon for the mutant amino acid. The expression constructs contained each of the recombinant DNA molecules encoding the 119 variants operably linked to a plant promoter, an APG6 chloroplast transit peptide, and a 3' untranslated region. The positive controls consisted of expression constructs containing the H_N90 coding sequence operably linked to a plant promoter, an APG6 chloroplast transit peptide, and a 3' untranslated region. Each vector was individually transformed into the hemG knockout *E. coli* strain. As negative controls, a mock transformation (no vector present) and a vector for expression of Green Fluorescent Protein (GFP) were individually transformed into the hemG knockout *E. coli* strain.

Each of the 119 variants was screened for its ability to restore normal growth to the hemG knockout *E. coli* strain on LB plates. All plates were scored blindly and independently by three individuals for no growth (variant does not complement), slow growth (variant has reduced enzyme function), or normal growth (variant has full enzyme function and provides full complementation). Growth was measured based on the size of the colonies rather than the number of colonies on the plates, and the three individuals agreed on all ratings. Table 5 shows the results of the assay. In this assay, 105 of the 119 variants restored normal growth, suggesting that these variants have full PPO function; 6 of the 119 variants displayed colony growth at a significantly slower growth rate, suggesting that these variants have reduced PPO function; and 8 out of the 119 variants displayed no colony growth, suggesting that these variants have no PPO function. All of the positive controls showed complementation as expected, although the H_N10 construct grew slower than the H_N90 constructs. FIG. 4 shows a diagrammatic representation of the results of this assay.

TABLE 5

HemG Variant Complementation Assay

| HemG Construct | WT AA | AA Change | AA Position | NT Position | Growth Rate |
|---|---|---|---|---|---|
| GFP Control | | | | | No Growth |
| Mock Control | | | | | No Growth |
| H_N10 | | | | | Slow Growth |
| H_N90 - No CTP | | | | | Normal |
| H_N90 - CTP | | | | | Normal |
| H_N90_G123A | Gly | Ala | 123 | 367 | No Growth |
| H_N90_L125A | Leu | Ala | 125 | 373 | Normal |
| H_N90_L125F | Leu | Phe | 125 | 373 | No Growth |
| H_N90_L125I | Leu | Ile | 125 | 373 | Normal |
| H_N90_L125V | Leu | Val | 125 | 373 | Normal |
| H_N90_R126A | Arg | Ala | 126 | 376 | Normal |
| H_N90_Y127A | Tyr | Ala | 127 | 379 | Slow Growth |
| H_N90_Y127H | Tyr | His | 127 | 379 | Slow Growth |
| H_N90_Y127M | Tyr | Met | 127 | 379 | Normal |
| H_N90_Y127W | Tyr | Trp | 127 | 379 | Normal |
| H_N90_P128A | Pro | Ala | 128 | 382 | Normal |
| H_N90_P128D | Pro | Asp | 128 | 382 | Normal |
| H_N90_P128E | Pro | Glu | 128 | 382 | Normal |
| H_N90_P128K | Pro | Lys | 128 | 382 | Normal |
| H_N90_P128L | Pro | Leu | 128 | 382 | Normal |
| H_N90_P128Q | Pro | Gln | 128 | 382 | Normal |

TABLE 5-continued

HemG Variant Complementation Assay

| HemG Construct | WT AA | AA Change | AA Position | NT Position | Growth Rate |
|---|---|---|---|---|---|
| H_N90_P128R | Pro | Arg | 128 | 382 | Normal |
| H_N90_P128S | Pro | Ser | 128 | 382 | Normal |
| H_N90_P128T | Pro | Thr | 128 | 382 | Normal |
| H_N90_R129A | Arg | Ala | 129 | 385 | Normal |
| H_N90_R129E | Arg | Glu | 129 | 385 | Normal |
| H_N90_R129G | Arg | Gly | 129 | 385 | Normal |
| H_N90_R129H | Arg | His | 129 | 385 | Normal |
| H_N90_R129I | Arg | Ile | 129 | 385 | Normal |
| H_N90_R129K | Arg | Lys | 129 | 385 | Normal |
| H_N90_R129L | Arg | Leu | 129 | 385 | Normal |
| H_N90_R129N | Arg | Asn | 129 | 385 | Normal |
| H_N90_R129Q | Arg | Gln | 129 | 385 | Normal |
| H_N90_R129S | Arg | Ser | 129 | 385 | Normal |
| H_N90_Y130A | Tyr | Ala | 130 | 388 | Normal |
| H_N90_Y130C | Tyr | Cys | 130 | 388 | Normal |
| H_N90_Y130L | Tyr | Leu | 130 | 388 | Normal |
| H_N90_Y130W | Tyr | Trp | 130 | 388 | Normal |
| H_N90_R131A | Arg | Ala | 131 | 391 | Normal |
| H_N90_W132A | Trp | Ala | 132 | 394 | Normal |
| H_N90_W132F | Trp | Phe | 132 | 394 | Normal |
| H_N90_W132I | Trp | Ile | 132 | 394 | Normal |
| H_N90_W132K | Trp | Lys | 132 | 394 | Normal |
| H_N90_W132L | Trp | Leu | 132 | 394 | Normal |
| H_N90_W132P | Trp | Pro | 132 | 394 | Normal |
| H_N90_W132R | Trp | Arg | 132 | 394 | Normal |
| H_N90_W132S | Trp | Ser | 132 | 394 | Normal |
| H_N90_W132T | Trp | Thr | 132 | 394 | Normal |
| H_N90_W132V | Trp | Val | 132 | 394 | Normal |
| H_N90_W132Y | Trp | Tyr | 132 | 394 | Normal |
| H_N90_I133A | Ile | Ala | 133 | 397 | Normal |
| H_N90_D134A | Asp | Ala | 134 | 400 | Normal |
| H_N90_D134K | Asp | Lys | 134 | 400 | Normal |
| H_N90_D134N | Asp | Asn | 134 | 400 | Normal |
| H_N90_D134Q | Asp | Gln | 134 | 400 | Normal |
| H_N90_D134T | Asp | Thr | 134 | 400 | Normal |
| H_N90_K135A | Lys | Ala | 135 | 403 | Normal |
| H_N90_K135Q | Lys | Gln | 135 | 403 | Normal |
| H_N90_K135R | Lys | Arg | 135 | 403 | Normal |
| H_N90_K135S | Lys | Ser | 135 | 403 | Normal |
| H_N90_K135T | Lys | Thr | 135 | 403 | Normal |
| H_N90_K135V | Lys | Val | 135 | 403 | Normal |
| H_N90_V136A | Val | Ala | 136 | 406 | Normal |
| H_N90_M137A | Met | Ala | 137 | 409 | Normal |
| H_N90_M137C | Met | Cys | 137 | 409 | Normal |
| H_N90_M137I | Met | Ile | 137 | 409 | Normal |
| H_N90_M137L | Met | Leu | 137 | 409 | Normal |
| H_N90_M137S | Met | Ser | 137 | 409 | Normal |
| H_N90_M137V | Met | Val | 137 | 409 | Normal |
| H_N90_I138A | Ile | Ala | 138 | 412 | Slow Growth |
| H_N90_I138L | Ile | Leu | 138 | 412 | Normal |
| H_N90_I138M | Ile | Met | 138 | 412 | Normal |
| H_N90_I138V | Ile | Val | 138 | 412 | Normal |
| H_N90_Q139A | Gln | Ala | 139 | 415 | Normal |
| H_N90_Q139C | Gln | Cys | 139 | 415 | Normal |
| H_N90_Q139E | Gln | Glu | 139 | 415 | Normal |
| H_N90_Q139G | Gln | Gly | 139 | 415 | Normal |
| H_N90_Q139H | Gln | His | 139 | 415 | Normal |
| H_N90_Q139K | Gln | Lys | 139 | 415 | Normal |
| H_N90_Q139L | Gln | Leu | 139 | 415 | Normal |
| H_N90_Q139M | Gln | Met | 139 | 415 | Normal |
| H_N90_Q139R | Gln | Arg | 139 | 415 | Normal |
| H_N90_Q139S | Gln | Ser | 139 | 415 | Normal |
| H_N90_L140A | Leu | Ala | 140 | 418 | Normal |
| H_N90_L140C | Leu | Cys | 140 | 418 | Normal |
| H_N90_L140D | Leu | Asp | 140 | 418 | No Growth |
| H_N90_L140E | Leu | Glu | 140 | 418 | Slow Growth |
| H_N90_L140F | Leu | Phe | 140 | 418 | Normal |
| H_N90_L140G | Leu | Gly | 140 | 418 | Normal |
| H_N90_L140H | Leu | His | 140 | 418 | Normal |
| H_N90_L140I | Leu | Ile | 140 | 418 | Normal |
| H_N90_L140K | Leu | Lys | 140 | 418 | Normal |
| H_N90_L140M | Leu | Met | 140 | 418 | Normal |
| H_N90_L140N | Leu | Asn | 140 | 418 | Normal |
| H_N90_L140P | Leu | Pro | 140 | 418 | No Growth |
| H_N90_L140Q | Leu | Gln | 140 | 418 | Normal |

TABLE 5-continued HemG Variant Complementation Assay

| HemG Construct | WT AA | AA Change | AA Position | NT Position | Growth Rate |
|---|---|---|---|---|---|
| H_N90_L140R | Leu | Arg | 140 | 418 | Normal |
| H_N90_L140S | Leu | Ser | 140 | 418 | Normal |
| H_N90_L140T | Leu | Thr | 140 | 418 | Normal |
| H_N90_L140V | Leu | Val | 140 | 418 | Normal |
| H_N90_L140W | Leu | Trp | 140 | 418 | Normal |
| H_N90_L140Y | Leu | Tyr | 140 | 418 | Normal |
| H_N90_I141A | Ile | Ala | 141 | 421 | No Growth |
| H_N90_I141L | Ile | Leu | 141 | 421 | Normal |
| H_N90_I141M | Ile | Met | 141 | 421 | Slow Growth |
| H_N90_I141V | Ile | Val | 141 | 421 | Normal |
| H_N90_M142A | Met | Ala | 142 | 424 | Normal |
| H_N90_M142D | Met | Asp | 142 | 424 | No Growth |
| H_N90_M142L | Met | Leu | 142 | 424 | Normal |
| H_N90_M142S | Met | Ser | 142 | 424 | Normal |
| H_N90_M142V | Met | Val | 142 | 424 | Normal |
| H_N90_R143A | Arg | Ala | 143 | 427 | Normal |
| H_N90_M144A | Met | Ala | 144 | 430 | Normal |
| H_N90_T145A | Thr | Ala | 145 | 433 | Normal |
| H_N90_G146A | Gly | Ala | 146 | 436 | Normal |
| H_N90_G146D | Gly | Asp | 146 | 436 | Normal |
| H_N90_G146H | Gly | His | 146 | 436 | Normal |
| H_N90_G146K | Gly | Lys | 146 | 436 | Normal |
| H_N90_G146N | Gly | Asn | 146 | 436 | Normal |
| H_N90_G147A | Gly | Ala | 147 | 439 | Normal |
| H_N90_G147K | Gly | Lys | 147 | 439 | No Growth |
| H_N90_G147M | Gly | Met | 147 | 439 | Slow Growth |
| H_N90_G147R | Gly | Arg | 147 | 439 | No Growth |
| H_N90_G147S | Gly | Ser | 147 | 439 | Normal |

The results of this assay suggest that, while the long chain insert loop is highly conserved in HemG PPO proteins, there is flexibility at many of the residues within the loop with regard to maintaining enzyme function. This was unexpected based on public reports that state that changes in the residues in the long chain insert loop result in loss of enzymatic function (Zwerschke, D., Karrie, S., Jahn, D. and Jahn, M. (2014) Biosci. Rep. 34(4), art:e00124.doi:10.1042/BSR20140081). In this assay, altered enzyme function was found particularly with mutations that were made at positions G123, L125, Y127, I138, L140, I141, M142 and G147, showing that changes in these positions are important for changing enzyme function.

Example 3: Herbicide Tolerance Characterization of Long Chain Insert Loop Variants Recombinant HemG PPO enzymes with amino acid variations introduced within the long chain insert loop were created and analyzed for changes to herbicide sensitivity in plants. A protoplast herbicide tolerance assay was designed to determine if the variants could confer tolerance to a PPO herbicide in plant cells.

Soy protoplasts were transformed using standard methods with the same expression constructs described in Example 2 but using a plant transformation vector. The transformed protoplasts were grown in the presence of the PPO herbicide S-3100 at 1.0 μM concentration or mock treatments (negative control). Protoplasts were then assayed for PPO herbicide tolerance, expressed relative to the GFP control and H_N90 (allowing derivation of a relative tolerance score to enable comparisons between experiments). Assays were done in two batches in four replications. Relative tolerance scores were averaged for each and standard error was calculated (SE). The GFP control assays had a tolerance score of 0, confirming that the soybean protoplasts were not tolerant to the PPO herbicide in the absence of an herbicide-tolerance protein. The N-N90 assays had a tolerance score of 100. Table 6 shows the results of the assay. 13 variants conferred little to no tolerance (comparable to the untransformed control or the GFP control), 6 variants conferred weak tolerance (comparable to the H_N90 without CTP control), 9 variants conferred marginal tolerance (comparable to the H_N10 control), and 79 variants conferred good tolerance (comparable to the H_N90 with CTP control). 12 variants had relative tolerance scores greater than 100 (better than the H_N90 with CTP control). The amino acid changes in these 12 variants are located on 7 residue positions, with 4 of the positions having more than 1 variant trending above 100. This suggests that these 7 amino acid sites are of particular interest with regard to improved herbicide tolerance. FIG. 5 shows a diagrammatic representation of the results of this assay.

TABLE 6

| HemG Variant Protoplast Assay Results - S3100 | | | | | |
|---|---|---|---|---|---|
| HemG Construct | WT AA | AA Change | AA Position | NT Position | Tolerance Score (% of H_N90 - CTP) |
| GFP Control | | | | | 0 |
| Mock Treatment | | | | | 20 |
| H_N10 | | | | | 62 |
| H_N90 - No CTP | | | | | 39 |
| H_N90 - CTP | | | | | 100 |
| H_N90_G123A | Gly | Ala | 123 | 367 | 19 |
| H_N90_L125A | Leu | Ala | 125 | 373 | 62 |
| H_N90_L125F | Leu | Phe | 125 | 373 | 24 |
| H_N90_L125I | Leu | Ile | 125 | 373 | 97 |
| H_N90_L125V | Leu | Val | 125 | 373 | 84 |
| H_N90_R126A | Arg | Ala | 126 | 376 | 75 |
| H_N90_Y127A | Tyr | Ala | 127 | 379 | 5 |
| H_N90_Y127H | Tyr | His | 127 | 379 | 3 |
| H_N90_Y127M | Tyr | Met | 127 | 379 | 34 |
| H_N90_Y127W | Tyr | Trp | 127 | 379 | 99 |
| H_N90_P128A | Pro | Ala | 128 | 382 | 97 |
| H_N90_P128D | Pro | Asp | 128 | 382 | 92 |
| H_N90_P128E | Pro | Glu | 128 | 382 | 88 |
| H_N90_P128K | Pro | Lys | 128 | 382 | 75 |
| H_N90_P128L | Pro | Leu | 128 | 382 | 79 |
| H_N90_P128Q | Pro | Gln | 128 | 382 | 92 |
| H_N90_P128R | Pro | Arg | 128 | 382 | 91 |
| H_N90_P128S | Pro | Ser | 128 | 382 | 100 |
| H_N90_P128T | Pro | Thr | 128 | 382 | 99 |
| H_N90_R129A | Arg | Ala | 129 | 385 | 97 |
| H_N90_R129E | Arg | Glu | 129 | 385 | 77 |
| H_N90_R129G | Arg | Gly | 129 | 385 | 81 |
| H_N90_R129H | Arg | His | 129 | 385 | 88 |
| H_N90_R129I | Arg | Ile | 129 | 385 | 82 |
| H_N90_R129K | Arg | Lys | 129 | 385 | 89 |
| H_N90_R129L | Arg | Leu | 129 | 385 | 96 |
| H_N90_R129N | Arg | Asn | 129 | 385 | 108 |
| H_N90_R129Q | Arg | Gln | 129 | 385 | 106 |
| H_N90_R129S | Arg | Ser | 129 | 385 | 87 |
| H_N90_Y130A | Tyr | Ala | 130 | 388 | 20 |
| H_N90_Y130C | Tyr | Cys | 130 | 388 | 14 |
| H_N90_Y130L | Tyr | Leu | 130 | 388 | 98 |
| H_N90_Y130W | Tyr | Trp | 130 | 388 | 61 |
| H_N90_R131A | Arg | Ala | 131 | 391 | 93 |
| H_N90_W132A | Trp | Ala | 132 | 394 | 77 |
| H_N90_W132F | Trp | Phe | 132 | 394 | 85 |
| H_N90_W132I | Trp | Ile | 132 | 394 | 99 |
| H_N90_W132K | Trp | Lys | 132 | 394 | 78 |
| H_N90_W132L | Trp | Leu | 132 | 394 | 76 |
| H_N90_W132P | Trp | Pro | 132 | 394 | 75 |
| H_N90_W132R | Trp | Arg | 132 | 394 | 84 |
| H_N90_W132S | Trp | Ser | 132 | 394 | 85 |
| H_N90_W132T | Trp | Thr | 132 | 394 | 85 |
| H_N90_W132V | Trp | Val | 132 | 394 | 83 |
| H_N90_W132Y | Trp | Tyr | 132 | 394 | 95 |
| H_N90_I133A | Ile | Ala | 133 | 397 | 91 |
| H_N90_D134A | Asp | Ala | 134 | 400 | 80 |
| H_N90_D134K | Asp | Lys | 134 | 400 | 38 |

TABLE 6-continued

HemG Variant Protoplast Assay Results - S3100

| HemG Construct | WT AA | AA Change | AA Position | NT Position | Tolerance Score (% of H_N90 - CTP) |
|---|---|---|---|---|---|
| H_N90_D134N | Asp | Asn | 134 | 400 | 87 |
| H_N90_D134Q | Asp | Gln | 134 | 400 | 93 |
| H_N90_D134T | Asp | Thr | 134 | 400 | 94 |
| H_N90_K135A | Lys | Ala | 135 | 403 | 94 |
| H_N90_K135Q | Lys | Gln | 135 | 403 | 95 |
| H_N90_K135R | Lys | Arg | 135 | 403 | 105 |
| H_N90_K135S | Lys | Ser | 135 | 403 | 79 |
| H_N90_K135T | Lys | Thr | 135 | 403 | 93 |
| H_N90_K135V | Lys | Val | 135 | 403 | 90 |
| H_N90_V136A | Val | Ala | 136 | 406 | 98 |
| H_N90_M137A | Met | Ala | 137 | 409 | 105 |
| H_N90_M137C | Met | Cys | 137 | 409 | 106 |
| H_N90_M137I | Met | Ile | 137 | 409 | 109 |
| H_N90_M137L | Met | Leu | 137 | 409 | 100 |
| H_N90_M137S | Met | Ser | 137 | 409 | 89 |
| H_N90_M137V | Met | Val | 137 | 409 | 89 |
| H_N90_I138A | Ile | Ala | 138 | 412 | 31 |
| H_N90_I138L | Ile | Leu | 138 | 412 | 97 |
| H_N90_I138M | Ile | Met | 138 | 412 | 93 |
| H_N90_I138V | Ile | Val | 138 | 412 | 85 |
| H_N90_Q139A | Gln | Ala | 139 | 415 | 90 |
| H_N90_Q139C | Gln | Cys | 139 | 415 | 90 |
| H_N90_Q139E | Gln | Glu | 139 | 415 | 85 |
| H_N90_Q139G | Gln | Gly | 139 | 415 | 94 |
| H_N90_Q139H | Gln | His | 139 | 415 | 89 |
| H_N90_Q139K | Gln | Lys | 139 | 415 | 99 |
| H_N90_Q139L | Gln | Leu | 139 | 415 | 87 |
| H_N90_Q139M | Gln | Met | 139 | 415 | 96 |
| H_N90_Q139R | Gln | Arg | 139 | 415 | 96 |
| H_N90_Q139S | Gln | Ser | 139 | 415 | 101 |
| H_N90_L140A | Leu | Ala | 140 | 418 | 88 |
| H_N90_L140C | Leu | Cys | 140 | 418 | 100 |
| H_N90_L140D | Leu | Asp | 140 | 418 | −5 |
| H_N90_L140E | Leu | Glu | 140 | 418 | 49 |
| H_N90_L140F | Leu | Phe | 140 | 418 | 99 |
| H_N90_L140G | Leu | Gly | 140 | 418 | 95 |
| H_N90_L140H | Leu | His | 140 | 418 | 66 |
| H_N90_L140I | Leu | Ile | 140 | 418 | 97 |
| H_N90_L140K | Leu | Lys | 140 | 418 | 30 |
| H_N90_L140M | Leu | Met | 140 | 418 | 109 |
| H_N90_L140N | Leu | Asn | 140 | 418 | 85 |
| H_N90_L140P | Leu | Pro | 140 | 418 | 6 |
| H_N90_L140Q | Leu | Gln | 140 | 418 | 89 |
| H_N90_L140R | Leu | Arg | 140 | 418 | 46 |
| H_N90_L140S | Leu | Ser | 140 | 418 | 78 |
| H_N90_L140T | Leu | Thr | 140 | 418 | 102 |
| H_N90_L140V | Leu | Val | 140 | 418 | 80 |
| H_N90_L140W | Leu | Trp | 140 | 418 | 80 |

TABLE 6-continued

HemG Variant Protoplast Assay Results - S3100

| HemG Construct | WT AA | AA Change | AA Position | NT Position | Tolerance Score (% of H_N90 - CTP) |
|---|---|---|---|---|---|
| H_N90_L140Y | Leu | Tyr | 140 | 418 | 77 |
| H_N90_I141A | Ile | Ala | 141 | 421 | 20 |
| H_N90_I141L | Ile | Leu | 141 | 421 | 64 |
| H_N90_I141M | Ile | Met | 141 | 421 | 61 |
| H_N90_I141V | Ile | Val | 141 | 421 | 94 |
| H_N90_M142A | Met | Ala | 142 | 424 | 58 |
| H_N90_M142D | Met | Asp | 142 | 424 | 13 |
| H_N90_M142L | Met | Leu | 142 | 424 | 89 |
| H_N90_M142S | Met | Ser | 142 | 424 | 80 |
| H_N90_M142V | Met | Val | 142 | 424 | 50 |
| H_N90_R143A | Arg | Ala | 143 | 427 | 112 |
| H_N90_M144A | Met | Ala | 144 | 430 | 91 |
| H_N90_T145A | Thr | Ala | 145 | 433 | 90 |
| H_N90_G146A | Gly | Ala | 146 | 436 | 104 |
| H_N90_G146D | Gly | Asp | 146 | 436 | 101 |
| H_N90_G146H | Gly | His | 146 | 436 | 93 |
| H_N90_G146K | Gly | Lys | 146 | 436 | 85 |
| H_N90_G146N | Gly | Asn | 146 | 436 | 85 |
| H_N90_G147A | Gly | Ala | 147 | 439 | 50 |
| H_N90_G147K | Gly | Lys | 147 | 439 | 9 |
| H_N90_G147M | Gly | Met | 147 | 439 | 17 |
| H_N90_G147R | Gly | Arg | 147 | 439 | 23 |
| H_N90_G147S | Gly | Ser | 147 | 439 | 54 |

A subset of 39 variants (plus controls) was selected for further analysis. These variants were tested for tolerance to the three additional PPO herbicides flumioxazin, sulfentrazone, and lactofen in assays similar to the S-3100 tolerance assay described above. Transformed protoplasts were treated with flumioxazin (5 nM), sulfentrazone (1 µM), and lactofen (1 µM). Table 7 shows the results of the assay. Of the 39 variants tested, 30 displayed good tolerance to flumioxazin, sulfentrazone, or lactofen and 9 had poor tolerance (tolerance scores below 50, indicated as "PT"). Of the 30 variants that displayed good tolerance, 8 displayed a change in tolerance to one or more herbicides that was greater than the experimental variation relative to S-3100. Of these 8 variants, 4 variants conferred higher tolerance to one or more of the herbicides, which is indicated as "Higher" in Table 7 below, while 4 variants conferred lower tolerance to one or more of the herbicides, which is indicated as "Lower" in Table 7 below. Variants indicated as "NSD" had tolerance scores where the difference in tolerance score is less than standard error for a given data point.

TABLE 7

HemG Variant Protoplast Assay Results - Flumioxazin, Sulfentrazone, and Lactofen

| HemG Construct | WT AA | AA Change | AA Position | NT Position | Tolerance Relative to S-3100 | | |
|---|---|---|---|---|---|---|---|
| | | | | | Flumioxazin | Sulfentrazone | Lactofen |
| GFP Control | | | | | 0 | 0 | 0 |
| H_N10 | | | | | NSD | NSD | Higher |
| H_N90 - No CTP | | | | | Higher | Higher | Higher |
| H_N90 - CTP | | | | | 100 | 100 | 100 |
| H_N90_Y127A | Tyr | Ala | 127 | 379 | PT | PT | PT |
| H_N90_Y127H | Tyr | His | 127 | 379 | PT | PT | PT |
| H_N90_Y127M | Tyr | Met | 127 | 379 | PT | PT | PT |
| H_N90_Y127W | Tyr | Trp | 127 | 379 | NSD | Lower | NSD |
| H_N90_R129N | Arg | Asn | 129 | 385 | NSD | NSD | NSD |
| H_N90_R129Q | Arg | Gln | 129 | 385 | NSD | NSD | NSD |
| H_N90_Y130A | Tyr | Ala | 130 | 388 | PT | PT | PT |
| H_N90_Y130C | Tyr | Cys | 130 | 388 | PT | PT | PT |
| H_N90_Y130L | Tyr | Leu | 130 | 388 | NSD | NSD | NSD |
| H_N90_Y130W | Tyr | Trp | 130 | 388 | NSD | NSD | NSD |
| H_N90_K135R | Lys | Arg | 135 | 403 | NSD | NSD | NSD |

TABLE 7-continued

HemG Variant Protoplast Assay Results - Flumioxazin, Sulfentrazone, and Lactofen

| HemG Construct | WT AA | AA Change | AA Position | NT Position | Tolerance Relative to S-3100 | | |
|---|---|---|---|---|---|---|---|
| | | | | | Flumioxazin | Sulfentrazone | Lactofen |
| H_N90_M137A | Met | Ala | 137 | 409 | NSD | NSD | NSD |
| H_N90_M137C | Met | Cys | 137 | 409 | NSD | NSD | NSD |
| H_N90_M137I | Met | Ile | 137 | 409 | NSD | Lower | NSD |
| H_N90_M137L | Met | Leu | 137 | 409 | NSD | NSD | NSD |
| H_N90_M137S | Met | Ser | 137 | 409 | NSD | NSD | NSD |
| H_N90_M137V | Met | Val | 137 | 409 | NSD | NSD | NSD |
| H_N90_L140A | Leu | Ala | 140 | 418 | NSD | NSD | NSD |
| H_N90_L140C | Leu | Cys | 140 | 418 | NSD | NSD | NSD |
| H_N90_L140F | Leu | Phe | 140 | 418 | NSD | NSD | NSD |
| H_N90_L140G | Leu | Gly | 140 | 418 | NSD | NSD | NSD |
| H_N90_L140H | Leu | His | 140 | 418 | NSD | NSD | Higher |
| H_N90_L140I | Leu | Ile | 140 | 418 | NSD | NSD | NSD |
| H_N90_L140K | Leu | Lys | 140 | 418 | PT | PT | PT |
| H_N90_L140M | Leu | Met | 140 | 418 | NSD | Lower | NSD |
| H_N90_L140R | Leu | Arg | 140 | 418 | PT | PT | PT |
| H_N90_L140T | Leu | Thr | 140 | 418 | NSD | NSD | NSD |
| H_N90_I141A | Ile | Ala | 141 | 421 | PT | PT | PT |
| H_N90_I141L | Ile | Leu | 141 | 421 | NSD | NSD | NSD |
| H_N90_I141M | Ile | Met | 141 | 421 | NSD | NSD | NSD |
| H_N90_I141V | Ile | Val | 141 | 421 | NSD | NSD | NSD |
| H_N90_M142A | Met | Ala | 142 | 424 | NSD | NSD | NSD |
| H_N90_M142D | Met | Asp | 142 | 424 | PT | PT | PT |
| H_N90_M142L | Met | Leu | 142 | 424 | NSD | NSD | Higher |
| H_N90_M142S | Met | Ser | 142 | 424 | NSD | NSD | Higher |
| H_N90_M142V | Met | Val | 142 | 424 | Higher | Higher | NSD |
| H_N90_R143A | Arg | Ala | 143 | 427 | NSD | NSD | NSD |
| H_N90_G146A | Gly | Ala | 146 | 436 | NSD | Lower | NSD |
| H_N90_G146D | Gly | Asp | 146 | 436 | NSD | NSD | NSD |

Of the 8 variants that demonstrated a significant difference in tolerance score to flumioxazin, sulfentrazone, or lactofen compared to their tolerance score to S-3100, 6 variants were located at the hydrophobic residues M137, L140, and M142. The region spanning residues M137 to M142 contains a large number of hydrophobic residues (especially I, L, V, M, A). The analysis of this hydrophobic region suggests that these residues are uniquely important in modulating functionality of the enzyme variant. In addition, these residues are uniquely important in modulating tolerance to different PPO-inhibitor herbicides.

The transformed protoplasts may be challenged with other PPO herbicides, such as diphenylethers (such as acifluorfen, its salts and esters, aclonifen, bifenox, its salts and esters, ethoxyfen, its salts and esters, fluoronitrofen, furyloxyfen, halosafen, chlomethoxyfen, fluoroglycofen, its salts and esters, lactofen's salts and esters, oxyfluorfen, and fomesafen, its salts and esters); thiadiazoles (such as fluthiacet-methyl and thidiazimin); pyrimidinediones or phenyluracils (such as benzfendizone, butafenacil, ethyl [3-2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS Registry Number 353292-31-6 and referred to herein as S-3100), flupropacil, saflufenacil, and tiafenacil); phenylpyrazoles (such as fluazolate, pyraflufen and pyraflufen-ethyl); oxadiazoles (such as oxadiargyl and oxadiazon); triazolinones (such as azafenidin, bencarbazone, and carfentrazone, its salts and esters); oxazolidinediones (such as pentoxazone); N-phenylphthalimides (such as cinidon-ethyl, flumiclorac, and flumiclorac-pentyl); benzoxazinone derivatives (such as 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione); flufenpyr and flufenpyr-ethyl; pyraclonil; and profluazol. A mock treatment can be used as a negative control.

Example 4: Functional and Herbicide Tolerance Characterization of Combinatorial Variants Variants are designed to comprise two or more amino acid modifications within the long chain insert loop in a HemG PPO sequence. These combinatorial variant HemG PPO enzymes are then assayed to determine PPO activity. The combinatorial variant HemG PPO DNA sequences are synthesized and cloned into an expression cassette. A bacterial transformation vector comprising the expression cassette can be transformed into the hemG knockout E. coli strain for the initial high-throughput bacterial rescue screen as described in Example 2. The combinatorial variants are screened for their ability to restore normal growth of the hemG knockout E. coli strain.

The combinatorial variant HemG PPO enzymes are also assayed for their ability to confer tolerance to PPO herbicides to a plant cell. An expression cassette containing the combinatorial variant HemG PPO DNA sequences is used with a plant transformation vector to transform soy protoplasts. The protoplast tolerance assay is conducted as described in Example 3, and the combinatorial variants are screened for their ability to confer herbicide tolerance to plant cells.

Example 5: Expression and Testing of Variant HemG PPO Enzymes in Plants

The microbial HemG PPO variants described in the Examples above may be expressed in stably transformed plants, and these plants can be analyzed for PPO herbicide tolerance.

Twenty-five of the microbial HemG PPO variants were tested in stably transformed maize or soy (or both) for herbicide tolerance. Plant transformation vectors were constructed comprising a recombinant DNA molecule encoding a variant HemG PPO enzyme (with the protein-coding sequence optimized for monocot or dicot expression) operably linked to a plant promoter, transit sequence, and 3'UTR.

In maize, maize cells were transformed with the plant transformation vectors using *Agrobacterium tumefaciens* and standard methods known in the art. Regenerated $R_0$ transgenic plantlets are grown in the greenhouse. The $R_0$ plants were sprayed at approximately $V_2$ to $V_4$ growth stage with S3100 at a rate of 80 g/ha. Plants were then evaluated for injury 1-14 days after treatment and injury scores were recorded. Transgenic plants with a single copy of the transgenic DNA insert (that is, single event plants) were identified, and $R_0$ plants that contained only a single copy and passed herbicide spray testing were selfed to produce $R_1$ seed.

In soybean, excised embryos were transformed with the plant transformation vectors using *Agrobacterium tumefaciens* and standard methods known in the art. Regenerated $R_0$ transgenic plantlets were grown in the greenhouse. The $R_0$ plants were sprayed at approximately $V_2$ to $V_4$ growth stage with S3100 at a rate of 20 g/ha. Plants were then evaluated for injury 1-14 days after treatment and injury scores were recorded. Transgenic plants with a single copy of the transgenic DNA insert (that is, single event plants) were identified, and $R_0$ plants that contained only a single copy and passed herbicide spray testing were selfed to produce $R_1$ seed. For some variant HemG PPO enzymes, $R_1$ plants were grown in the greenhouse and sprayed at approximately $V_2$ to $V_4$ growth stage with S3100 at a rate of 60 g/ha. Plants were then evaluated for injury 1-14 days after treatment and injury scores are recorded.

Transgenic soy and maize plants having visual injury scores of 20% or less were scored as passing the herbicide tolerance screen, thus demonstrating tolerance to the PPO herbicide. The percentage of total plants for each variant HemG PPO enzyme passing the herbicide tolerance screen was calculated. Any construct where 25% or greater of the individual plants show good tolerance (visual injury scores of 20% or less) is considered efficacious for conferring herbicide tolerance.

The testing demonstrated that the results obtained from the protoplast assays (conducted as described above) were consistent with the results obtained in whole plants, validating the use of the protoplast assay a screening tool. Of the 25 microbial HemG PPO variants tested in stably transformed maize or soy (or both), 20 were found to be efficacious for conferring herbicide tolerance (producing greater than 25% of plants having visual injury scores of 20% or less). Of these twenty, 14 had efficacy results higher than the positive control H_N90. Results are provided in Table 8.

TABLE 8

Results of Testing of HemG Variants in Soybean and Maize Plants.

| HemG Construct | Protoplast Tolerance Score | Soybean % Pass | Maize % Pass |
| --- | --- | --- | --- |
| H_N90 | 100 | 50% | 58% |
| H_N90_Y127H | 3 | 0% | |
| H_N90_R129A | 97 | 94% | |
| H_N90_R129E | 77 | 57% | |
| H_N90_R129L | 96 | 62% | |
| H_N90_R129N | 108 | 83% | 53% |
| H_N90_R129Q | 106 | 91% | 52% |
| H_N90_R129K | 89 | 100% | |
| H_N90_Y130C | 14 | 0% | |
| H_N90_Y130L | 98 | 32% | |
| H_N90_Y130W | 61 | 0% | |
| H_N90_K135R | 105 | | 62% |
| H_N90_M137A | 105 | | 67% |
| H_N90_M137C | 106 | | 72% |
| H_N90_M137I | 109 | | 66% |
| H_N90_M137L | 100 | 37% | |
| H_N90_M137S | 89 | 35% | |
| H_N90_M137V | 89 | 28% | |
| H_N90_L140F | 99 | 64% | |
| H_N90_L140H | 66 | 4% | |
| H_N90_L140K | 30 | 0% | |
| H_N90_L140M | 109 | 46% | 51% |
| H_N90_L140T | 102 | | 64% |
| H_N90_R143A | 112 | 94% | 69% |
| H_N90_G146A | 104 | 41% | |
| H_N90_G146D | 101 | 50% | |

In cotton, excised embryos (Coker 130) can be transformed with these vectors using *Agrobacterium tumefaciens* and standard methods known in the art. Regenerated $R_0$ transgenic plantlets are grown in the greenhouse and tested as described above.

Other herbicides can be tested with the transgenic plants for tolerance. This can be done, for example, by growing multiple transgenic plants for each HemG PPO and splitting the plants into groups. The groups are sprayed with PPO herbicide(s) (one PPO herbicide per group) to evaluate tolerance. For example, the transgenic plants are sprayed at approximately the 2-4 true leaf growth stage with lactofen at approximately 220 g ai/ha or 440 g ai/ha or flumioxazin at approximately 210 g/ha or 420 g/ha. Plants are then evaluated for injury 1-14 days after treatment and injury scores are recorded. Unsprayed transgenic plants are used for phenotypic comparison with unsprayed non-transgenic plants.

What is claimed is:

1. A recombinant DNA molecule comprising a heterologous promoter operably linked to a nucleic acid molecule encoding an engineered protein with herbicide-tolerant protoporphyrinogen oxidase activity, wherein the protein has at least 60% sequence identity to an amino acid sequence selected from the group consisting of SEQ ID NOs:1-23 and comprises at least a first amino acid substitution at a position corresponding to residues 125 through 146 of SEQ ID NO:1, wherein the substitution is selected from the group consisting of: L125I, L125V, R126A, Y127W, P128A, P128D, P128E, P128K, P128L, P128Q, P128R, P128S, P128T, R129A, R129E, R129G, R129H, R129I, R129K, R129L, R129N, R129Q, R129S, Y130L, R131A, W132A, W132F, W132I, W132K, W132L, W132P, W132R, W132S, W132T, W132V, W132Y, I133A, D134A, D134N, D134Q, D134T, K135A, K135Q, K135R, K135S, K135T, K135V, V136A, M137A, M137C, M137I, M137L, M137S, M137V, I138L, I138M, I138V, Q139A, Q139C, Q139E, Q139G, Q139H, Q139K, Q139L, Q139M, Q139R, Q139S, L140A, L140C, L140F, L140G, L140H, L140I, L140M, L140N, L140Q, L140S, L140T, L140V, L140W, L140Y, I141V, M142L, M142S, M142V, R143A, M144A, T145A, G146A, G146D, G146H, G146K, and G146N,
   wherein said protein has at least 90% sequence identity to an amino acid sequence selected from the group consisting of SEQ ID NOs:24-124 and 249-263.

2. The recombinant DNA molecule of claim 1, wherein the protein comprises at least 2, at least 3, at least 4, at least 5, at least 6, at least 7, at least 8, at least 9, or at least 10 of said amino acid substitutions.

3. The recombinant DNA molecule of claim 1, wherein said protein comprises a HemG class protoporphyrinogen oxidase enzyme.

4. The recombinant DNA molecule of claim 3, wherein said amino acid substitution is located in a long chain insert loop in said enzyme.

5. The recombinant DNA molecule of claim 1, wherein the heterologous promoter is functional in a plant cell.

6. The recombinant DNA molecule of claim 5, wherein the nucleic acid molecule is operably linked to a DNA molecule encoding a transit sequence that functions to localize said protein within a cell.

7. The recombinant DNA molecule of claim 1, wherein the recombinant DNA molecule is comprised in a genome of a plant cell.

8. A DNA construct comprising the recombinant DNA molecule of claim 1.

9. An engineered protein encoded by the recombinant DNA molecule of claim 1.

10. A transgenic plant, seed, cell, or plant part comprising the recombinant DNA molecule of claim 1.

11. The transgenic plant, seed, cell, or plant part of claim 10, wherein the transgenic plant, seed, cell, or plant part is tolerant to at least one PPO herbicide.

12. The transgenic plant, seed, cell, or plant part of claim 11, wherein the PPO herbicide is selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

13. The transgenic plant, seed, cell, or plant part of claim 12, wherein the transgenic plant, seed, cell, or plant part is tolerant to at least a second herbicide.

14. A method for conferring PPO herbicide tolerance to a plant, seed, cell, or plant part comprising: heterologously expressing in said plant, seed, cell, or plant part the engineered protein of claim 9.

15. The method of claim 14, wherein the herbicide tolerance is to at least one PPO herbicide selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

16. A method for producing an herbicide-tolerant plant, comprising the steps of:
   a) transforming a plant cell with the recombinant DNA molecule of claim 1; and
   b) regenerating a plant from the plant cell that comprises the recombinant DNA molecule.

17. The method of claim 16, further comprising the step of selecting said plant or a progeny thereof for PPO herbicide tolerance.

18. The method of claim 16, further comprising the step of crossing the regenerated plant with itself or with a second plant to produce progeny.

19. A method for controlling or preventing weed growth in a plant growth area, comprising applying an effective amount of at least one PPO herbicide to a plant growth area that comprises the transgenic plant or seed of claim 10, wherein the transgenic plant or seed is tolerant to the PPO herbicide.

20. The method of claim 19, wherein the PPO herbicide selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

21. A method of identifying a nucleotide sequence encoding a protein having herbicide-tolerant protoporphyrinogen oxidase activity, the method comprising:
   a) transforming an E. coli strain lacking herbicide-tolerant PPO enzyme activity with a bacterial expression vector comprising the recombinant DNA molecule of claim 1; and
   b) growing said transformed E. coli to identify a protein having herbicide-tolerant protoporphyrinogen oxidase activity.

22. A method of screening for a herbicide tolerance gene comprising:
   a) expressing the recombinant DNA molecule of claim 1 in a plant cell; and
   b) identifying a plant cell that displays tolerance to a PPO herbicide.

23. A method of producing a plant tolerant to a PPO herbicide and at least one other herbicide comprising:

a) obtaining a plant according to claim 10;
b) crossing the plant with a second plant comprising tolerance to the at least one other herbicide, and
c) selecting a progeny plant resulting from said crossing that comprises tolerance to a PPO herbicide and the at least one other herbicide.

24. A method for reducing the development of herbicide-tolerant weeds comprising:
a) cultivating in a crop growing environment a plant according to claim 10; and
b) applying a PPO herbicide and at least one other herbicide to the crop growing environment, wherein the crop plant is tolerant to the PPO herbicide and the at least one other herbicide.

25. The method of claim 24, wherein the PPO herbicide is selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil, and S-3100.

26. The method of claim 24, wherein the at least one other herbicide is selected from the group consisting of: an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor.

27. The method of claim 26, wherein the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole.

* * * * *